(12) United States Patent
Himmelsbach et al.

(10) Patent No.: US 7,407,955 B2
(45) Date of Patent: Aug. 5, 2008

(54) 8-[3-AMINO-PIPERIDIN-1-YL]-XANTHINES, THE PREPARATION THEREOF AND THEIR USE AS PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Michael Mark, Biberach (DE); Roland Maier, Biberach (DE); Ralf R. H. Lotz, Schemmerhofen (DE); Mohammad Tadayyon, Ulm (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 167 days.

(21) Appl. No.: 10/639,036

(22) Filed: Aug. 12, 2003

(65) Prior Publication Data

US 2004/0097510 A1 May 20, 2004

Related U.S. Application Data

(60) Provisional application No. 60/461,752, filed on Apr. 10, 2003, provisional application No. 60/409,312, filed on Sep. 9, 2002.

(30) Foreign Application Priority Data

| Aug. 21, 2002 | (DE) | ................................ 102 38 243 |
| Mar. 20, 2003 | (DE) | ................................ 103 12 353 |

(51) Int. Cl.

| C07D 473/06 | (2006.01) |
| A61K 31/52 | (2006.01) |
| A61P 3/10 | (2006.01) |
| A61P 19/02 | (2006.01) |
| A61P 3/04 | (2006.01) |
| C07D 519/00 | (2006.01) |

(52) U.S. Cl. ..................... 514/234.2; 544/118; 544/268; 544/269; 544/270; 544/271; 544/272; 544/235; 544/237; 514/248; 514/263.2; 514/263.21; 514/263.22; 514/263.23; 514/263.35; 514/263.34; 514/263.36

(58) Field of Classification Search .................. 544/118, 544/268, 269, 270, 271, 272, 235, 237; 514/248, 514/234.2, 263.2, 263.21, 263.22, 263.23, 514/263.35, 263.34, 263.36

See application file for complete search history.

(56) References Cited

U.S. PATENT DOCUMENTS

| 2,928,833 | A | 3/1960 | Leake |
| 4,005,208 | A | 1/1977 | Bender |
| 4,599,338 | A | 7/1986 | Regnier et al. |
| 5,041,448 | A | 8/1991 | Janssens |
| 5,051,517 | A | 9/1991 | Findeisen |
| 5,223,499 | A | 6/1993 | Greenlee |
| 5,234,897 | A | 8/1993 | Findeisen |
| 5,258,380 | A | 11/1993 | Janssens |
| 5,266,555 | A | 11/1993 | Findeisen |
| 5,389,642 | A | 2/1995 | Dorsch |
| 5,470,579 | A | 11/1995 | Bonte et al. |
| 5,719,279 | A | 2/1998 | Kufner-Muhl et al. |
| 5,753,635 | A | 5/1998 | Buckman |
| 6,303,661 | B1 | 10/2001 | Demuth |
| 6,342,601 | B1 | 1/2002 | Bantick |
| 6,548,481 | B1 | 4/2003 | Demuth et al. |
| 6,579,868 | B1 | 6/2003 | Asano |
| 6,821,978 | B2 | 11/2004 | Chackalamannil |
| 6,869,947 | B2 | 3/2005 | Kanstrup |
| 7,060,722 | B2 | 6/2006 | Kitajima |
| 7,074,794 | B2 | 7/2006 | Kitajima |
| 7,074,798 | B2 | 7/2006 | Yoshikawa |
| 7,074,923 | B2 | 7/2006 | Dahanukar |
| 7,109,192 | B2 | 9/2006 | Hauel |
| 7,179,809 | B2 | 2/2007 | Eckhardt |
| 7,183,280 | B2 | 2/2007 | Himmelsbach |
| 7,192,952 | B2 | 3/2007 | Kanstrup |
| 7,217,711 | B2 | 5/2007 | Eckhardt |
| 7,235,538 | B2 | 6/2007 | Kanstrup et al. |
| 2002/0161001 | A1 | 10/2002 | Kanstrup |
| 2002/0169174 | A1 | 11/2002 | Chackalamannil et al. |
| 2002/0198205 | A1 | 12/2002 | Himmelsbach |
| 2003/0105077 | A1 | 6/2003 | Kanstrup et al. |
| 2003/0199528 | A1 | 10/2003 | Kanstrup |
| 2003/0232987 | A1 | 12/2003 | Dahanukar et al. |

(Continued)

FOREIGN PATENT DOCUMENTS

CA      2136288 A1      5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; Mary-Ellen M. Devlin

(57) ABSTRACT

The present invention relates to substituted xanthines of general formula (I)

wherein $R^1$ to $R^3$ are defined as in claims 1 to 16, the tautomers, the stereoisomers, the mixtures, the prodrugs thereof and the salts thereof which have valuable pharmacological properties, particularly an inhibiting effect on the activity of the enzyme dipeptidylpeptidase-IV (DPP-IV).

21 Claims, No Drawings

U.S. PATENT DOCUMENTS

| | | | |
|---|---|---|---|
| 2003/0236272 A1 | 12/2003 | Carr | |
| 2004/0034014 A1 | 2/2004 | Kanstrup | |
| 2004/0077645 A1* | 4/2004 | Himmelsbach et al. | 514/234.5 |
| 2004/0082570 A1 | 4/2004 | Yoshikawa | |
| 2004/0087587 A1* | 5/2004 | Himmelsbach et al. | 514/234.5 |
| 2004/0116328 A1 | 6/2004 | Yoshikawa | |
| 2004/0122228 A1* | 6/2004 | Maier et al. | 544/117 |
| 2004/0138214 A1* | 7/2004 | Himmelsbach et al. | 514/230.5 |
| 2004/0138215 A1* | 7/2004 | Eckhardt et al. | 514/234.5 |
| 2004/0166125 A1* | 8/2004 | Himmelsbach et al. | 424/400 |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0187227 A1 | 8/2005 | Himmelsbach | |
| 2005/0203095 A1 | 9/2005 | Eckhardt | |
| 2005/0234108 A1 | 10/2005 | Himmelsbach | |
| 2005/0261352 A1 | 11/2005 | Eckhardt | |
| 2006/0004074 A1 | 1/2006 | Eckhardt | |
| 2006/0058323 A1 | 3/2006 | Eckhardt | |
| 2006/0063787 A1 | 3/2006 | Yoshikawa | |
| 2006/0079541 A1 | 4/2006 | Langkopf | |
| 2006/0094722 A1 | 5/2006 | Yasuda | |
| 2006/0100199 A1* | 5/2006 | Yoshikawa et al. | 514/218 |
| 2006/0142310 A1 | 6/2006 | Pfrengle | |
| 2006/0173056 A1 | 8/2006 | Kitajima | |
| 2006/0205711 A1 | 9/2006 | Himmelsbach | |
| 2006/0247226 A1 | 11/2006 | Himmelsbach | |
| 2007/0027168 A1 | 2/2007 | Pfrengle | |
| 2007/0088038 A1 | 4/2007 | Eckhardt | |
| 2007/0093659 A1 | 4/2007 | Bonfanti | |
| 2007/0142383 A1 | 6/2007 | Echardt | |
| 2007/0219178 A1* | 9/2007 | Muramoto | 514/210.21 |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| DE | 10109021 A1 | 9/2002 |
| DE | 10117803 A1 | 10/2002 |
| EP | 0149578 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 | 4/1973 |
| FR | 2 707 641 | 1/1995 |
| JP | 37-4895 | 6/1962 |
| JP | 2003/300977 | 10/2003 |
| JP | 2003300977 | 10/2003 |
| JP | 2006045156 | 2/2006 |
| WO | 91/07945 A1 | 6/1991 |
| WO | WO91007945 | 6/1991 |
| WO | 94/03456 A1 | 2/1994 |
| WO | WO 94/03456 | 2/1994 |
| WO | 99/29695 A1 | 6/1999 |
| WO | WO 02/02560 A2 | 1/2002 |
| WO | 2002/14271 A1 | 2/2002 |
| WO | 2002/24698 A1 | 3/2002 |
| WO | WO 02/068420 A1 | 9/2002 |
| WO | WO 03/004496 A1 | 1/2003 |
| WO | WO 03/024965 A2 | 3/2003 |
| WO | WO 03/057200 A2 | 7/2003 |
| WO | 2003/104229 A1 | 12/2003 |
| WO | 2004/018467 A2 | 3/2004 |
| WO | WO 2004018468 A2 * | 3/2004 |
| WO | 2004/028524 A1 | 4/2004 |
| WO | WO 2004033455 A3 | 4/2004 |
| WO | 2004/041820 A1 | 5/2004 |
| WO | 2004/046148 A1 | 6/2004 |
| WO | 2004/048379 A1 | 6/2004 |
| WO | WO 2004/048379 | 6/2004 |
| WO | WO 2004096806 | 11/2004 |
| WO | WO 2004108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2007/017423 A2 | 2/2007 |

OTHER PUBLICATIONS

International Search Report, Nov. 28, 2003.
Augustyns et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Beljean-Leymarie et al., Hydrazines et hydrazones hétérocycliques. IV. Synthéses de dérivés de l'hydrazine dans la série des imidazo[4,5-d]pyridazinones-4, Can. J. Chem., vol. 61, No. 11, 1983, pp. 2563-2566.
Busso et al., Circulating CD26 is Negatively Associates with Inflammation in Human and Experimental Arthritis, Am. J. Path., vol. 166, No. 2, Feb. 2005, pp. 433-442.
Chemical Abstracts Accession No. 1987:95577: Abstract of Romanenko et al., Synthesis and biological activity of 3-methyl, 7- or 8-alkyl, 7,8-dialkyl, heterocyclic, and cyclohexylaminoxathines, Farm. Zh. (Keiv), vol. 5, 1986, pp. 41-44.
U.S. Appl. No. 11/744,700, filed May 4, 2007, Sieger.
U.S. Appl. No. 11/744,701, filed May 4, 2007, Kohlrausch.
U.S. Appl. No. 11/744,703, filed May 4, 2007, Dugi.
Brittain, H.G., "Methods for the Characterization of Polymorphs: X-Ray Powder Diffraction," Polymorphism in Pharmaceutical Solids, 1999, p. 235-238.
Caira, M.R., "Crystalline polymorphism of organic compounds" Topics in Current Chemsitry, Springer, Berlin, vol. 198, 1998, p. 163-208.
Pospisilik, et al; Dipeptidyl Peptidase IV Inhibitor Treatment Stimulates B-Cell Survival and Islet Neogenesis in Streptozotocin-Induced Diabetic Rats; Diabetes, vol. 52, Mar. 2003 pp. 741-750.
Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.
Wolff, M.E.: "Burger's Medicinal Chemistry and Drug Discovery" Fifthe Edition, vol. 1: Principles and Practice, pp. 975-977, 1994, John Wiley & Sons, Inc.

* cited by examiner

8-[3-AMINO-PIPERIDIN-1-YL]-XANTHINES, THE PREPARATION THEREOF AND THEIR USE AS PHARMACEUTICAL COMPOSITIONS

APPLICATION DATA

This application claims benefit to U.S. provisional application Ser. Nos. 60/409,312 filed Sep. 9, 2002 and 60/461,752 filed Apr. 10, 2003 and German application nos. DE 102 38 243.3 filed Aug. 21, 2002 and DE 103 12 353.9 filed Mar. 20, 2003.

FIELD OF INVENTION

The present invention relates to compounds having valuable pharmacological properties, particularly an inhibiting effect on the activity of the enzyme dipeptidylpeptidase-IV (DPP-IV).

DETAILED DESCRIPTION OF THE INVENTION

The present invention relates to new substituted xanthines of general formula

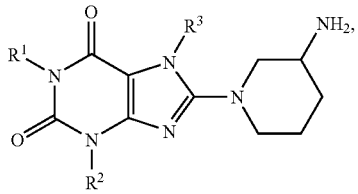

the tautomers, the stereoisomers, the mixtures, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

In the above formula I
$R^1$ denotes a methyl group,
a methyl group which is substituted by a dimethylaminocarbonyl, pyrrolidin-1-ylcarbonyl, piperidin-1-ylcarbonyl, tert.-butylcarbonyl or a cyclohexylcarbonyl-group,
a methyl group which is substituted by a naphthyl, methylnaphthyl, methoxynaphthyl, nitronaphthyl or dimethylaminonaphthyl group,
a methyl group which is substituted by a 2-phenylethenyl or a biphenylyl group,
a methyl group which is substituted by a phenyloxadiazolyl, 5-methyl-3-phenyl-isoxazolyl, phenylpyridinyl, indolyl, benzothiophenyl, quinolinyl, isoquinolinyl, methylisoquinolinyl, (methoxycarbonylmethylamino)-isoquinolinyl, cinnolinyl, quinazolinyl, methylquinazolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group,
a 2-methoxyethyl, 2-phenyloxyethyl or 2-cyanoethyl group,
a phenylcarbonylmethyl or a 1-(phenylcarbonyl)-ethyl group,
a phenylcarbonylmethyl group wherein the phenyl moiety is substituted by an amino, cyanomethylamino, methylcarbonylamino, ethylcarbonylamino, isopropylcarbonylamino, methoxycarbonylamino, (ethyloxycarbonylamino)-carbonylamino or a 2-oxo-imidazolidin-1-yl group,
a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group,
a phenylcarbonylmethyl group wherein the phenyl moiety is substituted by a methylsulphanyl, methylsulphinyl or methylsulphonyl group,
a phenylcarbonylmethyl group wherein the phenyl moiety is substituted by a carboxymethoxy, ethyloxycarbonylmethoxy, isopropyloxycarbonyl methoxy, aminocarbonylmethoxy, methylaminocarbonylmethoxy, ethylaminocarbonylmethoxy, isopropylaminocarbonylmethoxy, dimethylaminocarbonylmethoxy, pyrrolidin-1-ylcarbonylmethoxy or morpholin-4-ylcarbonylmethoxy group,
a phenylcarbonylmethyl group wherein the phenyl moiety is substituted by a 1-(methoxycarbonyl)-ethyloxy or a 1-(aminocarbonyl)-ethyloxy group,
a phenylcarbonylmethyl group wherein the phenyl moiety is substituted by a methylsulphinylmethoxy group,
a phenylcarbonylmethyl group wherein the phenyl moiety is substituted by two methoxy groups, or
a phenylcarbonylmethyl group wherein in the phenyl moiety two adjacent hydrogen atoms are replaced by a —O—CH$_2$—O, —O—CH$_2$—CH$_2$—O or a —N(CH$_3$)—CO—O group,
$R^2$ denotes a hydrogen atom,
a methyl, isopropyl, 2-propen-1-yl, 2-propyn-1-yl, or phenyl group or
a cyanomethyl or methoxycarbonylmethyl group and
$R^3$ denotes a 2-cyanobenzyl or 2,6-dicyanobenzyl group,
a 2-methyl-2-propen-1-yl, 2-chloro-2-propen-1-yl or 3-bromo-2-propen-1-yl group
a 2-buten-1-yl, 3-methyl-2-buten-1-yl or 2,3-dimethyl-2-buten-1-yl group,
a 2-butyn-1-yl group,
a 1-cyclopenten-1-ylmethyl group or
a 2-furanylmethyl group.

The carboxy groups mentioned in the definition of the above mentioned groups may be replaced by a group which can be converted into a carboxy group in vivo or by a group which is negatively charged under physiological conditions,
and furthermore the amino and imino groups mentioned in the definition of the above mentioned groups may be substituted by a group which can be cleaved in vivo. Such groups are described for example in WO 98/46576 and by N. M. Nielsen et al. in International Journal of Pharmaceutics 39, 75-85 (1987).

Compounds which contain a group that can be cleaved in vivo are prodrugs of the corresponding compounds wherein this group that can be cleaved in vivo has been cleaved.

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$- cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

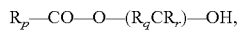

$R_p$—CO—O—($R_q CR_r$)—OH, wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—($R_q CR_r$)—O—CO, $C_{1-6}$-alkyl-CO—NH—($R_s CR_t$)—O—CO— or $C_{1-6}$-alkyl-CO—O—($R_s CR_t$)—($R_s CR_t$)—O—CO— group, wherein $R_p$ to $R_r$ are as hereinbefore defined, $R_s$ and $R_t$, which may be identical or different, denote hydrogen atoms or $C_{1-3}$-alkyl groups.

A first object of the invention relates to compounds of general formula (I) wherein $R^1$ denotes a methyl group which is substituted by a dimethylaminocarbonyl, pyrrolidin-1-ylcarbonyl, piperidin-1-ylcarbonyl, tert.-butylcarbonyl or a cyclohexylcarbonyl group, a methyl group which is substituted by a naphthyl, methylnaphthyl, methoxynaphthyl, nitronaphthyl or (dimethylamino)-naphthyl group, a methyl group which is substituted by a 2-phenylethenyl or a biphenylyl group, a methyl group which is substituted by a phenyl-oxadiazolyl, 5-methyl-3-phenyl-isoxazolyl, phenyl-pyridinyl, indolyl, benzothiophenyl, quinolinyl, isoquinolinyl, methylisoquinolinyl, (methoxycarbonylmethylamino)-isoquinolinyl, cinnolinyl, quinazolinyl, methylquinazolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group, a 2-methoxyethyl, 2-phenyloxyethyl or 2-cyanoethyl group, a phenylcarbonylmethyl or a 1-(phenylcarbonyl)-ethyl group, a phenylcarbonylmethyl group wherein the phenyl moiety is substituted by an amino, cyanomethylamino, methylcarbonylamino, ethylcarbonylamino, isopropylcarbonylamino, methoxycarbonylamino, (ethyloxycarbonylamino)-carbonylamino or a 2-oxo-imidazolidin-1-yl group, a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group, a phenylcarbonylmethyl group wherein the phenyl moiety is substituted by a methylsulphanyl, methylsulphinyl or methylsulphonyl group, a phenylcarbonylmethyl group wherein the phenyl moiety is substituted by a carboxymethoxy, ethyloxycarbonylmethoxy, isopropyloxycarbonyl methoxy, aminocarbonylmethoxy, methylaminocarbonylmethoxy, ethylaminocarbonylmethoxy, isopropylaminocarbonylmethoxy, dimethylaminocarbonylmethoxy, pyrrolidin-1-ylcarbonylmethoxy or morpholin-4-ylcarbonylmethoxy group, a phenylcarbonylmethyl group wherein the phenyl moiety is substituted by a 1-(methoxycarbonyl)-ethyloxy or a 1-(aminocarbonyl)-ethyloxy group, a phenylcarbonylmethyl group wherein the phenyl moiety is substituted by a methylsulphinylmethoxy group, a phenylcarbonylmethyl group wherein the phenyl moiety is substituted by two methoxy groups or a phenylcarbonylmethyl group wherein in the phenyl moiety two adjacent hydrogen atoms are replaced by a —O—$CH_2$—O—, —O—$CH_2$—$CH_2$—O or a —N($CH_3$)—CO—O group, $R^2$ denotes a methyl, isopropyl or phenyl group and $R^3$ denotes a 2-methyl-2-propen-1-yl, 2-chloro-2-propen-1-yl or 3-bromo-2-propen-1-yl group a 2-buten-1-yl or 2,3-dimethyl-2-buten-1-yl group, a 2-butyn-1-yl group, a 1-cyclopenten-1-ylmethyl group or a 2-furanylmethyl group, as well as the compounds (1-(2-cyano-ethyl)-3-methyl-7-(2-cyano-benzyl)-8-(3-amino-piperidin-1-yl)-xanthine, (1-(2-{2-[(ethoxycarbonyl)methoxy]-phenyl}-2-oxo-ethyl)-3-methyl-7-(3-methyl-2-buten-1-yl)-8-(3-amino-piperidin-1-yl)-xanthine,
(1-(2-{2-[(aminocarbonyl)methoxy]-phenyl}-2-oxo-ethyl)-3-methyl-7-(3-methyl-2-buten-1-yl)-8-(3-amino-piperidin-1-yl)-xanthine,
(1-(2-{3-[(methanesulphinyl)methoxy]-phenyl}-2-oxo-ethyl)-3-methyl-7-(3-methyl-2-buten-1-yl)-8-(3-amino-piperidin-1-yl)-xanthine,
(1-(1-methyl-2-oxo-2-phenyl-ethyl)-3-methyl-7-(3-methyl-2-buten-1-yl)-8-(3-amino-piperidin-1-yl)-xanthine,
(1-(2-phenoxy-ethyl)-3-methyl-7-(2-cyano-benzyl)-8-(3-amino-piperidin-1-yl)-xanthine,
(1-(2-phenyl-2-oxo-ethyl)-7-(3-methyl-2-buten-1-yl)-8-(3-amino-piperidin-1-yl)-xanthine,
(1-(2-{3-[(ethoxycarbonyl)methoxy]-phenyl}-2-oxo-ethyl)-3-methyl-7-(3-methyl-2-buten-1-yl)-8-(3-amino-piperidin-1-yl)-xanthine,
(1-(2-{2-[(methylaminocarbonyl)methoxy]-phenyl}-2-oxo-ethyl)-3-methyl-7-(3-methyl-2-buten-1-yl)-8-(3-amino-piperidin-1-yl)-xanthine,
(1-(2-{2-[(dimethylaminocarbonyl)methoxy]-phenyl}-2-oxo-ethyl)-3-methyl-7-(3-methyl-2-buten-1-yl)-8-(3-amino-piperidin-1-yl)-xanthine,
(1-(2-methoxy-ethyl)-3-methyl-7-(2-cyano-benzyl)-8-(3-amino-piperidin-1-yl)-xanthine,
(1-methyl-3-[(methoxycarbonyl)methyl]-7-(2-cyano-benzyl)-8-(3-amino-piperidin-1-yl)-xanthine,
(1-methyl-3-cyanomethyl-7-(2-cyano-benzyl)-8-(3-amino-piperidin-1-yl)-xanthine,
(1-methyl-3-(2-propyn-1-yl)-7-(2-cyano-benzyl)-8-(3-amino-piperidin-1-yl)-xanthine,
(1-{2-[3-(2-oxo-imidazolidin-1-yl)-phenyl]-2-oxo-ethyl}-3-methyl-7-(3-methyl-2-buten-1-yl)-8-(3-amino-piperidin-1-yl)-xanthine,
(1-methyl-3-(2-propen-1-yl)-7-(2-cyano-benzyl)-8-(3-amino-piperidin-1-yl)-xanthine,
(1-(2-{2-[(ethylcarbonyl)amino]-phenyl}-2-oxo-ethyl)-3-methyl-7-(3-methyl-2-buten-1-yl)-8-(3-amino-piperidin-1-yl)-xanthine,
(1-methyl-3-phenyl-7-(2-cyano-benzyl)-8-(3-amino-piperidin-1-yl)-xanthine,
(1-[2-(2-amino-phenyl)-2-oxo-ethyl]-3-methyl-7-(3-methyl-2-buten-1-yl)-8-((S)-3-amino-piperidin-1-yl)-xanthine,
(1-(2-phenyl-2-oxo-ethyl)-3-cyanomethyl-7-(3-methyl-2-buten-1-yl)-8-(3-amino-piperidin-1-yl)-xanthine,
(1-[(quinolin-2-yl)methyl]-3-methyl-7-(3-methyl-2-buten-1-yl)-8-(3-amino-piperidin-1-yl)-xanthine,
(1-[(2-oxo-2H-chromen-4-yl)methyl]-3-methyl-7-(3-methyl-2-buten-1-yl)-8-(3-amino-piperidin-1-yl)-xanthine,
(1-[(cinnolin-4-yl)methyl]-3-methyl-7-(3-methyl-2-buten-1-yl)-8-(3-amino-piperidin-1-yl)-xanthine,
(1-[(1-methyl-2-oxo-1,2-dihydro-quinolin-4-yl)methyl]-3-methyl-7-(3-methyl-2-buten-1-yl)-8-(3-amino-piperidin-1-yl)-xanthine,
(1-[(4-oxo-3,4-dihydro-phthalazin-1-yl)methyl]-3-methyl-7-(3-methyl-2-buten-1-yl)-8-(3-amino-piperidin-1-yl)-xanthine,
(1-[(quinazolin-4-yl)methyl]-3-methyl-7-(3-methyl-2-buten-1-yl)-8-(3-amino-piperidin-1-yl)-xanthine,
(1-[(5-methyl-3-phenyl-isoxazol-4-yl)methyl]-3-methyl-7-(3-methyl-2-buten-1-yl)-8-(3-amino-piperidin-1-yl)-xanthine,
(1-[(isoquinolin-3-yl)methyl]-3-methyl-7-(3-methyl-2-buten-1-yl)-8-(3-amino-piperidin-1-yl)-xanthine,
(1-[(3-phenyl-[1,2,4]oxadiazol-5-yl)methyl]-3-methyl-7-(3-methyl-2-buten-1-yl)-8-(3-amino-piperidin-1-yl)-xanthine,
(1-[(4-phenyl-pyridin-2-yl)methyl]-3-methyl-7-(3-methyl-2-buten-1-yl)-8-(3-amino-piperidin-1-yl)-xanthine,
(1-[(5-phenyl-pyridin-2-yl)methyl]-3-methyl-7-(3-methyl-2-buten-1-yl)-8-(3-amino-piperidin-1-yl)-xanthine,
(1-[(3-methyl-4-oxo-3,4-dihydro-phthalazin-1-yl)methyl]-3-methyl-7-(3-methyl-2-buten-1-yl)-8-(3-amino-piperidin-1-yl)-xanthine,
(1-[2-(3-methylsulphanyl-phenyl)-2-oxo-ethyl]-3-methyl-7-(3-methyl-2-buten-1-yl)-8-(3-amino-piperidin-1-yl)-xanthine,
(1-[2-(3-methanesulphinyl-phenyl)-2-oxo-ethyl]-3-methyl-7-(3-methyl-2-buten-1-yl)-8-(3-amino-piperidin-1-yl)-xanthine,
(1-[2-(3-methanesulphonyl-phenyl)-2-oxo-ethyl]-3-methyl-7-(3-methyl-2-buten-1-yl)-8-(3-amino-piperidin-1-yl)-xanthine,
(1-[2-(3-carboxy-phenyl)-2-oxo-ethyl]-3-methyl-7-(3-methyl-2-buten-1-yl)-8-(3-amino-piperidin-1-yl)-xanthine,
(1-[2-(3-methoxycarbonyl-phenyl)-2-oxo-ethyl]-3-methyl-7-(3-methyl-2-buten-1-yl)-8-(3-amino-piperidin-1-yl)-xanthine,
(1-{2-[3-(methylaminocarbonyl)-phenyl]-2-oxo-ethyl}-3-methyl-7-(3-methyl-2-buten-1-yl)-8-(3-amino-piperidin-1-yl)-xanthine,
(1-{2-[3-(dimethylaminocarbonyl)-phenyl]-2-oxo-ethyl}-3-methyl-7-(3-methyl-2-buten-1-yl)-8-(3-amino-piperidin-1-yl)-xanthine,
(1-{2-[3-(morpholin-4-yl-carbonyl)-phenyl]-2-oxo-ethyl}-3-methyl-7-(3-methyl-2-buten-1-yl)-8-(3-amino-piperidin-1-yl)-xanthine,
(1-[2-(2-carboxy-phenyl)-2-oxo-ethyl]-3-methyl-7-(3-methyl-2-buten-1-yl)-8-(3-amino-piperidin-1-yl)-xanthine,
(1-[2-(2-ethoxycarbonyl-phenyl)-2-oxo-ethyl]-3-methyl-7-(3-methyl-2-buten-1-yl)-8-(3-amino-piperidin-1-yl)-xanthine,
(1-{2-[2-(di methylaminocarbonyl)-phenyl]-2-oxo-ethyl}-3-methyl-7-(3-methyl-2-buten-1-yl)-8-(3-amino-piperidin-1-yl)-xanthine,
(1-{2-[2-(morphol in-4-yl-carbonyl)-phenyl]-2-oxo-ethyl}-3-methyl-7-(3-methyl-2-buten-1-yl)-8-(3-amino-piperidin-1-yl)-xanthine,
(1-[2-(2,6-dimethoxy-phenyl)-2-oxo-ethyl]-3-methyl-7-(3-methyl-2-buten-1-yl)-8-(3-amino-piperidin-1-yl)-xanthine,
(1-((E)-3-phenyl-allyl)-3-methyl-7-(3-methyl-2-buten-1-yl)-8-(3-amino-piperidin-1-yl)-xanthine,
(1-[(benzo[b]thiophen-3-yl)methyl]-3-methyl-7-(3-methyl-2-buten-1-yl)-8-(3-amino-piperidin-1-yl)-xanthine,
(1-[(1H-indol-3-yl)methyl]-3-methyl-7-(3-methyl-2-buten-1-yl)-8-(3-amino-piperidin-1-yl)-xanthine,
(1-[(biphenyl-4-yl)methyl]-3-methyl-7-(3-methyl-2-buten-1-yl)-8-(3-amino-piperidin-1-yl)-xanthine,
(1-(2-cyclohexyl-2-oxo-ethyl)-3-methyl-7-(3-methyl-2-buten-1-yl)-8-(3-amino-piperidin-1-yl)-xanthine,
(1-(3,3-dimethyl-2-oxo-butyl)-3-methyl-7-(3-methyl-2-buten-1-yl)-8-(3-amino-piperidin-1-yl)-xanthine,
(1-({5-[(methoxycarbonyl)methylamino]-isoquinolin-1-yl}methyl)-3-methyl-7-(3-methyl-2-buten-1-yl)-8-(3-amino-piperidin-1-yl)-xanthine,
(1-(2-dimethylamino-2-oxo-ethyl)-3-methyl-7-(3-methyl-2-buten-1-yl)-8-(3-amino-piperidin-1-yl)-xanthine,
(1-[2-(piperidin-1-yl)-2-oxo-ethyl]-3-methyl-7-(3-methyl-2-buten-1-yl)-8-(3-amino-piperidin-1-yl)-xanthine, (1-[(2-methyl-1-oxo-1,2-dihydro-isoquinolin-4-yl)methyl]-7-(3-methyl-2-buten-1-yl)-8-(3-amino-piperidin-1-yl)-xanthine, (1-[2-(2,3-dimethoxy-phenyl)-2-oxo-ethyl]-3-methyl-7-(3-methyl-2-buten-1-yl)-8-(3-amino-piperidin-1-yl)-xanthine, (1-[2-(pyrrolidin-1-yl)-2-oxo-ethyl]-3-methyl-7-(3-methyl-2-buten-1-yl)-8-(3-amino-piperidin-1-yl)-xanthine, (1-[2-(2,3-dihydro-benzo[1,4]dioxin-5-yl)-2-oxo-ethyl]-3-methyl-7-(3-methyl-2-buten-1-yl)-8-(3-amino-piperidin-1-yl)-xanthine, (1-[2-(3-methyl-2-oxo-2,3-dihydro-benzooxazol-7-yl)-2-oxo-ethyl]-3-methyl-7-(3-methyl-2-buten-1-yl)-8-(3-amino-piperidin-1-yl)-xanthine, (1-[2-(benzo[1,3]dioxol-4-yl)-2-oxo-ethyl]-3-methyl-7-(3-methyl-2-buten-1-yl)-8-(3-amino-piperidin-1-yl)-xanthine, (1-methyl-3-isopropyl-7-(2-cyano-benzyl)-8-(3-amino-piperidin-1-yl)-xanthine, (1-[2-(2-cyanomethylamino-phenyl)-2-oxo-ethyl]-3-methyl-7-(3-methyl-2-buten-1-yl)-8-(3-amino-piperidin-1-yl)-xanthine, (1-[(isoquinolin-1-yl)methyl]-3-[(methoxycarbonyl)methyl]-7-(3-methyl-2-buten-1-yl)-8-(3-amino-piperidin-1-yl)-xanthine, (1-(2-{2-[(isopropyloxycarbonyl)methoxy]-phenyl}-2-oxo-ethyl)-3-methyl-7-(3-methyl-2-buten-1-yl)-8-(3-amino-piperidin-1-yl)-xanthine, (1-[2-(2-{[(ethoxycarbonylamino)carbonyl]amino}-phenyl)-2-oxo-ethyl]-3-methyl-7-(3-methyl-2-buten-1-yl)-8-(3-amino-piperidin-1-yl)-xanthine, (1-[2-(2-acetylamino-phenyl)-2-oxo-ethyl]-3-methyl-7-(3-methyl-2-buten-1-yl)-8-((S)-3-amino-piperidin-1-yl)-xanthine, (1-(2-{2-[(methylaminocarbonyl)methoxy]-phenyl}-2-oxo-ethyl)-3-methyl-7-(3-methyl-2-buten-1-yl)-8-((S)-3-amino-piperidin-1-yl)-xanthine, (1-methyl-7-(2-cyano-benzyl)-8-(3-amino-piperidin-1-yl)-xanthine, (1-(2-{2-[(isopropylcarbonyl)amino]-phenyl}-2-oxo-ethyl)-3-methyl-7-(3-methyl-2-buten-1-yl)-8-(3-amino-piperidin-1-yl)-xanthine, (1-(2-{2-[(methoxycarbonyl)amino]-phenyl}-2-oxo-ethyl)-3-methyl-7-(3-methyl-2-buten-1-yl)-8-(3-amino-piperidin-1-yl)-xanthine, (1-[2-(3-methyl-2-oxo-2,3-dihydro-benzooxazol-4-yl)-2-oxo-ethyl]-3-methyl-7-(3-methyl-2-buten-1-yl)-8-(3-amino-piperidin-1-yl)-xanthine, (1-[2-(2-nitro-3-methoxy-phenyl)-2-oxo-ethyl]-3-methyl-7-(3-methyl-2-buten-1-yl)-8-(3-amino-piperidin-1-yl)-xanthine, (1-[2-(2-amino-3-methoxy-phenyl)-2-oxo-ethyl]-3-methyl-7-(3-methyl-2-buten-1-yl)-8-(3-amino-piperidin-1-yl)-xanthine, (1-[2-(2-oxo-2,3-dihydro-benzooxazol-7-yl)-2-oxo-ethyl]-3-methyl-7-(3-methyl-2-buten-1-yl)-8-(3-amino-piperidin-1-yl)-xanthine, (1-[(3-methyl-isoquinolin-1-yl)methyl]-3-methyl-7-(3-methyl-1-buten-1-yl)-8-((R)-3-amino-piperidin-1-yl)-xanthine, (1-[(3-methyl-isoquinolin-1-yl)methyl]-3-methyl-7-(2-cyano-benzyl)-8-(3-amino-piperidin-1-yl)-xanthine, (1-[2-(3-carboxymethoxy-phenyl)-2-oxo-ethyl]-3-methyl-7-(3-methyl-2-buten-1-yl)-8-(3-amino-piperidin-1-yl)-xanthine and (1-[2-(2-carboxymethoxy-phenyl)-2-oxo-ethyl]-3-methyl-7-(3-methyl-2-buten-1-yl)-8-(3-amino-piperidin-1-yl)-xanthine, the tautomers, enantiomers, diastereomers, the mixtures thereof, the prodrugs thereof and the salts thereof.

A first preferred sub-group of the first object of the invention comprises compounds of general formula I wherein
$R^1$ denotes a 4-methoxy-1-naphthylmethyl group,
a 2-quinolinylmethyl, 4-quinolinylmethyl or a 6-quinolinylmethyl group, a 1-isoquinolinylmethyl, 3-methyl-1-isoquinolinylmethyl, 4-methyl-1-isoquinolinylmethyl or a 3-isoquinolinylmethyl group or
a 2-quinazolinylmethyl, 4-methyl-2-quinazolinylmethyl or a 4-quinazolinyl-methyl group,
$R^2$ denotes a methyl group and
$R^3$ denotes a 2-buten-1-yl or a 2-butyn-1-yl group,
the tautomers, enantiomers, diastereomers, the mixtures thereof and the salts thereof.

A second preferred sub-group of the first object of the invention comprises compounds of general formula I, wherein
$R^1$ denotes a [2-(methylcarbonylamino)-phenyl]-carbonylmethyl group,
a [2-(ethylcarbonylamino)-phenyl]-carbonylmethyl group or
a [2-(isopropylcarbonylamino)-phenyl]-carbonylmethyl group,
$R^2$ denotes a methyl group and
$R^3$ denotes a 2-buten-1-yl or a 2-butyn-1-yl group,
the tautomers, enantiomers, diastereomers, the mixtures thereof and the salts thereof.

A third preferred sub-group of the first object of the invention comprises compounds of general formula I according to claim 1, wherein
$R^1$ denotes a [2-(aminocarbonylmethoxy)-phenyl]-carbonylmethyl group,
[2-(methylaminocarbonylmethoxy)-phenyl]-carbonylmethyl group,
a [2-(ethylaminocarbonylmethoxy)-phenyl]-carbonylmethyl group or
a [2-(isopropylaminocarbonylmethoxy)-phenyl]-carbonylmethyl group,
$R^2$ denotes a methyl group and
$R^3$ denotes a 2-buten-1-yl group,
a 2-butyn-1-yl group or
a 1-cyclopenten-1-ylmethyl group,
the tautomers, enantiomers, diastereomers, the mixtures thereof and the salts thereof.

A second object of the invention relates to compounds of general formula I, wherein
$R^1$ denotes a methyl group which is substituted by a naphthyl, fluoronaphthyl, methylnaphthyl, methoxynaphthyl, (difluoromethoxy)-naphthyl, cyanonaphthyl, nitronaphthyl or (dimethylamino)-naphthyl group,
a methyl group which is substituted by a phenanthrenyl group,
a methyl group which is substituted by a 2-phenylethenyl, 2-[(trifluoromethyl)-phenyl]-ethenyl, 2-(nitrophenyl)ethenyl, 2-(pentafluorophenyl)ethenyl or a biphenylyl group,
a methyl group which is substituted by a phenyloxadiazolyl, phenylpyridinyl, indolyl, methylindolyl, dimethyl-6,7-dihydro-5H-[2]pyrindinyl, benzimidazolyl, methylbenzimidazolyl, (cyanoethyl)-benzimidazolyl, (methylaminocarbonylmethyl)benzimidazolyl, benzylbenzimidazolyl, benzofuranyl, acetylbenzofuranyl, cyanobenzofuranyl, benzoxazolyl, nitrobenzoxazolyl, benzothiophenyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenylisoquinolinyl, methoxyisoquinolinyl, methoxy-chloro-isoquinolinyl, methoxy-bromo-isoquinolinyl, (methoxycarbonylmethylamino)-isoquinolinyl, dimethyl-5,6,7,8-tetrahydroisoquinolinyl, 1,2,3,4-tetrahydro-phenanthridinyl, cinnolinyl, quinazolinyl, methylquinazolinyl, isopropylquinazolinyl, cyclopropylquinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, phenyl-oxyquinazolinyl, imidazo[1,2-a]pyridinyl, methylimidazo[1,2-a]pyridinyl, phenyl-imidazo[1,2-a]pyridinyl, benzylimidazo[1,2-a]pyridinyl, pyrazolo[1,5-a]pyridinyl, quinoxalinyl, methylquinoxalinyl, dimethylquinoxalinyl, trimethylquinoxalinyl, phenylquinoxalinyl, methylphthalazinyl, naphthyridinyl, 2,3-dihydrobenzo[1,4]-dioxinyl, 1,2-dihydro-2-oxo-quinolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group, a phenylcarbonylmethyl group, a phenylcarbonylmethyl group wherein the phenyl moiety is substituted by an amino, cyanomethylamino, (ethyloxycarbonylmethyl)amino, (methylaminocarbonyl)methylamino, methylcarbonylamino, ethylcarbonylamino, isopropylcarbonylamino, phenylcarbonylamino, methoxycarbonylamino, (ethyloxycarbonylamino)-carbonylamino or a 2-oxo-imidazolidin-1-yl group, a phenylcarbonylmethyl group wherein the phenyl moiety is substituted by a phenyl group, a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group, a phenylcarbonylmethyl group wherein the phenyl moiety is substituted by a methylsulphanyl, methylsulphinyl or methylsulphonyl group, a phenylcarbonylmethyl group wherein the phenyl moiety is substituted by a methoxy, difluoromethoxy, trifluoromethoxy, ethyloxy, isopropyloxy or phenyloxy group, a phenylcarbonylmethyl group wherein the phenyl moiety is substituted by a methylsulphinylmethoxy, carboxymethoxy, ethyloxycarbonylmethoxy, isopropyloxycarbonylmethoxy, aminocarbonylmethoxy, methylaminocarbonylmethoxy, ethylaminocarbonylmethoxy, isopropylaminocarbonylmethoxy, dimethylaminocarbonylmethoxy, pyrrolidin-1-ylcarbonylmethoxy or morpholin-4-ylcarbonylmethoxy group, a phenylcarbonylmethyl group wherein the phenyl moiety is substituted by a 1-(ethyloxycarbonyl)-1-methyl-ethyloxy, 1-(methoxycarbonyl)-ethyloxy or a 1-(aminocarbonyl)-ethyloxy group, a phenylcarbonylmethyl group wherein the phenyl moiety is substituted by two methoxy groups, a phenylcarbonylmethyl group wherein the phenyl moiety is substituted by a methoxy group and a nitro group, a phenylcarbonylmethyl group wherein the phenyl moiety is substituted by a methoxy group and an amino group, a phenylcarbonylmethyl group wherein in the phenyl moiety two adjacent hydrogen atoms are replaced by a —O—CH$_2$—O, —O—CF$_2$—O, —O—CH$_2$—CH$_2$—O, —NH—CO—NH, —N(CH$_3$)—CO—NH, —N(CH$_3$)—CO—N(CH$_3$), —NH—CO—O— or a —N(CH$_3$)—CO—O group, a (2-phenylethyl)carbonylmethyl group, a naphthylcarbonylmethyl, indolylcarbonylmethyl or quinolinylcarbonylmethyl group or a 2-cyanimino-2-phenyl-ethyl group, R$^2$ denotes a methyl, isopropyl, cyclopropyl, phenyl or fluorophenyl group and R$^3$ denotes a 2-methyl-2-propen-1-yl, 2-chloro-2-propen-1-yl or 3-bromo-2-propen-1-yl group a 1-buten-1-yl, 3-methyl-1-buten-1-yl, 2-buten-1-yl, 2-methyl-2-buten-1-ylor 2,3-dimethyl-2-buten-1-yl group, a 2-butyn-1-yl group, a 1-cyclopenten-1-ylmethyl group or a 2-furanylmethyl group, the tautomers, enantiomers, diastereomers, the mixtures thereof, the prodrugs thereof and the salts thereof.

A preferred sub-group of the second object of the invention comprises compounds of general formula I wherein R$^1$ and R$^2$ are as hereinbefore defined and R$^3$ denotes a 1-buten-1-yl, 2-buten-1-yl or 2-butyn-1-yl group, the tautomers, enantiomers, diastereomers, the mixtures thereof and the salts thereof.

A particularly preferred sub-group of the second object of the invention comprises compounds of general formula I wherein R$^1$ denotes a methyl group which is substituted by a naphthyl, fluoronaphthyl, methylnaphthyl, methoxynaphthyl, (difluoromethoxy)-naphthyl, cyanonaphthyl or nitronaphthyl group, a methyl group which is substituted by a 2-(pentafluorophenyl)ethenyl group, a methyl group which is substituted by a benzofuranyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenyl-isoquinolinyl, methoxyisoquinolinyl, 1,2,3,4-tetrahydrophenanthridinyl, quinazolinyl, methylquinazolinyl, isopropylquinazolinyl, cyclopropyl-quinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, quinoxalinyl, methylquinoxalinyl, dimethylquinoxalinyl, trimethylquinoxalinyl, phenylquinoxalinyl, [1,5]naphthyridinyl, [1,6]naphthyridinyl, [1,8]naphthyridinyl or a 1,2-dihydro-1-methyl-2-oxo-quinolinyl group, a phenylcarbonylmethyl group, a phenylcarbonylmethyl group wherein the phenyl moiety is substituted by a phenyl group, a phenylcarbonylmethyl group wherein the phenyl moiety is substituted by a methoxy, difluoromethoxy, trifluoromethoxy, ethyloxy, isopropyloxy or phenyloxy group, a phenylcarbonylmethyl group wherein in the phenyl moiety two adjacent hydrogen atoms are replaced by a —O—CH$_2$—O, —O—CF$_2$—O, —O—CH$_2$—CH$_2$—O, —N(CH$_3$)—CO—N(CH$_3$) or a —N(CH$_3$)—CO—O group, a naphthylcarbonylmethyl, indolylcarbonylmethyl or quinolinylcarbonylmethyl group or a 2-cyanimino-2-phenyl-ethyl group, R$^2$ denotes a methyl, isopropyl, cyclopropyl, phenyl or 4-fluorophenyl group and R$^3$ denotes a 1-buten-1-yl, 2-buten-1-yl or 2-butyn-1-yl group, the tautomers, enantiomers, diastereomers, the mixtures thereof and the salts thereof.

A second preferred sub-group of the second object of the invention comprises compounds of general formula I, wherein $R^1$ and $R^2$ are defined as immediately above and $R^3$ denotes a 1-buten-1-yl group, the tautomers, enantiomers, diastereomers, the mixtures thereof and the salts thereof.

A third preferred sub-group of the second object of the invention comprises compounds of general formula I wherein $R^1$ and $R^2$ are defined as immediately above and $R^3$ denotes a 2-buten-1-yl group, the tautomers, enantiomers, diastereomers, the mixtures thereof and the salts thereof.

A fourth preferred sub-group of the second object of the invention comprises compounds of general formula I wherein $R^1$ and $R^2$ are defined as immediately above and $R^3$ denotes a 2-butyn-1-yl group, the tautomers, enantiomers, diastereomers, the mixtures thereof and the salts thereof.

A third object of the invention relates to compounds of general formula I wherein $R^1$ denotes a methyl group which is substituted by a naphthyl, fluoronaphthyl, methylnaphthyl, methoxynaphthyl, (difluoromethoxy)-naphthyl, cyanonaphthyl or nitronaphthyl-group, a methyl group which is substituted by a 2-(pentafluorophenyl)ethenyl group, or a methyl group which is substituted by a benzofuranyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenyl-isoquinolinyl, methoxyisoquinolinyl, 1,2,3,4-tetrahydrophenanthridinyl, quinazolinyl, methylquinazolinyl, isopropylquinazolinyl, cyclopropyl-quinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, quinoxalinyl, methylquinoxalinyl, dimethylquinoxalinyl, trimethylquinoxalinyl, phenylquinoxalinyl, [1,5]naphthyridinyl, [1,6]naphthyridinyl, [1,8]naphthyridinyl or a 1,2-dihydro-1-methyl-2-oxo-quinolinyl group, $R^2$ denotes a methyl, isopropyl, cyclopropyl or phenyl group and $R^3$ denotes a 2-chlorobenzyl, 2-bromobenzyl, 2-ethynylbenzyl or 2-cyanobenzyl group, the tautomers, enantiomers, diastereomers, the mixtures thereof and the salts thereof.

A first preferred sub-group of the third object of the invention comprises compounds of general formula I wherein $R^1$ denotes a (3-methyl-isoquinolin-1-yl)methyl group, $R^2$ denotes a methyl group and $R^3$ denotes a 2-chlorobenzyl, 2-bromobenzyl, 2-ethynylbenzyl or 2-cyanobenzyl group, the tautomers, enantiomers, diastereomers, the mixtures thereof and the salts thereof.

A second preferred sub-group of the third object of the invention comprises compounds of general formula I wherein $R^1$ and $R^2$ are as hereinbefore defined and $R^3$ denotes a 2-chlorobenzyl group, the tautomers, enantiomers, diastereomers, the mixtures thereof and the salts thereof.

A third preferred sub-group of the third object of the invention comprises compounds of general formula I wherein $R^1$ and $R^2$ are as hereinbefore defined and $R^3$ denotes a 2-bromobenzyl group, the tautomers, enantiomers, diastereomers, the mixtures thereof and the salts thereof.

A fourth preferred sub-group of the third object of the invention comprises compounds of general formula I wherein $R^1$ and $R^2$ are as hereinbefore defined and $R^3$ denotes a 2-ethynylbenzyl group, the tautomers, enantiomers, diastereomers, the mixtures thereof and the salts thereof.

A fifth preferred sub-group of the third object of the invention comprises compounds of general formula I wherein $R^1$ and $R^2$ are as hereinbefore defined and $R^3$ denotes a 2-cyanobenzyl group, the tautomers, enantiomers, diastereomers, the mixtures thereof and the salts thereof.

Most particularly preferred are the following compounds of general formula I:

(1) 1-[(quinazolin-2-yl)methyl]-3-methyl-7-(2-butyn-1-yl)-8-((R)-3-amino-piperidin-1-yl)-xanthine, (2) 1-(2-{2-[(ethylaminocarbonyl)methoxy]-phenyl}-2-oxo-ethyl)-3-methyl-7-(2-butyn-1-yl)-8-((R)-3-amino-piperidin-1-yl)-xanthine, (3) 1-(2-{2-[(methylaminocarbonyl)methoxy]-phenyl}-2-oxo-ethyl)-3-methyl-7-(2-butyn-1-yl)-8-((R)-3-amino-piperidin-1-yl)-xanthine, (4) 1-(2-phenyl-2-oxo-ethyl)-3-methyl-7-((E)-2-buten-1-yl)-8-((R)-3-amino-piperidin-1-yl)-xanthine, (5) 1-[(3-methyl-isoquinolin-1-yl)methyl]-3-methyl-7-(2-butyn-1-yl)-8-((S)-3-amino-piperidin-1-yl)-xanthine, (6) 1-[(3-methyl-isoquinolin-1-yl)methyl]-3-methyl-7-(2-butyn-1-yl)-8-((R)-3-amino-piperidin-1-yl)-xanthine, (7) 1-[(4-methyl-isoquinolin-1-yl)methyl]-3-methyl-7-(2-butyn-1-yl)-8-((S)-3-amino-piperidin-1-yl)-xanthine, (8) 1-[(4-methyl-isoquinolin-1-yl)methyl]-3-methyl-7-(2-butyn-1-yl)-8-((R)-3-amino-piperidin-1-yl)-xanthine, (9) 1-[2-(2,3-di hydro-benzo[1,4]dioxin-5-yl)-2-oxo-ethyl]-3-methyl-7-(2-butyn-1-yl)-8-(3-(R)-amino-piperidin-1-yl)-xanthine,

(10) 1-[(4-methoxy-naphthalen-1-yl)methyl]-3-methyl-7-(2-butyn-1-yl)-8-((S)-3-amino-piperidin-1-yl)-xanthine,

(11) 1-[(4-methoxy-naphthalen-1-yl)methyl]-3-methyl-7-(2-butyn-1-yl)-8-((R)-3-amino-piperidin-1-yl)-xanthine,

(12) 1-[2-(benzo[1,3]dioxol-4-yl)-2-oxo-ethyl]-3-methyl-7-(2-butyn-1-yl)-8-((R)-3-amino-piperidin-1-yl)-xanthine,

(13) 1-[(4-methyl-quinazol in-2-yl)methyl]-3-methyl-7-(2-butyn-1-yl)-8-(3-(R)-amino-piperidin-1-yl)-xanthine,

(14) 1-(2-{2-[(isopropylcarbonyl)amino]-phenyl}-2-oxo-ethyl)-3-methyl-7-((E)-2-buten-1-yl)-8-((S)-3-amino-piperidin-1-yl)-xanthine,

(15) 1-(2-{2-[(methylaminocarbonyl)methoxy]-phenyl}-2-oxo-ethyl)-3-methyl-7-((E)-2-buten-1-yl)-8-((R)-3-amino-piperidin-1-yl)-xanthine,

(16) 1-(2-{2-[(methylaminocarbonyl)methoxy]-phenyl}-2-oxo-ethyl)-3-methyl-7-((E)-2-buten-1-yl)-8-((S)-3-amino-piperidin-1-yl)-xanthine,

(17) 1-(2-{2-[(isopropylcarbonyl)amino]-phenyl}-2-oxo-ethyl)-3-methyl-7-(2-butyn-1-yl)-8-((R)-3-amino-piperidin-1-yl)-xanthine,

(18) 1-(2-{2-[(isopropylcarbonyl)amino]-phenyl}-2-oxo-ethyl)-3-methyl-7-((E)-2-buten-1-yl)-8-((R)-3-amino-piperidin-1-yl)-xanthine,

(19) 1-[(4-cyano-naphthalen-1-yl)methyl]-3-methyl-7-(2-butyn-1-yl)-8-((R)-3-amino-piperidin-1-yl)-xanthine,

(20) 1-[(4-phenyl-quinazolin-2-yl)methyl]-3-methyl-7-(2-butyn-1-yl)-8-((R)-3-amino-piperidin-1-yl)-xanthine,

(21) 1-[(8-methyl-quinoxalin-6-yl)methyl]-3-methyl-7-(2-butyn-1-yl)-8-((R)-3-amino-piperidin-1-yl)-xanthine,

(22) 1-[(4-fluoro-naphthalen-1-yl)methyl]-3-methyl-7-(2-butyn-1-yl)-8-((R)-3-amino-piperidin-1-yl)-xanthine,

(23) 1-((E)-3-pentafluorophenyl-allyl)-3-methyl-7-(2-butyn-1-yl)-8-((R)-3-amino-piperidin-1-yl)-xanthine,

(24) 1-[(3-trifluoromethyl-isoquinolin-1-yl)methyl]-3-methyl-7-(2-butyn-1-yl)-8-((R)-3-amino-piperidin-1-yl)-xanthine,

(25) 1-[(3-difluoromethyl-isoquinolin-1-yl)methyl]-3-methyl-7-(2-butyn-1-yl)-8-((R)-3-amino-piperidin-1-yl)-xanthine,

(26) 1-[2-(biphenyl-2-yl)-2-oxo-ethyl]-3-methyl-7-(2-butyn-1-yl)-8-((R)-3-amino-piperidin-1-yl)-xanthine,

(27) 1-[(3-methyl-isoquinolin-1-yl)methyl]-3-cyclopropyl-7-(2-butyn-1-yl)-8-((R)-3-amino-piperidin-1-yl)-xanthine,

(28) 1-[2-(3-methoxy-phenyl)-2-oxo-ethyl]-3-methyl-7-(2-butyn-1-yl)-8-((R)-3-amino-piperidin-1-yl)-xanthine,

(29) 1-[(3-methyl-isoquinolin-1-yl)methyl]-3-methyl-7-(2-chloro-benzyl)-8-((R)-3-amino-piperidin-1-yl)-xanthine and

(30) 1-[(3-methyl-isoquinolin-1-yl)methyl]-3-methyl-7-(2-bromo-benzyl)-8-((R)-3-amino-piperidin-1-yl)-xanthine as well as the tautomers, enantiomers, diastereomers, the mixtures thereof and the salts thereof.

According to the invention the compounds of general formula I are obtained by methods known per se, for example by the following methods:

a) reacting a compound of general formula

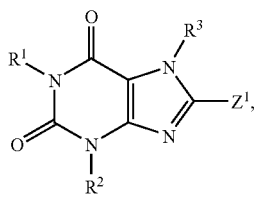

wherein
R$^1$ to R$^3$ are as hereinbefore defined and

Z$^1$ denotes a leaving group such as a halogen atom, a substituted hydroxy, mercapto, sulphinyl, sulphonyl or sulphonyloxy group such as a chlorine or bromine atom, a methanesulphonyl or methanesulphonyloxy group, with 3-aminopiperidine, the enantiomers thereof or the salts thereof.

The reaction is expediently carried out in a solvent such as isopropanol, butanol, tetrahydrofuran, dioxane, dimethylformamide, dimethylsulphoxide, ethyleneglycol monomethylether, ethyleneglycol diethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may, however, also be carried out without a solvent or in an excess of the 3-aminopiperidine.

b) deprotecting a compound of general formula

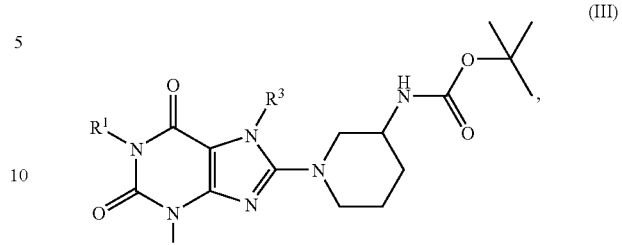

wherein R$^1$, R$^2$ and R$^3$ are as hereinbefore defined.

The tert.-butyloxycarbonyl group is preferably cleaved by treatment with an acid such as trifluoroacetic acid or hydrochloric acid or by treatment with bromotrimethylsilane or iodotrimethylsilane, optionally using a solvent such as methylene chloride, ethyl acetate, dioxane, methanol, isopropanol or diethyl ether at temperatures between 0 and 80° C.

c) In order to prepare a compound of general formula I wherein R$^1$ according to the definition provided hereinbefore contains a carboxy group:

deprotecting a compound of general formula

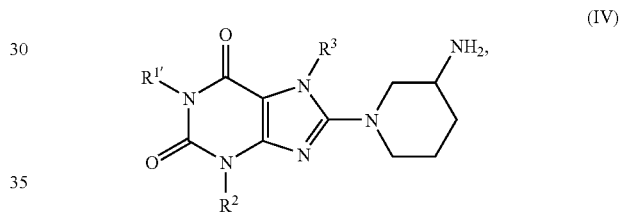

wherein R$^2$ and R$^3$ are as hereinbefore defined and R$^{1'}$ contains a carboxy group protected by a C$_{1-4}$-alkyl group.

The protecting group is cleaved by hydrolysis, for example, using an acid such as hydrochloric acid or sulphuric acid or an alkali metal hydroxide such as lithium hydroxide, sodium hydroxide or potassium hydroxide in a solvent such as methanol, ethanol, isopropanol, tetrahydrofuran or dioxane in the presence of water.

In the reactions described hereinbefore, any reactive groups present such as carboxy, amino, alkylamino or imino groups may be protected during the reaction by conventional protecting groups which are cleaved again after the reaction.

For example, a protecting group for a carboxy group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxan, methanol or diethylether.

A trifluoroacetyl group is preferably cleaved by treating with an acid such as hydrochloric acid, optionally in the presence of a solvent such as acetic acid at temperatures between 50 and 120° C., or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to IV used as starting materials are either known from the literature or may be obtained by methods known from the literature (cf. Examples I to LXXI).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows: The ability of the substances and their corresponding salts to inhibit the DPP-IV activity can be demonstrated in a test set-up in which an extract of human colon carcinoma cell line Caco-2 is used as the DPP-IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g of for 30 minutes at 4° C. (to remove cell debris).

The DPP-IV assay was carried out as follows:

50 μl substrate solution (AFC; AFC is amido-4-trifluoromethylcoumarin), final concentration 100 μM, were placed in black microtitre plates. 20 μl of assay buffer (final concentrations 50 mM Tris HCl pH 7.8, 50 mM NaCl, 1% DMSO) was pipetted in. The reaction was started by adding 30 μl of solubilised Caco-2 protein (final concentration 0.14 μg of protein per well). The test substances to be investigated were typically added prediluted in 20 μl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example no.) | DPP-IV inhibition $IC_{50}$ [nM] |
|---|---|
| 2(3) | 2160 |
| 2(9) | 264 |
| 2(12) | 16 |
| 2(17) | 32 |
| 2(20) | 12 |
| 2(25) | 4 |
| 2(27) | 9 |
| 2(35) | 5 |

-continued

| Compound (Example no.) | DPP-IV inhibition IC$_{50}$ [nM] |
| --- | --- |
| 2(37) | 5 |
| 2(43) | 6 |
| 2(51) | 6 |
| 2(52) | 9 |
| 2(59) | 250 |
| 2(66) | 22 |
| 2(80) | 1 |
| 2(86) | 2 |
| 2(96) | 2 |
| 2(99) | 1 |
| 2(100) | 3 |
| 2(108) | 3 |
| 2(129) | 3 |
| 2(130) | 3 |
| 2(131) | 3 |
| 2(132) | 1 |
| 2(135) | 3 |
| 2(137) | 13 |
| 2(138) | 8 |
| 2(139) | 4 |
| 2(142) | 1 |
| 2(145) | 4 |
| 2(148) | 1 |
| 2(150) | 1 |
| 2(151) | 3 |
| 2(152) | 4 |
| 2(185) | 3 |
| 2(217) | 4 |
| 2(247) | 2 |
| 2(251) | 12 |
| 2(256) | 8 |
| 2(260) | 13 |
| 2(264) | 6 |
| 2(277) | 6 |
| 2(280) | 5 |
| 2(285) | 3 |
| 2(287) | 11 |
| 2(288) | 14 |

The compounds prepared according to the invention are well tolerated, as for example when 10 mg/kg of the compound of Example 2(80) were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type 1 and type 2 diabetes mellitus, diabetic complications (such as e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also for favourably affecting catabolic states after operations or hormonal stress responses or reducing mortality or morbidity after myocardial infarct. They are also suitable for treating all conditions which are connected with the above mentioned effects and which are mediated by GLP-1 or GLP-2. The compounds according to the invention may also be used as diuretics or antihypertensives and are suitable for preventing and treating acute renal failure. Furthermore, the compounds according to the invention may be used to treat inflammatory diseases of the respiratory tract. They are also suitable for the prevention and treatment of chronic inflammatory intestinal diseases such as e.g. irritable bowel syndrome (IBS), Crohn's disease or ulcerative colitis and also pancreatitis. It is also likely that they can be used for all kinds of damage to or impairment of the gastrointestinal tract such as colitis and enteritis, for example. It is also expected that DPP-IV inhibitors and hence also the compounds according to the invention may be used to treat infertility or to improve fertility in humans or mammals, particularly when the infertility is connected with insulin resistance or polycystic ovary syndrome. On the other hand these substances are suitable for affecting sperm motility and can thus be used as male contraceptives. The substances are also suitable for treating deficiencies of growth hormone which are associated with reduced stature, and may also be used to advantage in any indications in which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based pancreatic carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Therapeutic agents which are suitable for such combinations include, for example, antidiabetics, such as metformin, sulphonylureas (e.g. glibenclamide, tolbutamide, glimepiride), nateglinide, repaglinide, thiazolidinedione (e.g. rosiglitazone, pioglitazone), PPAR-gamma agonists (e.g. GI 262570) and antagonists, PPAR-gamma/alpha modulators (e.g. KRP 297), alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, SGLT2 inhibitors such as T-1095, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol-pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol resorption inhibitors such as for example ezetimibe, bile acid-binding substances such as for example cholestyramine, inhibitors of ileac bile acid transport, HDL-raising compounds such as for example inhibitors of CETP or regulators of ABC1 or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $1_3$-agonists such as SB-418790 or AD-9677 as well as agonists of the 5HT2c receptor.

It is also possible to combine the compounds with drugs for treating high blood pressure such as e.g. AII antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I 1,3-dimethyl-7-(2,6-dicyano-benzyl)-8-bromo-xanthine

A mixture of 555 mg of 8-bromotheophyllin and 0.39 ml of Hünig base in 9 ml N,N-dimethylformamide is combined with 600 mg of 2-bromomethyl-isophthalonitrile and stirred overnight at ambient temperature. For working up the reaction mixture is poured onto water. The precipitate formed is suction filtered, washed with water and dried.

Yield: 686 mg (83% of theory)

$R_f$ value: 0.56 (silica gel, methylene chloride/methanol=95:5)

Mass spectrum (ESI$^+$): m/z=399, 401 [M+H]$^+$

The following compounds are obtained analogously to Example I:

(1) 3-methyl-7-(3-methyl-2-buten-1-yl)-8-chloro-xanthine
   Mass spectrum (ESI$^+$): m/z=269, 271 [M+H]$^+$
(2) 3-methyl-7-(2-cyano-benzyl)-8-chloro-xanthine
   Mass spectrum (ESI$^+$): m/z=316, 318 [M+H]$^+$
(3) 1-(2-phenyl-2-oxo-ethyl)-3-methyl-7-(2-butyn-1-yl)-8-bromo-xanthine
   Mass spectrum (ESI$^+$): m/z=415, 417 [M+H]$^+$
(4) 3-methyl-7-[(2-trimethylsilanyl-ethoxy)methyl]-8-bromo-xanthine
   (Carried out in the presence of potassium carbonate)
   Mass spectrum (ESI$^+$): m/z=375, 377 [M+H]$^+$
(5) 3-methyl-7-(3-methyl-2-buten-1-yl)-8-bromo-xanthine
   Mass spectrum (ESI$^+$): m/z=313, 315 [M+H]$^+$
(6) 3-methyl-7-(2,3-dimethyl-2-buten-1-yl)-8-bromo-xanthine
   $R_f$ value: 0.43 (silica gel, methylene chloride/methanol=9:1)
   Mass spectrum (ESI$^+$): m/z=327, 329 [M+H]$^+$
(7) 3-methyl-7-(2-butyn-1-yl)-8-bromo-xanthine
   $R_f$ value: 0.72 (silica gel, ethyl acetate)
   Mass spectrum (ESI$^+$): m/z=297/299 [M+H]$^+$
(8) 3-methyl-7-((E)-2-buten-1-yl)-8-bromo-xanthine
   (The product is contaminated with approx. 10-20% of Z compound)
   $R_f$ value: 0.55 (silica gel, cyclohexane/ethyl acetate/methanol=6:3:1)
   Mass spectrum (ESI$^+$): m/z=299, 301 [M+H]$^+$
(9) 3-methyl-7-[(1-cyclopenten-1-yl)methyl]-8-bromo-xanthine
   Mass spectrum (ESI$^+$): m/z=325, 327 [M+H]$^+$
(10) 1-(2-phenyl-2-oxo-ethyl)-3-methyl-7-[(1-cyclopenten-1-yl)methyl]-8-bromo-xanthine
   Mass spectrum (ESI$^+$): m/z=443, 445 [M+H]$^+$
(11) 1-(2-phenyl-2-oxo-ethyl)-3-methyl-7-((E)-2-buten-1-yl)-8-bromo-xanthine (product contains approx. 25% of Z isomer)
   Mass spectrum (ESI$^+$): m/z=417, 419 [M+H]$^+$
(12) 1-(2-phenyl-2-oxo-ethyl)-3-methyl-7-(2-methyl-allyl)-8-bromo-xanthine
   $R_f$ value: 0.71 (silica gel, methylene chloride/methanol=95:5)
   Mass spectrum (ESI$^+$): m/z=417, 419 [M+H]$^+$
(13) 1-(2-phenyl-2-oxo-ethyl)-3-methyl-7-(3-bromo-allyl)-8-bromo-xanthine
   $R_f$ value: 0.68 (silica gel, methylene chloride/methanol=95:5)
   Mass spectrum (ESI$^+$): m/z=481, 483, 485 [M+H]$^+$
(14) 1-(2-phenyl-2-oxo-ethyl)-3-methyl-7-[(furan-2-yl)methyl]-8-bromo-xanthine
   $R_f$ value: 0.60 (silica gel, methylene chloride/methanol=95:5)
   Mass spectrum (ESI$^+$): m/z=443, 445 [M+H]$^+$
(15) 1-(2-phenyl-2-oxo-ethyl)-3-methyl-7-(2-chloro-allyl)-8-bromo-xanthine
   $R_f$ value: 0.77 (silica gel, methylene chloride/methanol=95:5)
   Mass spectrum (ESI$^+$): m/z=437, 439, 441 [M+H]$^+$
(16) 1-(2-phenyl-2-oxo-ethyl)-3-methyl-7-((Z)-2-methyl-2-buten-1-yl)-8-bromo-xanthine
   $R_f$ value: 0.77 (silica gel, methylene chloride/methanol=95:5)
   Mass spectrum (ESI$^+$): m/z=431, 433 [M+H]$^+$
(17) 1-(2-phenyl-2-oxo-ethyl)-3-methyl-7-((E)-2-methyl-2-buten-1-yl)-8-bromo-xanthine
   $R_f$ value: 0.77 (silica gel, methylene chloride/methanol=95:5)
   Mass spectrum (ESI$^+$): m/z=431, 433 [M+H]$^+$
(18) 1-(2-phenyl-2-oxo-ethyl)-3-methyl-7-(1-phenylsulphanyl-butyl)-8-bromo-xanthine
   $R_f$ value: 0.83 (silica gel, methylene chloride/methanol=95:5)
   Mass spectrum (ESI$^+$): m/z=527, 529 [M+H]$^+$
(19) 3-methyl-7-(3-methyl-1-phenylsulphanyl-butyl)-8-bromo-xanthine
   (The [(1-chloro-3-methyl-butyl)sulphanyl]-benzene used as starting material for the reaction is obtained by chlorination of [(3-methyl-butyl)sulphanyl]-benzene with N-chlorosuccinimide in carbon tetrachloride)

R$_f$ value: 0.38 (silica gel, methylene chloride/methanol=95:5)
Mass spectrum (ESI$^+$): m/z=423, 425 [M+H]$^+$
(20) 1,3-dimethyl-7-(2-bromo-benzyl)-8-chloro-xanthine
R$_f$ value: 0.50 (silica gel, cyclohexane/ethyl acetate=1:1)
(21) 1,3-dimethyl-7-(2-chloro-benzyl)-8-chloro-xanthine
R$_f$ value: 0.50 (silica gel, cyclohexane/ethyl acetate=1:1)
(22) 3-cyclopropyl-7-(2-butyn-1-yl)-8-bromo-xanthine
R$_f$ value: 0.45 (ready-made reversed phase TLC plate (E. Merck), acetonitrile/water/trifluoroacetic acid=50:50:1)
Mass spectrum (ESI$^+$): m/z=223/225 [M+H]$^+$

EXAMPLE II (1-(2-{2-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
(63 mg of ethyl bromoacetate are added to a mixture of 200 mg of 1-[2-(2-hydroxy-phenyl)-2-oxo-ethyl]-3-methyl-7-(3-methyl-2-buten-1-yl)-8-[3-(tert.-butyloxycarbonylamino)-piperidin-1-yl]-xanthine and 63 mg of potassium carbonate in 3 ml N,N-dimethylformamide. The reaction mixture is stirred for five hours at ambient temperature. For working up it is combined with water and the precipitate formed is suction filtered, washed with water and dried for three hours at 80° C. in the drying cupboard.
Yield: 216 mg (94% of theory)
Mass spectrum (ESI$^+$): m/z=653 [M+H]$^+$
The following compounds are obtained analogously to Example II:
(1) 1-(2-{2-[(aminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=624 [M+H]$^+$
(2) 1-(2-{3-[(methylsulphanyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
R$_f$ value: 0.20 (silica gel, cyclohexane/ethyl acetate=6:4)
Mass spectrum (ESI$^+$): m/z=627 [M+H]$^+$
(3) 1-(2-{3-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
R$_f$ value: 0.50 (silica gel, cyclohexane/ethyl acetate=3:7)
(4) 1-(2-{2-[(methylaminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=638 [M+H]$^+$
(5) 1-(2-{2-[(di methylaminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=652 [M+H]$^+$
(6) 1-(2-{3-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=639 [M+H]$^+$
(7) 1-(2-{2-[(ethylaminocarbonyl)methoxy]-phenyl}-2-oxo-ethyl)-3-methyl-7-(2-butyn-1-yl)-8-[(R)-3-(tert.-butyloxycarbonylamino)-piperidin-1-yl]-xanthine
Mass spectrum (ESI$^+$): m/z=636 [M+H]$^+$
(8) 1-(2-{2-[(methylaminocarbonyl)methoxy]-phenyl}-2-oxo-ethyl)-3-methyl-7-[(1-cyclopenten-1-yl)methyl]-8-[3-(tert.-butyloxycarbonylamino)-piperidin-1-yl]-xanthine
Mass spectrum (ESI$^+$): m/z=650 [M+H]$^+$
(9) 1-(2-{2-[(methylaminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=622 [M+H]$^+$
(10) 1-(2-{2-[(aminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=608 [M+H]$^+$
(11) 1-(2-{2-[(methoxycarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=623 [M+H]$^+$
(12) 1-(2-{2-[(isopropyloxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=667 [M+H]$^+$
(13) 1-(2-{2-[(methylaminocarbonyl)methoxy]-phenyl}-2-oxo-ethyl)-3-methyl-7-(2-butyn-1-yl)-8-[(R)-3-(tert.-butyloxycarbonylamino)-piperidin-1-yl]-xanthine
Mass spectrum (ESI$^+$): m/z=622 [M+H]$^+$
(14) 1-(2-{2-[(methylaminocarbonyl)methoxy]-phenyl}-2-oxo-ethyl)-3-methyl-7-((E)-2-buten-1-yl)-8-[3-(tert.-butyloxycarbonylamino)-piperidin-1-yl]-xanthine (product contains some Z isomer)
R$_f$ value: 0.35 (silica gel, cyclohexane/ethyl acetate/methanol=5:4:1)
Mass spectrum (ESI$^+$): m/z=624 [M+H]$^+$
(15) 1-(2-{2-[(ethylaminocarbonyl)methoxy]-phenyl}-2-oxo-ethyl)-3-methyl-7-(2-butyn-1-yl)-8-[(S)-3-(tert.-butyloxycarbonylamino)-piperidin-1-yl]-xanthine
Mass spectrum (ESI$^+$): m/z=636 [M+H]$^+$
(16) 1-(2-{2-[(methylaminocarbonyl)methoxy]-phenyl}-2-oxo-ethyl)-3-methyl-7-(2-butyn-1-yl)-8-[(S)-3-(tert.-butyloxycarbonylamino)-piperidin-1-yl]-xanthine
Mass spectrum (ESI$^+$): m/z=622 [M+H]$^+$
(17) 1-(2-{2-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=639 [M+H]$^+$
(18) 1-(2-{2-[(methylaminocarbonyl)methoxy]-phenyl}-2-oxo-ethyl)-3-methyl-7-(3-methyl-2-buten-1-yl)-8-[(S)-3-(tert.-butyloxycarbonylamino)-piperidin-1-yl]-xanthine
Mass spectrum (ESI$^+$): m/z=638 [M+H]$^+$
(19) 2-(2-acetyl-phenoxy)-N-ethyl-acetamide
Mass spectrum (ESI$^+$): m/z=222 [M+H]$^+$
(20) 1-{2-[2-(1-methoxycarbonyl-ethoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=637 [M+H]$^+$
(21) 1-{2-[2-(1-aminocarbonyl-ethoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=622 [M+H]$^+$
(22) 2-(2-acetyl-phenoxy)-N-methyl-acetamide
Mass spectrum (ESI$^+$): m/z=208 [M+H]$^+$
(23) 1-{2-[2-(2-oxo-propoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=607 [M+H]$^+$
(24) 1-{2-[2-(1-ethoxycarbonyl-1-methyl-ethoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=665 [M+H]$^+$
(25) 1-{2-[2-cyanomethoxy-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=590 [M+H]$^+$
(26) 1-(2-{2-[(methylsulphanyl)methoxy]-phenyl}-2-oxo-ethyl)-3-methyl-7-(2-butyn-1-yl)-8-[3-(tert.-butyloxycarbonylamino)-piperidin-1-yl]-xanthine Mass spectrum (ESI⁺): m/z=611 [M+H]⁺

(27) 1-{[2-(tert.-butylcarbonyl)-benzofuran-3-yl]methyl}-3-methyl-7-(2-butyn-1-yl)-8-[3-(tert.-butyloxycarbonylamino)-piperidin-1-yl]-xanthine (Formed as main product when 1-[2-(2-hydroxy-phenyl)-2-oxo-ethyl]-3-methyl-7-(2-butyn-1-yl)-8-[3-(tert.-butyloxycarbonylamino)-piperidin-1-yl]-xanthine is reacted with 1-chloro-3,3-dimethyl-butan-2-one)
Mass spectrum (ESI⁺): m/z=631 [M+H]⁺

EXAMPLE III

1-[2-(2-hydroxy-phenyl)-2-oxo-ethyl]-3-methyl-7-(3-methyl-2-buten-1-yl)-8-[3-(tert.-butyloxycarbonylamino)-piperidin-1-yl]-xanthine 1.30 g of 3-tert.-butyloxycarbonylamino-piperidine are added to a mixture of 2.51 g of 1-[2-(2-hydroxy-phenyl)-2-oxo-ethyl]-3-methyl-7-(3-methyl-2-buten-1-yl)-8-chloro-xanthine and 880 mg of sodium carbonate in 8 ml of dimethylsulphoxide. The reaction mixture is stirred for 18 hours at 60° C. For working up it is combined with water and the precipitate formed is suction filtered. The solid crude product is dissolved in ethyl acetate, the solution is dried over magnesium sulphate and evaporated down. The flask residue is chromatographed through a silica gel column with cyclohexane/ethyl acetate
(10:1 to 1:1) as eluant.
Yield: 2.56 g (91% of theory)
Mass spectrum (ESI⁺): m/z=567 [M+H]⁺

The following compounds are obtained analogously to Example III:

(1) 3-methyl-7-(3-methyl-2-buten-1-yl)-8-[3-(tert.-butyloxycarbonylamino)-piperidin-1-yl]-xanthine
Mass spectrum (ESI⁺): m/z=433 [M+H]⁺

(2) 1-(1-methyl-2-oxo-2-phenyl-ethyl)-3-methyl-7-(3-methyl-2-buten-1-yl)-8-[3-(tert.-butyloxycarbonylamino)-piperidin-1-yl]-xanthine
Mass spectrum (ESI⁺): m/z=565 [M+H]⁺

(3) 3-methyl-7-(2-cyano-benzyl)-8-[3-(tert.-butyloxycarbonylamino)-piperidin-1-yl]-xanthine
$R_f$ value: 0.90 (silica gel, methylene chloride/methanol=9:1)
Mass spectrum (ESI⁻): m/z=478 [M-H]⁻

(4) 1-methyl-3-[(methoxycarbonyl)methyl]-7-(2-cyano-benzyl)-8-[3-(tert.-butyloxycarbonylamino)-piperidin-1-yl]-xanthine
Mass spectrum (ESI⁺): m/z=552 [M+H]⁺

(5) 1-methyl-3-cyanomethyl-7-(2-cyano-benzyl)-8-[3-(tert.-butyloxycarbonyl-amino)-piperidin-1-yl]-xanthine
Mass spectrum (ESI⁺): m/z=519 [M+H]⁺

(6) 1-methyl-3-(2-propyn-1-yl)-7-(2-cyano-benzyl)-8-[3-(tert.-butyloxycarbonyl-amino)-piperidin-1-yl]-xanthine
Mass spectrum (ESI⁺): m/z=518 [M+H]⁺

(7) 1-[2-(3-nitro-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.25 (silica gel, cyclohexane/ethyl acetate/methanol=7:2:1)
Mass spectrum (ESI⁺): m/z=596 [M+H]⁺

(8) 1-methyl-3-(2-propen-1-yl)-7-(2-cyano-benzyl)-8-[3-(tert.-butyloxycarbonyl-amino)-piperidin-1-yl]-xanthine
Mass spectrum (ESI⁺): m/z=520 [M+H]⁺

(9) 1-(2-phenyl-2-oxo-ethyl)-3-methyl-7-(2-butyn-1-yl)-8-[3-(tert.-butyloxycarbonylamino)-piperidin-1-yl]-xanthine
Mass spectrum (ESI⁺): m/z=535 [M+H]⁺

(10) 1-[2-(2-nitro-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.52 (silica gel, cyclohexane/ethyl acetate=3:7)
Mass spectrum (ESI⁺): m/z=596 [M+H]⁺

(11) 1-methyl-3-phenyl-7-(2-cyano-benzyl)-8-[3-(tert.-butyloxycarbonylamino)-piperidin-1-yl]-xanthine
Mass spectrum (ESI⁺): m/z=556 [M+H]⁺

(12) 1-[2-(2-nitro-phenyl)-2-oxo-ethyl]-3-methyl-7-(3-methyl-2-buten-1-yl)-8-[(S)-3-(tert.-butyloxycarbonylamino)-piperidin-1-yl]-xanthine
Mass spectrum (ESI⁺): m/z=596 [M+H]⁺

(13) 1-[(cinnolin-4-yl)methyl]-3-methyl-7-(3-methyl-2-buten-1-yl)-8-[3-(tert.-butyloxycarbonylamino)-piperidin-1-yl]-xanthine mixed with 1-[(1,4-dihydro-cinnolin-4-yl)methyl]-3-methyl-7-(3-methyl-2-buten-1-yl)-8-[3-(tert.-butyloxycarbonylamino)-piperidin-1-yl]-xanthine
$R_f$ value: 0.62 (silica gel, ethyl acetate)

(14) 1-({4-oxo-3-[(2-trimethylsilanyl-ethoxy)methyl]-3,4-dihydro-phthalazin-1-yl}methyl)-3-methyl-7-(3-methyl-2-buten-1-yl)-8-[3-(tert.-butyloxycarbonylamino)-piperidin-1-yl]-xanthine
(Carried out with potassium carbonate in the presence of Hünig base)
$R_f$ value: 0.27 (silica gel, cyclohexane/ethyl acetate=1:1)
Mass spectrum (ESI⁺): m/z=720 [M+H]⁺

(15) 1-[(isoquinolin-3-yl)methyl]-3-methyl-7-(3-methyl-2-buten-1-yl)-8-[3-(tert.-butyloxycarbonylamino)-piperidin-1-yl]-xanthine
$R_f$ value: 0.31 (silica gel, ethyl acetate/petroleum ether=7:3)
Mass spectrum (ESI⁺): m/z=574 [M+H]⁺

(16) 1-[(3-methyl-4-oxo-3,4-dihydro-phthalazin-1-yl)methyl]-3-methyl-7-(3-methyl-2-buten-1-yl)-8-[3-(tert.-butyloxycarbonylamino)-piperidin-1-yl]-xanthine
$R_f$ value: 0.45 (silica gel, methylene chloride/methanol/conc. aqueous ammonia=95:5)
Mass spectrum (ESI⁺): m/z=605 [M+H]⁺

(17) 3-methyl-7-(2,3-dimethyl-2-buten-1-yl)-8-[3-(tert.-butyloxycarbonylamino)-piperidin-1-yl]-xanthine
(Carried out with potassium carbonate)
$R_f$ value: 0.42 (silica gel, methylene chloride/methanol=20:1)
Mass spectrum (ESI⁺): m/z=447 [M+H]⁺

(18) 3-methyl-7-(2-butyn-1-yl)-8-[3-(tert.-butyloxycarbonylamino)-piperidin-1-yl]-xanthine
(Carried out with potassium carbonate)
Melting point: 235-237° C.
Mass spectrum (ESI⁺): m/z=417 [M+H]⁺

(19) 1-[(quinolin-4-yl)methyl]-3-methyl-7-(2-butyn-1-yl)-8-[3-(tert.-butyloxycarbonylamino)-piperidin-1-yl]-xanthine
(Carried out with potassium carbonate)
$R_f$ value: 0.36 (silica gel, ethyl acetate)
Mass spectrum (ESI⁺): m/z=558 [M+H]⁺

(20) 1-[(isoquinolin-1-yl)methyl]-3-methyl-7-(2-butyn-1-yl)-8-[3-(tert.-butyloxycarbonylamino)-piperidin-1-yl]-xanthine
(Carried out with potassium carbonate)
$R_f$ value: 0.71 (silica gel, ethyl acetate)
Mass spectrum (ESI⁺): m/z=558 [M+H]⁺

(21) 1-[(isoquinolin-1-yl)methyl]-3-methyl-7-((E)-2-buten-1-yl)-8-[3-(tert.-butyloxycarbonylamino)-piperidin-1-yl]-xanthine
(Carried out with potassium carbonate; the product contains approx. 20% of Z isomer)

$R_f$ value: 0.24 (silica gel, ethyl acetate/petroleum ether=1:1)
Mass spectrum (ESI⁺): m/z=560 [M+H]⁺

(22) 3-methyl-7-(2-butyn-1-yl)-8-[(R)-3-(tert.-butyloxycarbonylamino)-piperidin-1-yl]-xanthine
(Carried out with potassium carbonate)
$R_f$ value: 0.64 (silica gel, ethyl acetate)
Mass spectrum (ESI⁺): m/z=417 [M+H]⁺

(23) 3-methyl-7-(2-butyn-1-yl)-8-[(S)-3-(tert.-butyloxycarbonylamino)-piperidin-1-yl]-xanthine
(Carried out with potassium carbonate)
$R_f$ value: 0.64 (silica gel, ethyl acetate)
Mass spectrum (ESI⁺): m/z=417 [M+H]⁺

(24) 3-methyl-7-((E)-2-buten-1-yl)-8-[(S)-3-(tert.-butyloxycarbonylamino)-piperidin-1-yl]-xanthine
(product contains approx. 15% of Z isomer)
$R_f$ value: 0.35 (silica gel, cyclohexane/ethyl acetate=3:7)
Mass spectrum (ESI⁺): m/z=419 [M+H]⁺

(25) 3-methyl-7-((E)-2-buten-1-yl)-8-[(R)-3-(tert.-butyloxycarbonylamino)-piperidin-1-yl]-xanthine
(product contains approx. 15% of Z isomer)
$R_f$ value: 0.35 (silica gel, cyclohexane/ethyl acetate=3:7)
Mass spectrum (ESI⁺): m/z=419 [M+H]⁺

(26) 1-[2-(2-hydroxy-phenyl)-2-oxo-ethyl]-3-methyl-7-(2-butyn-1-yl)-8-[(R)-3-(tert.-butyloxycarbonylamino)-piperidin-1-yl]-xanthine
Mass spectrum (ESI⁺): m/z=551 [M+H]⁺

(27) 1-[2-(2-amino-phenyl)-2-oxo-ethyl]-3-methyl-7-[(1-cyclopenten-1-yl)methyl]-8-[3-(tert.-butyloxycarbonylamino)-piperidin-1-yl]-xanthine
Mass spectrum (ESI⁺): m/z=578 [M+H]⁺

(28) 1-(2-phenyl-2-oxo-ethyl)-3-methyl-7-[(1-cyclopenten-1-yl)methyl]-8-[3-(tert.-butyloxycarbonylamino)-piperidin-1-yl]-xanthine
Mass spectrum (ESI⁺): m/z=563 [M+H]⁺

(29) 1-[2-(2-hydroxy-phenyl)-2-oxo-ethyl]-3-methyl-7-[(1-cyclopenten-1-yl)methyl]-8-[3-(tert.-butyloxycarbonylamino)-piperidin-1-yl]-xanthine
Mass spectrum (ESI⁺): m/z=579 [M+H]⁺

(30) 1-methyl-3-isopropyl-7-(2-cyano-benzyl)-8-[3-(tert.-butyloxycarbonylamino)-piperidin-1-yl]-xanthine
Mass spectrum (ESI⁺): m/z=522 [M+H]⁺

(31) 1-[2-(2-hydroxy-phenyl)-2-oxo-ethyl]-3-methyl-7-(2-butyn-1-yl)-8-[3-(tert.-butyloxycarbonylamino)-piperidin-1-yl]-xanthine
Mass spectrum (ESI⁺): m/z=551 [M+H]⁺

(32) 1-[2-(2-amino-phenyl)-2-oxo-ethyl]-3-methyl-7-((E)-2-buten-1-yl)-8-[3-(tert.-butyloxycarbonylamino)-piperidin-1-yl]-xanthine (product contains approx. 10% of Z isomer)
$R_f$ value: 0.20 (silica gel, cyclohexane/ethyl acetate=1:1)
Mass spectrum (ESI⁺): m/z=552 [M+H]⁺

(33) 1-(2-phenyl-2-oxo-ethyl)-3-methyl-7-((E)-2-buten-1-yl)-8-[3-(tert.-butyloxy-carbonylamino)-piperidin-1-yl]-xanthine
(product contains approx. 25% of Z isomer)
Mass spectrum (ESI⁺): m/z=537 [M+H]⁺

(34) 1-[2-(2-hydroxy-phenyl)-2-oxo-ethyl]-3-methyl-7-(2-butyn-1-yl)-8-[(R)-3-(tert.-butyloxycarbonylamino)-piperidin-1-yl]-xanthine

(35) 1-[2-(2-hydroxy-phenyl)-2-oxo-ethyl]-3-methyl-7-((E)-2-buten-1-yl)-8-[3-(tert.-butyloxycarbonylamino)-piperidin-1-yl]-xanthine
(product contains some Z isomer)
$R_f$ value: 0.30 (silica gel, cyclohexane/ethyl acetate=4:6)
Mass spectrum (ESI⁺): m/z=553 [M+H]⁺

(36) 1-[2-(2-hydroxy-phenyl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI⁺): m/z=551 [M+H]⁺

(37) 1-[2-(2-amino-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.50 (silica gel, methylene chloride/methanol=95:5)
Mass spectrum (ESI⁺): m/z=550 [M+H]⁺

(38) 1-[2-(2-hydroxy-phenyl)-2-oxo-ethyl]-3-methyl-7-(3-methyl-2-buten-1-yl)-8-[(S)-3-(tert.-butyloxycarbonylamino)-piperidin-1-yl]-xanthine
Mass spectrum (ESI⁺): m/z=567 [M+H]⁺

(39) 1-(2-phenyl-2-oxo-ethyl)-3-methyl-7-(2-butyn-1-yl)-8-[(R)-3-(tert.-butyloxy-carbonylamino)-piperidin-1-yl]-xanthine
Mass spectrum (ESI⁺): m/z=535 [M+H]⁺

(40) 1-methyl-3-[(2-trimethylsilanyl-ethoxy)methyl]-7-(2-cyano-benzyl)-8-[3-(tert.-butyloxycarbonylamino)-piperidin-1-yl]-xanthine
Mass spectrum (ESI⁺): m/z=610 [M+H]⁺

(41) 3-methyl-7-(2-butyn-1-yl)-8-[(S)-3-(tert.-butyloxycarbonylamino)-piperidin-1-yl]-xanthine
(Carried out with potassium carbonate)
$R_f$ value: 0.52 (silica gel, ethyl acetate)
Mass spectrum (ESI⁺): m/z=417 [M+H]⁺

(42) 1-(2-phenyl-2-oxo-ethyl)-3-methyl-7-(2-methyl-allyl)-8-[3-(tert.-butyloxycarbonylamino)-piperidin-1-yl]-xanthine
$R_f$ value: 0.46 (silica gel, methylene chloride/methanol=95:5)

(43) 1-(2-phenyl-2-oxo-ethyl)-3-methyl-7-(3-bromo-allyl)-8-[3-(tert.-butyloxycarbonylamino)-piperidin-1-yl]-xanthine
$R_f$ value: 0.22 (silica gel, methylene chloride/methanol=95:5)
Mass spectrum (ESI⁺): m/z=601, 603 [M+H]⁺

(44) 1-(2-phenyl-2-oxo-ethyl)-3-methyl-7-[(furan-2-yl)methyl]-8-[3-(tert.-butyloxycarbonylamino)-piperidin-1-yl]-xanthine
$R_f$ value: 0.41 (silica gel, methylene chloride/methanol=95:5)

(45) 1-(2-phenyl-2-oxo-ethyl)-3-methyl-7-(2-chloro-allyl)-8-[3-(tert.-butyloxycarbonylamino)-piperidin-1-yl]-xanthine
$R_f$ value: 0.49 (silica gel, methylene chloride/methanol=95:5)
Mass spectrum (ESI⁺): m/z=557, 559 [M+H]⁺

(46) 1-(2-phenyl-2-oxo-ethyl)-3-methyl-7-(2-butyn-1-yl)-8-[(S)-3-(tert.-butyloxy-carbonylamino)-piperidin-1-yl]-xanthine
Mass spectrum (ESI⁺): m/z=535 [M+H]⁺

(47) 1-[2-(2-amino-phenyl)-2-oxo-ethyl]-3-methyl-7-((E)-2-buten-1-yl)-8-[(S)-3-(tert.-butyloxycarbonylamino)-piperidin-1-yl]-xanthine
$R_f$ value: 0.40 (silica gel, cyclohexane/ethyl acetate=4:6)
Mass spectrum (ESI⁺): m/z=552 [M+H]⁺

(48) 1-[2-(2-nitro-phenyl)-2-oxo-ethyl]-3-methyl-7-((E)-2-buten-1-yl)-8-[(R)-3-(tert.-butyloxycarbonylamino)-piperidin-1-yl]-xanthine
$R_f$ value: 0.50 (silica gel, cyclohexane/ethyl acetate=1:2)

(49) 1-[2-(2-nitro-phenyl)-2-oxo-ethyl]-3-methyl-7-((E)-2-buten-1-yl)-8-[(S)-3-(tert.-butyloxycarbonylamino)-piperidin-1-yl]-xanthine
Mass spectrum (ESI⁺): m/z=582 [M+H]⁺

(50) 1-[2-(2-nitro-3-methoxy-phenyl)-2-oxo-ethyl]-3-methyl-7-(3-methyl-2-buten-1-yl)-8-[3-(tert.-butyloxycarbonylamino)-piperidin-1-yl]-xanthine
Mass spectrum (ESI$^+$): m/z=626 [M+H]$^+$

(51) 1-(2-{2-oxo-3-[(2-trimethylsilanyl-ethoxy)methyl]-2,3-dihydro-benzooxazol-7-yl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=738 [M+H]$^+$

(52) 1-(2-phenyl-2-oxo-ethyl)-3-methyl-7-((Z)-2-methyl-2-buten-1-yl)-8-[3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=551 [M+H]$^+$

(53) 1-(2-phenyl-2-oxo-ethyl)-3-methyl-7-((E)-2-methyl-2-buten-1-yl)-8-[3-(tert.-butyloxycarbonylamino)-piperidin-1-yl]-xanthine
Mass spectrum (ESI$^+$): m/z=551 [M+H]$^+$

(54) 1-(2-{2-oxo-3-[(2-trimethylsilanyl-ethoxy)methyl]-2,3-dihydro-benzooxazol-4-yl}-2-oxo-ethyl)-3-methyl-7-(2-butyn-1-yl)-8-[3-(tert.-butyloxycarbonylamino)-piperidin-1-yl]-xanthine
$R_f$ value: 0.40 (silica gel, petroleum ether/ethyl acetate=1:1)
Mass spectrum (ESI$^+$): m/z=722 [M+H]$^+$

(55) 1-[2-(2,2-difluoro-benzo[1,3]dioxol-4-yl)-2-oxo-ethyl]-3-methyl-7-(2-butyn-1-yl)-8-[(R)-3-(tert.-butyloxycarbonylamino)-piperidin-1-yl]-xanthine
Mass spectrum (ESI$^+$): m/z=615 [M+H]$^+$

(56) 1-[2-(2,2-difluoro-benzo[1,3]dioxol-4-yl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI$^+$): m/z=615 [M+H]$^+$

(57) 1-[(1-methyl-1H-indol-2-yl)methyl]-3-methyl-7-(2-butyn-1-yl)-8-[3-(tert.-butyloxy-carbonylamino)-piperidin-1-yl]-xanthine
$R_f$ value: 0.80 (silica gel, methylene chloride/methanol=95:5)
Mass spectrum (ESI$^+$): m/z=560 [M+H]$^+$

(58) 1-[(quinolin-3-yl)methyl]-3-methyl-7-(2-butyn-1-yl)-8-[3-(tert.-butyloxycarbonyl-amino)-piperidin-1-yl]-xanthine
$R_f$ value: 0.50 (silica gel, ethyl acetate)
Mass spectrum (ESI$^+$): m/z=558 [M+H]$^+$

(59) 1-{[1-(tert.-butyloxycarbonylamino)-1H-indol-2-yl]methyl}-3-methyl-7-(2-butyn-1-yl)-8-[3-(tert.-butyloxycarbonylamino)-piperidin-1-yl]-xanthine
$R_f$ value: 0.40 (silica gel, petroleum ether/ethyl acetate=1:1)
Mass spectrum (ESI$^+$): m/z=646 [M+H]$^+$

(60) 1-[(2-methyl-1-[(2-tri methylsilanyl-ethoxy)methyl]-1H-benzoimidazol-5-yl)methyl]-3-methyl-7-(2-butyn-1-yl)-8-[3-(tert.-butyloxycarbonylamino)-piperidin-1-yl]-xanthine (mixed with 1-[(2-methyl-3-[(2-trimethylsilanyl-ethoxy)methyl]-3H-benzoimidazol-5-yl)methyl]-3-methyl-7-(2-butyn-1-yl)-8-[3-(tert.-butyloxycarbonylamino)-piperidin-1-yl]-xanthine)
$R_f$ value: 0.15 (silica gel, ethyl acetate)
Mass spectrum (ESI$^+$): m/z=691 [M+H]$^+$

(61) 1-[2-(quinolin-8-yl-]-2-oxo-ethyl]-3-methyl-7-(2-butyn-1-yl)-8-[3-(tert.-butyloxy-carbonylamino)-piperidin-1-yl]-xanthine
$R_f$ value: 0.35 (silica gel, methylene chloride/methanol=95:5)
Mass spectrum (ESI$^+$): m/z=586 [M+H]$^+$

(62) 1-[(1-[(2-trimethylsilanyl-ethoxy)methyl]-1H-benzoimidazol-5-yl)methyl]-3-methyl-7-(2-butyn-1-yl)-8-[3-(tert.-butyloxycarbonylamino)-piperidin-1-yl]-xanthine (mixed with 1-[(3-[(2-tri methylsilanyl-ethoxy)methyl]-3H-benzoimidazol-5-yl)methyl]-3-methyl-7-(2-butyn-1-yl)-8-[3-(tert.-butyloxycarbonylamino)-piperidin-1-yl]-xanthine)
$R_f$ value: 0.23 (silica gel, ethyl acetate)
Mass spectrum (ESI$^+$): m/z=677 [M+H]$^+$

(63) 1-[(pyrazolo[1,5-a]pyridin-2-yl)methyl]-3-methyl-7-(2-butyn-1-yl)-8-[3-(tert.-butyloxycarbonylamino)-piperidin-1-yl]-xanthine
$R_f$ value: 0.46 (silica gel, methylene chloride/methanol=95:5)
Mass spectrum (ESI$^+$): m/z=547 [M+H]$^+$

(64) 1-(2-phenyl-2-oxo-ethyl)-3-methyl-7-((E)-1-buten-1-yl)-8-[3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=537 [M+H]$^+$

(65) 1-{2-[1-(tert.-butyloxycarbonyl)-1H-indol-7-yl]-2-oxo-ethyl}-3-methyl-7-(2-butyn-1-yl)-8-[3-(tert.-butyloxycarbonylamino)-piperidin-1-yl]-xanthine
$R_f$ value: 0.38 (silica gel, petroleum ether/ethyl acetate=1:1)

(66) 1-[(3-methyl-isoquinolin-1-yl)methyl]-3-methyl-7-(3-methyl-1-buten-1-yl)-8-[(R)-3-(tert.-butyloxycarbonylamino)-piperidin-1-yl]-xanthine
$R_f$ value: 0.40 (silica gel, methylene chloride/methanol=95:5)
Mass spectrum (ESI$^+$): m/z=588 [M+H]$^+$

(67) 1,3-dimethyl-7-(2-bromo-benzyl)-8-[3-(tert.-butyloxycarbonylamino)-piperidin-1-yl]-xanthine
$R_f$ value: 0.40 (silica gel, cyclohexane/ethyl acetate=1:1)

(68) 1,3-dimethyl-7-(2-chloro-benzyl)-8-[3-(tert.-butyloxycarbonylamino)-piperidin-1-yl]-xanthine
$R_f$ value: 0.42 (silica gel, cyclohexane/ethyl acetate=1:1)

(69) 1-[(3-methyl-isoquinolin-1-yl)methyl]-3-methyl-7-(2-cyano-benzyl)-8-[3-(tert.-butyloxycarbonylamino)-piperidin-1-yl]-xanthine
Mass spectrum (ESI$^+$): m/z=635 [M+H]$^+$
$R_f$ value: 0.40 (silica gel, cyclohexane/ethyl acetate=3:7)

(70) 3-cyclopropyl-7-(2-butyn-1-yl)-8-[3-(tert.-butyloxycarbonylamino)-piperidin-1-yl]-xanthine
Mass spectrum (ESI$^+$): m/z=443 [M+H]$^+$
$R_f$ value: 0.70 (silica gel, ethyl acetate)

(71) 3-cyclopropyl-7-(2-butyn-1-yl)-8-[(R)-3-(tert.-butyloxycarbonylamino)-piperidin-1-yl]-xanthine
$R_f$ value: 0.35 (ready-made reversed phase TLC plate (E. Merck), acetonitrile/water/trifluoroacetic acid=50:50:1)
Mass spectrum (ESI$^+$): m/z=443 [M+H]$^+$

(72) 1-[(3-methyl-isoquinolin-1-yl)methyl]-3-methyl-7-(2-chloro-benzyl)-8-[(R)-3-(tert.-butyloxycarbonylamino)-piperidin-1-yl]-xanthine
Mass spectrum (ESI$^+$): m/z=644, 646 [M+H]$^+$
$R_f$ value: 0.39 (silica gel, cyclohexane/ethyl acetate=1:1)

(73) 1-[(3-methyl-isoquinolin-1-yl)methyl]-3-methyl-7-(2-bromo-benzyl)-8-[(R)-3-(tert.-butyloxycarbonylamino)-piperidin-1-yl]-xanthine
Mass spectrum (ESI$^+$): m/z=644, 646 [M+H]$^+$

(74) 1-[(4-methyl-quinazol in-2-yl)methyl]-3-methyl-7-(2-chloro-benzyl)-8-[(R)-3-(tert.-butyloxycarbonylamino)-piperidin-1-yl]-xanthine Prepared by reacting (4-methyl-quinazolin-2-yl)-methyl-chloride and 3-methyl-7-(2-chlorobenzyl)-8-bromo-xanthine and subsequently reacting with (R)-3-(tert.-butyloxycarbonylamino)-piperidine Mass spectrum (ESI+): m/z=645, 647 [M+H]+

(75) 1-[(4-phenyl-quinazolin-2-yl)methyl]-3-methyl-7-(2-chloro-benzyl)-8-[(R)-3-(tert.-butyloxycarbonylamino)-piperidin-1-yl]-xanthine Prepared by reacting (4-phenyl-quinazolin-2-yl)-methyl-chloride and 3-methyl-7-(2-chlorobenzyl)-8-bromo-xanthine and subsequently reacting with (R)-3-(tert.-butyloxycarbonylamino)-piperidine Mass spectrum (ESI+): m/z=707, 709 [M+H]+

EXAMPLE IV

1-[2-(2-hydroxy-phenyl)-2-oxo-ethyl]-3-methyl-7-(3-methyl-2-buten-1-yl)-8-chloro-xanthine Prepared by treating 1-[2-(2-methoxy-phenyl)-2-oxo-ethyl]-3-methyl-7-(3-methyl-2-buten-1-yl)-8-chloro-xanthine with boron tribromide in methylene chloride. The desired product is contaminated with approx. 20% 1-[2-(2-hydroxy-phenyl)-2-oxo-ethyl]-3-methyl-7-(3-bromo-3-methyl-butyl)-8-chloro-xanthine.

Mass spectrum (ESI+): m/z=403, 405 [M+H]+

The following compounds are obtained analogously to Example IV:

(1) 1-[2-(2-hydroxy-phenyl)-2-oxo-ethyl]-3-methyl-7-(2-butyn-1-yl)-8-bromo-xanthine (product is contaminated with approx. 20% 1-[2-(2-hydroxy-phenyl)-2-oxo-ethyl]-3-methyl-7-(3-bromo-2-buten-1-yl)-8-bromo-xanthine)

Mass spectrum (ESI+): m/z=431, 433 [M+H]+

(2) 1-[2-(2-hydroxy-phenyl)-2-oxo-ethyl]-3-methyl-7-[(1-cyclopenten-1-yl)methyl]-8-bromo-xanthine Mass spectrum (ESI+): m/z=459, 461 [M+H]+

(3) 1-[2-(2-hydroxy-phenyl)-2-oxo-ethyl]-3-methyl-7-((E)-2-buten-1-yl)-8-bromo-xanthine (product contains some Z isomer)

$R_f$ value: 0.60 (silica gel, cyclohexane/ethyl acetate=4:6)

Mass spectrum (ESI+): m/z=433, 435 [M+H]+

(4) 1-[2-(2-hydroxy-phenyl)-2-oxo-ethyl]-3-methyl-7-(3-methyl-2-buten-1-yl)-8-bromo-xanthine Mass spectrum (ESI+): m/z=447, 449 [M+H]+

EXAMPLE V

1-[2-(2-methoxy-phenyl)-2-oxo-ethyl]-3-methyl-7-(3-methyl-2-buten-1-yl)-8-chloro-xanthine 1.71 g of 2-bromo-1-(2-methoxy-phenyl)-ethanone are added to a mixture of 2.00 g of 3-methyl-7-(3-methyl-2-buten-1-yl)-8-chloro-xanthine and 1.38 mg of potassium carbonate in 15 ml of N,N-dimethylformamide. The reaction mixture is stirred for eight hours at ambient temperature. After aqueous working up the crude product is purified by chromatography through a silica gel column with cyclohexane/ethyl acetate (8:1 to 8:1) as eluant.

Yield: 2.61 g (84% of theory)

Mass spectrum (ESI+): m/z=417, 419 [M+H]+

The following compounds are obtained analogously to Example V:

(1) 1-[2-(3-hydroxy-phenyl)-2-oxo-ethyl]-3-methyl-7-(3-methyl-2-buten-1-yl)-8-[3-(tert.-butyloxycarbonylamino)-piperidin-1-yl]-xanthine (The reaction is carried out with 2-bromo-1-[3-(tert.-butyldimethylsilanyloxy)-phenyl]-ethanone)

$R_f$ value: 0.40 (silica gel, cyclohexane/ethyl acetate=3:7)

Mass spectrum (ESI+): m/z=567 [M+H]+

(2) 1-(1-methyl-2-oxo-2-phenyl-ethyl)-3-methyl-7-(3-methyl-2-buten-1-yl)-8-chloro-xanthine Mass spectrum (ESI+): m/z=401, 403 [M+H]+

(3) 1-(2-cyano-ethyl)-3-methyl-7-(2-cyano-benzyl)-8-chloro-xanthine

Mass spectrum (ESI+): m/z=391, 393 [M+Na]+

(4) 1-(2-phenoxy-ethyl)-3-methyl-7-(2-cyano-benzyl)-8-[3-(tert.-butyloxycarbonylamino)-piperidin-1-yl]-xanthine $R_f$ value: 0.90 (silica gel, methylene chloride/methanol=9:1)

Mass spectrum (ESI+): m/z=600 [M+H]+

(5) 1-(2-phenyl-2-oxo-ethyl)-3-[(2-tri methylsilanyl-ethoxy)methyl]-7-(3-methyl-2-buten-1-yl)-8-[3-(tert.-butyloxycarbonylamino)-piperidin-1-yl]-xanthine Mass spectrum (ESI+): m/z=667 [M+H]+

(6) 1-(2-methoxy-ethyl)-3-methyl-7-(2-cyano-benzyl)-8-[3-(tert.-butyloxycarbonylamino)-piperidin-1-yl]-xanthine $R_f$ value: 0.90 (silica gel, methylene chloride/methanol=9:1)

Mass spectrum (ESI+): m/z=538 [M+H]+

(7) 1-methyl-3-[(2-trimethylsilanyl-ethoxy)methyl]-7-(2-cyano-benzyl)-xanthine $R_f$ value: 0.60 (silica gel, cyclohexane/ethyl acetate=1:1)

Mass spectrum (ESI+): m/z=412 [M+H]+

(8) 1-[2-(3-nitro-phenyl)-2-oxo-ethyl]-3-methyl-7-(3-methyl-2-buten-1-yl)-8-chloro-xanthine $R_f$ value: 0.40 (silica gel, cyclohexane/ethyl acetate/methanol=7:2:1)

Mass spectrum (ESI+): m/z=432, 434 [M+H]+

(9) 1-(2-phenyl-2-oxo-ethyl)-3-methyl-7-[(2-trimethylsilanyl-ethoxy)methyl]-8-bromo-xanthine Mass spectrum (ESI+): m/z=493, 495 [M+H]+

(10) 1-[2-(2-nitro-phenyl)-2-oxo-ethyl]-3-methyl-7-(3-methyl-2-buten-1-yl)-8-chloro-xanthine $R_f$ value: 0.64 (silica gel, cyclohexane/ethyl acetate=3:7)

Mass spectrum (ESI+): m/z=432, 434 [M+H]+

(11) 1-[2-(2-nitro-phenyl)-2-oxo-ethyl]-3-methyl-7-(3-methyl-2-buten-1-yl)-8-bromo-xanthine Mass spectrum (ESI+): m/z=476, 478 [M+H]+

(12) 1-[(quinolin-2-yl)methyl]-3-methyl-7-(3-methyl-2-buten-1-yl)-8-[3-(tert.-butyloxycarbonylamino)-piperidin-1-yl]-xanthine $R_f$ value: 0.45 (silica gel, ethyl acetate/petroleum ether=7:3)

Mass spectrum (ESI+): m/z=574 [M+H]+

(13) 1-[(2-oxo-2H-chromen-4-yl)methyl]-3-methyl-7-(3-methyl-2-buten-1-yl)-8-[3-(tert.-butyloxycarbonylamino)-piperidin-1-yl]-xanthine (The starting material 4-bromomethyl-chromen-2-one is prepared analogously to Kimura et al., Chem. Pharm. Bull. 1982, 30, 552-558.)

$R_f$ value: 0.52 (silica gel, methylene chloride/methanol=95:5)

Mass spectrum (ESI+): m/z=591 [M+H]+

(14) 1-[(1-methyl-2-oxo-1,2-dihydro-quinolin-4-yl)methyl]-3-methyl-7-(3-methyl-2-buten-1-yl)-8-[3-(tert.-butyloxycarbonylamino)-piperidin-1-yl]-xanthine $R_f$ value: 0.54 (silica gel, methylene chloride/methanol=95:5)

Mass spectrum (ESI+): m/z=604 [M+H]+

(15) 1-[(quinazolin-4-yl)methyl]-3-methyl-7-(3-methyl-2-buten-1-yl)-8-[3-(tert.-butyloxycarbonylamino)-piperidin-1-yl]-xanthine Melting point: 195-197° C.

Mass spectrum (ESI+): m/z=575 [M+H]+

(16) 1-[(5-methyl-3-phenyl-isoxazol-4-yl)methyl]-3-methyl-7-(3-methyl-2-buten-1-yl)-8-[3-(tert.-butyloxycarbonylamino)-piperidin-1-yl]-xanthine
$R_f$ value: 0.40 (silica gel, cyclohexane/ethyl acetate=1:1)
Mass spectrum (ESI$^+$): m/z=604 [M+H]$^+$

(17) 1-[(3-phenyl-[1,2,4]oxadiazol-5-yl)methyl]-3-methyl-7-(3-methyl-2-buten-1-yl)-8-[3-(tert.-butyloxycarbonylamino)-piperidin-1-yl]-xanthine
$R_f$ value: 0.18 (silica gel, petroleum ether/ethyl acetate=2:1)
Mass spectrum (ESI$^+$): m/z=591 [M+H]$^+$

(18) 1-[(4-phenyl-pyridin-2-yl)methyl]-3-methyl-7-(3-methyl-2-buten-1-yl)-8-[3-(tert.-butyloxycarbonylamino)-piperidin-1-yl]-xanthine
$R_f$ value: 0.53 (silica gel, methylene chloride/methanol=95:5)
Mass spectrum (ESI$^+$): m/z=600 [M+H]$^+$

(19) 1-[(5-phenyl-pyridin-2-yl)methyl]-3-methyl-7-(3-methyl-2-buten-1-yl)-8-[3-(tert.-butyloxycarbonylamino)-piperidin-1-yl]-xanthine
$R_f$ value: 0.73 (silica gel, ethyl acetate)
Mass spectrum (ESI$^+$): m/z=600 [M+H]$^+$

(20) 1-[2-(3-methylsulphanyl-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.43 (silica gel, cyclohexane/ethyl acetate=1:1)
Mass spectrum (ESI$^+$): m/z=597 [M+H]$^+$

(21) 1-[2-(3-methoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.27 (silica gel, methylene chloride/methanol=20:1)
Mass spectrum (ESI$^+$): m/z=609 [M+H]$^+$

(22) 1-[2-(2-ethoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.35 (silica gel, methylene chloride/methanol=20:1)
Mass spectrum (ESI$^+$): m/z=623 [M+H]$^+$

(23) 1-[2-(2,6-di methoxy-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.53 (silica gel, methylene chloride/methanol=20:1)
Mass spectrum (ESI$^+$): m/z=611 [M+H]$^+$

(24) 1-(2-phenyl-2-oxo-ethyl)-3-methyl-7-(2,3-dimethyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.38 (silica gel, methylene chloride/methanol=20:1)
Mass spectrum (ESI$^+$): m/z=565 [M+H]$^+$

(25) 1-((E)-3-phenyl-allyl)-3-methyl-7-(3-methyl-2-buten-1-yl)-8-[3-(tert.-butyloxycarbonylamino)-piperidin-1-yl]-xanthine
$R_f$ value: 0.54 (silica gel, methylene chloride/methanol/conc. aqueous ammonia=95:5:0.1)
Mass spectrum (ESI$^+$): m/z=549 [M+H]$^+$

(26) 1-[(1-benzo[b]thiophen-3-yl)methyl]-3-methyl-7-(3-methyl-2-buten-1-yl)-8-[3-(tert.-butyloxycarbonylamino)-piperidin-1-yl]-xanthine
$R_f$ value: 0.75 (silica gel, methylene chloride/methanol=95:5)
Mass spectrum (ESI$^+$): m/z=579 [M+H]$^+$

(27) 1-{[1-(tert.-butyloxycarbonyl)-indol-3-yl]methyl}-3-methyl-7-(3-methyl-2-buten-1-yl)-8-[3-(tert.-butyloxycarbonylamino)-piperidin-1-yl]-xanthine
$R_f$ value: 0.61 (silica gel, methylene chloride/methanol=9:1)
Mass spectrum (ESI$^+$): m/z=662 [M+H]$^+$

(28) 1-[(biphenyl-4-yl)methyl]-3-methyl-7-(3-methyl-2-buten-1-yl)-8-[3-(tert.-butyloxycarbonylamino)-piperidin-1-yl]-xanthine
$R_f$ value: 0.68 (silica gel, cyclohexane/ethyl acetate=1:1)
Mass spectrum (ESI$^+$): m/z=599 [M+H]$^+$

(29) 1-[(1-naphthyl)methyl]-3-methyl-7-(2-butyn-1-yl)-8-[3-(tert.-butyloxycarbonylamino)-piperidin-1-yl]-xanthine
$R_f$ value: 0.83 (silica gel, ethyl acetate/petroleum ether=4:1)
Mass spectrum (ESI$^+$): m/z=557 [M+H]$^+$

(30) 1-[(1-methyl-2-oxo-1,2-di hydro-quinolin-4-yl)methyl]-3-methyl-7-(2-butyn-1-yl)-8-[3-(tert.-butyloxycarbonylamino)-piperidin-1-yl]-xanthine
$R_f$ value: 0.25 (silica gel, ethyl acetate/petroleum ether=4:1)
Mass spectrum (ESI$^+$): m/z=588 [M+H]$^+$

(31) 1-(2-cyclohexyl-2-oxo-ethyl)-3-methyl-7-(3-methyl-2-buten-1-yl)-8-[3-(tert.-butyloxycarbonylamino)-piperidin-1-yl]-xanthine Melting point: 163-165° C.
Mass spectrum (ESI$^+$): m/z=557 [M+H]$^+$

(32) 1-(3,3-dimethyl-2-oxo-butyl)-3-methyl-7-(3-methyl-2-buten-1-yl)-8-[3-(tert.-butyloxycarbonylamino)-piperidin-1-yl]-xanthine
$R_f$ value: 0.95 (silica gel, ethyl acetate/petroleum ether=4:1)
Mass spectrum (ESI$^+$): m/z=531 [M+H]$^+$

(33) 1-[(quinazolin-2-yl)methyl]-3-methyl-7-(2-butyn-1-yl)-8-[3-(tert.-butyloxycarbonylamino)-piperidin-1-yl]-xanthine
$R_f$ value: 0.40 (silica gel, ethyl acetate)
Mass spectrum (ESI$^+$): m/z=559 [M+H]$^+$

(34) 1-[(2-methyl-naphthalen-1-yl)methyl]-3-methyl-7-(2-butyn-1-yl)-8-[3-(tert.-butyloxycarbonylamino)-piperidin-1-yl]-xanthine
$R_f$ value: 0.80 (silica gel, ethyl acetate)
Mass spectrum (ESI$^+$): m/z=571 [M+H]$^+$

(35) 1-[(5-nitro-isoquinolin-1-yl)methyl]-3-methyl-7-(3-methyl-2-buten-1-yl)-8-[3-(tert.-butyloxycarbonylamino)-piperidin-1-yl]-xanthine
$R_f$ value: 0.54 (silica gel, methylene chloride/methanol=95:5)

(36) 1-(2-di methylamino-2-oxo-ethyl)-3-methyl-7-(3-methyl-2-buten-1-yl)-8-[3-(tert.-butyloxycarbonylamino)-piperidin-1-yl]-xanthine
$R_f$ value: 0.23 (silica gel, ethyl acetate)
Mass spectrum (ESI$^+$): m/z=518 [M+H]$^+$

(37) 1-[2-(piperidin-1-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.44 (silica gel, ethyl acetate)
Mass spectrum (ESI$^+$): m/z=558 [M+H]$^+$

(38) 1-[(2-methyl-1-oxo-1,2-dihydro-isoquinolin-4-yl)methyl]-7-(2-butyn-1-yl)-8-[3-(tert.-butyloxycarbonylamino)-piperidin-1-yl]-xanthine
$R_f$ value: 0.25 (silica gel, ethyl acetate)
Mass spectrum (ESI$^+$): m/z=588 [M+H]$^+$

(39) 1-[(2-methyl-1-oxo-1,2-dihydro-isoquinolin-4-yl)methyl]-7-(3-methyl-2-buten-1-yl)-8-[3-(tert.-butyloxycarbonylamino)-piperidin-1-yl]-xanthine R$_f$ value: 0.30 (silica gel, ethyl acetate)
Mass spectrum (ESI$^+$): m/z=604 [M+H]$^+$

(40) 1-[(2-methoxy-naphthalen-1-yl)methyl]-3-methyl-7-(2-butyn-1-yl)-8-[3-(tert.-butyloxycarbonylamino)-piperidin-1-yl]-xanthine
R$_f$ value: 0.75 (silica gel, ethyl acetate)
Mass spectrum (ESI$^+$): m/z=587 [M+H]$^+$

(41) 1-[(4-methoxy-naphthalen-1-yl)methyl]-3-methyl-7-(2-butyn-1-yl)-8-[3-(tert.-butyloxycarbonylamino)-piperidin-1-yl]-xanthine
R$_f$ value: 0.80 (silica gel, ethyl acetate)
Mass spectrum (ESI$^+$): m/z=587 [M+H]$^+$

(42) 1-[(3-methyl-isoquinolin-1-yl)methyl]-3-methyl-7-(2-butyn-1-yl)-8-[3-(tert.-butyloxycarbonylamino)-piperidin-1-yl]-xanthine
R$_f$ value: 0.56 (silica gel, methylene chloride/methanol=95:5)
Mass spectrum (ESI$^+$): m/z=572 [M+H]$^+$

(43) 1-[2-(2,3-di methoxy-phenyl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.83 (silica gel, ethyl acetate)
Mass spectrum (ESI$^+$): m/z=611 [M+H]$^+$

(44) 1-[(5-nitro-naphthalen-1-yl)methyl]-3-methyl-7-(2-butyn-1-yl)-8-[3-(tert.-butyloxycarbonylamino)-piperidin-1-yl]-xanthine
R$_f$ value: 0.78 (silica gel, ethyl acetate)
Mass spectrum (ESI$^+$): m/z=602 [M+H]$^+$

(45) 1-[2-(pyrrolidin-1-yl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.39 (silica gel, ethyl acetate)
Mass spectrum (ESI$^+$): m/z=544 [M+H]$^+$

(46) 1-[(4-methyl-isoquinolin-1-yl)methyl]-3-methyl-7-(2-butyn-1-yl)-8-[3-(tert.-butyloxycarbonylamino)-piperidin-1-yl]-xanthine
R$_f$ value: 0.56 (silica gel, methylene chloride/methanol=95:5)
Mass spectrum (ESI$^+$): m/z=572 [M+H]$^+$

(47) 1-[(2-naphthyl)methyl]-3-methyl-7-(2-butyn-1-yl)-8-[3-(tert.-butyloxycarbonylamino)-piperidin-1-yl]-xanthine
R$_f$ value: 0.78 (silica gel, ethyl acetate)
Mass spectrum (ESI$^+$): m/z=557 [M+H]$^+$

(48) 1-cyanomethyl-3-methyl-7-(2-butyn-1-yl)-8-[3-(tert.-butyloxycarbonyl-amino)-piperidin-1-yl]-xanthine
R$_f$ value: 0.80 (silica gel, ethyl acetate)
Mass spectrum (ESI$^+$): m/z=456 [M+H]$^+$

(49) 1-[(quinolin-6-yl)methyl]-3-methyl-7-(2-butyn-1-yl)-8-[3-(tert.-butyloxycarbonylamino)-piperidin-1-yl]-xanthine
R$_f$ value: 0.40 (silica gel, ethyl acetate)
Mass spectrum (ESI$^+$): m/z=558 [M+H]$^+$

(50) 1-[(3-methoxy-naphthalen-2-yl)methyl]-3-methyl-7-(2-butyn-1-yl)-8-[3-(tert.-butyloxycarbonylamino)-piperidin-1-yl]-xanthine
R$_f$ value: 0.83 (silica gel, ethyl acetate)
Mass spectrum (ESI$^+$): m/z=587 [M+H]$^+$

(51) 1-[2-(2,3-dihydro-benzo[1,4]dioxin-5-yl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.38 (silica gel, ethyl acetate/petroleum ether=1:1)
Mass spectrum (ESI$^+$): m/z=609 [M+H]$^+$

(52) 1-[2-(3-methyl-2-oxo-2,3-dihydro-benzooxazol-7-yl)-2-oxo-ethyl]-3-methyl-7-(3-methyl-2-buten-1-yl)-8-[3-(tert.-butyloxycarbonylamino)-piperidin-1-yl]-xanthine
(Carried out with potassium-tert. butoxide in dimethylsulphoxide)
R$_f$ value: 0.48 (silica gel, ethyl acetate/petroleum ether=2:1)
Mass spectrum (ESI$^+$): m/z=622 [M+H]$^+$

(53) 1-[2-(benzo[1,3]dioxol-4-yl)-2-oxo-ethyl]-3-methyl-7-(3-methyl-2-buten-1-yl)-8-[3-(tert.-butyloxycarbonylamino)-piperidin-1-yl]-xanthine
Mass spectrum (ESI$^+$): m/z=595 [M+H]$^+$

(54) 1-[(quinazolin-2-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=559 [M+H]$^+$

(55) 1-[(quinazolin-2-yl)methyl]-3-methyl-7-(2-butyn-1-yl)-8-[(S)-3-(tert.-butyloxycarbonylamino)-piperidin-1-yl]-xanthine
Mass spectrum (ESI$^+$): m/z=559 [M+H]$^+$

(56) 1-[(quinazolin-2-yl)methyl]-3-methyl-7-((E)-2-buten-1-yl)-8-[(S)-3-(tert.-butyloxycarbonylamino)-piperidin-1-yl]-xanthine (product contains approx. 15% of Z isomer)
R$_f$ value: 0.30 (silica gel, ethyl acetate/cyclohexane=8:2)
Mass spectrum (ESI$^+$): m/z=561 [M+H]$^+$

(57) 1-[(quinazolin-2-yl)methyl]-3-methyl-7-((E)-2-buten-1-yl)-8-[(R)-3-(tert.-butyloxycarbonylamino)-piperidin-1-yl]-xanthine (product contains approx. 15% of Z isomer)
R$_f$ value: 0.30 (silica gel, ethyl acetate/cyclohexane=8:2)
Mass spectrum (ESI$^+$): m/z=561 [M+H]$^+$

(58) 1-[(3-methyl-isoquinolin-1-yl)methyl]-3-methyl-7-((E)-2-buten-1-yl)-8-[(R)-3-(tert.-butyloxycarbonylamino)-piperidin-1-yl]-xanthine (product contains approx. 17% of Z isomer)
R$_f$ value: 0.58 (silica gel, methylene chloride/methanol=95:5)
Mass spectrum (ESI$^+$): m/z=574 [M+H]$^+$

(59) 1-[(3-methyl-isoquinolin-1-yl)methyl]-3-methyl-7-((E)-2-buten-1-yl)-8-[(S)-3-(tert.-butyloxycarbonylamino)-piperidin-1-yl]-xanthine (product contains approx. 17% of Z isomer)
R$_f$ value: 0.58 (silica gel, methylene chloride/methanol=95:5)
Mass spectrum (ESI$^+$): m/z=574 [M+H]$^+$

(60) 1-[2-(2-methoxy-phenyl)-2-oxo-ethyl]-3-methyl-7-(2-butyn-1-yl)-8-bromo-xanthine
Mass spectrum (ESI$^+$): m/z=445, 447 [M+H]$^+$

(61) 1-[2-(2-nitro-phenyl)-2-oxo-ethyl]-3-methyl-7-[(1-cyclopenten-1-yl)methyl]-8-bromo-xanthine
Mass spectrum (ESI$^+$): m/z=488, 490 [M+H]$^+$

(62) 1-[2-(2-methoxy-phenyl)-2-oxo-ethyl]-3-methyl-7-[(1-cyclopenten-1-yl)methyl]-8-bromo-xanthine
Mass spectrum (ESI$^+$): m/z=473, 475 [M+H]$^+$

(63) 1-[(isoquinolin-1-yl)methyl]-3-[(methoxycarbonyl)methyl]-7-(3-methyl-2-buten-1-yl)-8-[3-(tert.-butyloxycarbonylamino)-piperidin-1-yl]-xanthine
R$_f$ value: 0.35 (silica gel, methylene chloride/methanol=95:5)

(64) 1-[2-(2-nitro-phenyl)-2-oxo-ethyl]-3-methyl-7-((E)-2-buten-1-yl)-8-bromo-xanthine (product contains approx. 10% of Z isomer)
R$_f$ value: 0.60 (silica gel, cyclohexane/ethyl acetate=4:6)
Mass spectrum (ESI$^+$): m/z=462, 464 [M+H]$^+$

(65) 1-[2-(2-methoxy-phenyl)-2-oxo-ethyl]-3-methyl-7-((E)-2-buten-1-yl)-8-bromo-xanthine
(product contains some Z isomer)
R$_f$ value: 0.30 (silica gel, cyclohexane/ethyl acetate=1:1)
Mass spectrum (ESI$^+$): m/z=447, 449 [M+H]$^+$

(66) 1-[2-(2-nitro-phenyl)-2-oxo-ethyl]-3-methyl-7-(2-butyn-1-yl)-8-bromo-xanthine $R_f$ value: 0.77 (silica gel, methylene chloride/methanol=95:5)
Mass spectrum (ESI$^+$): m/z=460, 462 [M+H]$^+$

(67) 1-(2-phenyl-2-oxo-ethyl)-3-methyl-7-((E)-2-buten-1-yl)-8-[(R)-3-(tert.-butyloxycarbonylamino)-piperidin-1-yl]-xanthine
(product contains approx. 20% of Z isomer)
Mass spectrum (ESI$^+$): m/z=537 [M+H]$^+$

(68) 1-[2-(2-methoxy-phenyl)-2-oxo-ethyl]-3-methyl-7-(3-methyl-2-buten-1-yl)-8-bromo-xanthine
Mass spectrum (ESI$^+$): m/z=461, 463 [M+H]$^+$

(69) 1-(2-phenyl-2-oxo-ethyl)-3-methyl-7-(2-butyn-1-yl)-8-bromo-xanthine
$R_f$ value: 0.61 (silica gel, cyclohexane/ethyl acetate=4:6)

(70) 1-(2-{2-[(ethylaminocarbonyl)methoxy]-phenyl}-2-oxo-ethyl)-3-methyl-7-((E)-2-buten-1-yl)-8-[(R)-3-(tert.-butyloxycarbonylamino)-piperidin-1-yl]-xanthine
(product contains approx. 17% of Z isomer)
Mass spectrum (ESI$^+$): m/z=638 [M+H]$^+$

(71) 1-(2-phenyl-2-oxo-ethyl)-3-methyl-7-((E)-2-buten-1-yl)-8-[(S)-3-(tert.-butyloxycarbonylamino)-piperidin-1-yl]-xanthine
(product contains approx. 18% of Z isomer)
$R_f$ value: 0.35 (silica gel, cyclohexane/ethyl acetate=6:4)
Mass spectrum (ESI$^+$): m/z=537 [M+H]$^+$

(72) 1-[2-(2-nitro-phenyl)-2-oxo-ethyl]-3-methyl-7-(2-butyn-1-yl)-8-[(S)-3-(tert.-butyloxycarbonylamino)-piperidin-1-yl]-xanthine
$R_f$ value: 0.60 (silica gel, methylene chloride/methanol=95:5)
Mass spectrum (ESI$^+$): m/z=580 [M+H]$^+$

(73) 1-[(3-methyl-isoquinolin-1-yl)methyl]-3-methyl-7-(2-butyn-1-yl)-8-[(S)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=572 [M+H]$^+$

(74) 1-[(3-methyl-isoquinolin-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=572 [M+H]$^+$

(75) 1-[(4-methyl-isoquinolin-1-yl)methyl]-3-methyl-7-(2-butyn-1-yl)-8-[(S)-3-(tert.-butyloxycarbonylamino)-piperidin-1-yl]-xanthine
Mass spectrum (ESI$^+$): m/z=572 [M+H]$^+$

(76) 1-[(4-methyl-isoquinolin-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=572 [M+H]$^+$

(77) 1-[(4-methyl-isoquinolin-1-yl)methyl]-3-methyl-7-((E)-2-buten-1-yl)-8-[(S)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=574 [M+H]$^+$

(78) 1-[(4-methyl-isoquinolin-1-yl)methyl]-3-methyl-7-((E)-2-buten-1-yl)-8-[(R)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=574 [M+H]$^+$

(79) 1-[2-(2,3-dihydro-benzo[1,4]dioxin-5-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.18 (silica gel, ethyl acetate/petroleum ether=1:1)
Mass spectrum (ESI$^+$): m/z=593 [M+H]$^+$

(80) 1-[2-(2,3-dihydro-benzo[1,4]dioxin-5-yl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI$^+$): m/z=593 [M+H]$^+$

(81) 1-[(4-methoxy-naphthalen-1-yl)methyl]-3-methyl-7-(2-butyn-1-yl)-8-[(S)-3-(tert.-butyloxycarbonylamino)-piperidin-1-yl]-xanthine
$R_f$ value: 0.56 (silica gel, petroleum ether/ethyl acetate=1:2)
Mass spectrum (ESI$^+$): m/z=587 [M+H]$^+$

(82) 1-[(4-methoxy-naphthalen-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=587 [M+H]$^+$

(83) 1-[2-(benzo[1,3]dioxol-4-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.86 (silica gel, ethyl acetate/petroleum ether=4:1)
Mass spectrum (ESI$^+$): m/z=579 [M+H]$^+$

(84) 1-[2-(benzo[1,3]dioxol-4-yl)-2-oxo-ethyl]-3-methyl-7-(2-butyn-1-yl)-8-[(S)-3-(tert.-butyloxycarbonylamino)-piperidin-1-yl]-xanthine
$R_f$ value: 0.86 (silica gel, ethyl acetate/petroleum ether=4:1)
Mass spectrum (ESI$^+$): m/z=579 [M+H]$^+$

(85) 1-[(4-methyl-quinazolin-2-yl)methyl]-3-methyl-7-(2-butyn-1-yl)-8-[(S)-3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=573 [M+H]$^+$

(86) 1-[(4-methyl-quinazolin-2-yl)methyl]-3-methyl-7-(2-butyn-1-yl)-8-[(R)-3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=573 [M+H]$^+$

(87) 1-[2-(3-methyl-2-oxo-2,3-dihydro-benzooxazol-4-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.50 (silica gel, petroleum ether/ethyl acetate=1:2)
Mass spectrum (ESI$^+$): m/z=622 [M+H]$^+$

(88) 1-(2-{2-[(ethylaminocarbonyl)methoxy]-phenyl}-2-oxo-ethyl)-3-methyl-7-((E)-2-buten-1-yl)-8-[(S)-3-(tert.-butyloxycarbonylamino)-piperidin-1-yl]-xanthine
Mass spectrum (ESI$^+$): m/z=638 [M+H]$^+$

(89) 1-(2-{2-[(methylaminocarbonyl)methoxy]-phenyl}-2-oxo-ethyl)-3-methyl-7-((E)-2-buten-1-yl)-8-[(R)-3-(tert.-butyloxycarbonylamino)-piperidin-1-yl]-xanthine
Mass spectrum (ESI$^+$): m/z=624 [M+H]$^+$

(90) 1-(2-{2-[(methylaminocarbonyl)methoxy]-phenyl}-2-oxo-ethyl)-3-methyl-7-((E)-2-buten-1-yl)-8-[(S)-3-(tert.-butyloxycarbonylamino)-piperidin-1-yl]-xanthine
Mass spectrum (ESI$^+$): m/z=624 [M+H]$^+$

(91) 1-[2-(2-nitro-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.60 (silica gel, methylene chloride/methanol=95:5)

(92) 1-[2-(2-nitro-3-methoxy-phenyl)-2-oxo-ethyl]-3-methyl-7-(3-methyl-2-buten-1-yl)-8-bromo-xanthine
Mass spectrum (ESI$^+$): m/z=506, 508 [M+H]$^+$

(93) 1-[(4-dimethylamino-quinazolin-2-yl)methyl]-3-methyl-7-(2-butyn-1-yl)-8-[3-(tert.-butyloxycarbonylamino)-piperidin-1-yl]-xanthine (Carried out in the presence of caesium carbonate)

R$_f$ value: 0.40 (silica gel, methylene chloride/methanol=95:5)

Mass spectrum (ESI$^+$): m/z=602 [M+H]$^+$

(94) 1-(2-{2-oxo-3-[(2-trimethylsilanyl-ethoxy)methyl]-2,3-dihydro-benzooxazol-7-yl}-2-oxo-ethyl)-3-methyl-7-(3-methyl-2-buten-1-yl)-8-bromo-xanthine R$_f$ value: 0.75 (silica gel, ethyl acetate/petroleum ether=1:1)

Mass spectrum (ESI$^+$): m/z=618, 620 [M+H]$^+$

(95) 1-[(imidazo[1,2-a]pyridin-2-yl)methyl]-3-methyl-7-(2-butyn-1-yl)-8-[3-(tert.-butyloxycarbonylamino)-piperidin-1-yl]-xanthine R$_f$ value: 0.44 (silica gel, methylene chloride/methanol=95:5)

Mass spectrum (ESI$^+$): m/z=547 [M+H]$^+$

(96) 1-[(quinoxalin-2-yl)methyl]-3-methyl-7-(2-butyn-1-yl)-8-[3-(tert.-butyloxycarbonyl-amino)-piperidin-1-yl]-xanthine R$_f$ value: 0.50 (silica gel, methylene chloride/methanol=95:5)

Mass spectrum (ESI$^+$): m/z=559 [M+H]$^+$

(97) 1-[2-(1,3-dimethyl-2-oxo-2,3-dihydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine R$_f$ value: 0.50 (silica gel, methylene chloride/methanol=95:5)

Mass spectrum (ESI$^+$): m/z=619 [M+H]$^+$

(98) 1-[(quinoxalin-6-yl)methyl]-3-methyl-7-(2-butyn-1-yl)-8-[3-(tert.-butyloxycarbonylamino)-piperidin-1-yl]-xanthine R$_f$ value: 0.35 (silica gel, ethyl acetate)

Mass spectrum (ESI$^+$): m/z=559 [M+H]$^+$

(99) 1-(2-{2-oxo-3-[(2-trimethylsilanyl-ethoxy)methyl]-2,3-dihydro-benzooxazol-4-yl}-2-oxo-ethyl)-3-methyl-7-(2-butyn-1-yl)-8-bromo-xanthine R$_f$ value: 0.30 (silica gel, petroleum ether/ethyl acetate=2:1)

Mass spectrum (ESI$^-$): m/z=600, 602 [M-H]

(100) 1-[(3-methyl-quinoxalin-2-yl)methyl]-3-methyl-7-(2-butyn-1-yl)-8-[3-(tert.-butyloxycarbonylamino)-piperidin-1-yl]-xanthine R$_f$ value: 0.44 (silica gel, petroleum ether/ethyl acetate=1:2)

Mass spectrum (ESI$^+$): m/z=573 [M+H]$^+$ (101) 1-[(3-phenyl-isoquinolin-1-yl)methyl]-3-methyl-7-(2-butyn-1-yl)-8-[3-(tert.-butyloxycarbonylamino)-piperidin-1-yl]-xanthine R$_f$ value: 0.85 (silica gel, ethyl acetate)

Mass spectrum (ESI$^+$): m/z=634 [M+H]$^+$ (102) 1-[(3,4-dimethyl-isoquinolin-1-yl)methyl]-3-methyl-7-(2-butyn-1-yl)-8-[3-(tert.-butyloxycarbonylamino)-piperidin-1-yl]-xanthine R$_f$ value: 0.60 (silica gel, ethyl acetate/methanol=3:1)

Mass spectrum (ESI$^+$): m/z=586 [M+H]$^+$ (103) 1-[(benzofuran-2-yl)methyl]-3-methyl-7-(2-butyn-1-yl)-[(R)-3-(tert.-butyl-oxycarbonylamino)-piperidin-1-yl]-xanthine Mass spectrum (ESI$^+$): m/z=547 [M+H]$^+$ (104) 1-{[4-(morpholin-4-yl)-quinazolin-2-yl]methyl}-3-methyl-7-(2-butyn-1-yl)-8-[3-(tert.-butyloxycarbonylamino)-piperidin-1-yl]-xanthine (Carried out in the presence of caesium carbonate)

R$_f$ value: 0.28 (silica gel, ethyl acetate)

Mass spectrum (ESI$^+$): m/z=644 [M+H]$^+$ (105) 1-{[4-(piperidin-1-yl)-quinazolin-2-yl]methyl}-3-methyl-7-(2-butyn-1-yl)-8-[3-(tert.-butyloxycarbonylamino)-piperidin-1-yl]-xanthine (Carried out in the presence of caesium carbonate)

R$_f$ value: 0.35 (silica gel, ethyl acetate)

Mass spectrum (ESI$^+$): m/z=642 [M+H]$^+$ (106) 1-({4-[4-(tert.-butyloxycarbonyl)-piperazin-1-yl]-quinazolin-2-yl}methyl)-3-methyl-7-(2-butyn-1-yl)-8-[3-(tert.-butyloxycarbonylamino)-piperidin-1-yl]-xanthine (Carried out in the presence of caesium carbonate)

R$_f$ value: 0.50 (silica gel, ethyl acetate)

Mass spectrum (ESI$^+$): m/z=743 [M+H]$^+$ (107) 1-{[4-(pyrrolidin-1-yl)-quinazolin-2-yl]methyl}-3-methyl-7-(2-butyn-1-yl)-8-[3-(tert.-butyloxycarbonylamino)-piperidin-1-yl]-xanthine (Carried out in the presence of caesium carbonate)

R$_f$ value: 0.59 (silica gel, ethyl acetate/methanol/conc. aqueous ammonia=95:5:0.1)

Mass spectrum (ESI$^+$): m/z=628 [M+H]$^+$ (108) 1-[2-(1-ethoxycarbonyl-3-methyl-2-oxo-2,3-di hydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine R$_f$ value: 0.25 (silica gel, petroleum ether/ethyl acetate=1:2)

Mass spectrum (ESI$^+$): m/z=677 [M+H]$^+$ (109) 1-[(4-cyano-naphthalen-1-yl)methyl]-3-methyl-7-(2-butyn-1-yl)-8-[(R)-3-(tert.-butyloxycarbonylamino)-piperidin-1-yl]-xanthine R$_f$ value: 0.77 (silica gel, methylene chloride/methanol/conc. aqueous ammonia=90:10:1)

Mass spectrum (ESI$^+$): m/z=582 [M+H]$^+$ (110) 1-[(imidazo[1,2-a]pyridine-3-yl)methyl]-3-methyl-7-(2-butyn-1-yl)-8-[3-(tert.-butyloxycarbonylamino)-piperidin-1-yl]-xanthine Mass spectrum (ESI$^+$): m/z=547 [M+H]$^+$ (111) 1-[(8-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine R$_f$ value: 0.25 (silica gel, ethyl acetate)

Mass spectrum (ESI$^+$): m/z=561 [M+H]$^+$ (112) 1-[(8-methoxy-quinolin-5-yl)methyl]-3-methyl-7-(2-butyn-1-yl)-8-[3-(tert.-butyloxycarbonylamino)-piperidin-1-yl]-xanthine R$_f$ value: 0.60 (silica gel, ethyl acetate/methanol=9:1)

Mass spectrum (ESI$^+$): m/z=588 [M+H]$^+$ (113) 1-[(5-methoxy-quinolin-8-yl)methyl]-3-methyl-7-(2-butyn-1-yl)-8-[3-(tert.-butyloxycarbonylamino)-piperidin-1-yl]-xanthine R$_f$ value: 0.40 (silica gel, methylene chloride/methanol=20:1)

Mass spectrum (ESI$^+$): m/z=588 [M+H]$^+$ (114) 1-[(4-phenyl-quinazolin-2-yl)methyl]-3-methyl-7-(2-butyn-1-yl)-8-[3-(tert.-butyloxycarbonylamino)-piperidin-1-yl]-xanthine Mass spectrum (ESI$^+$): m/z=635 [M+H]$^+$ (115) 1-[(7-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine R$_f$ value: 0.50 (silica gel, methylene chloride/methanol=95:5)

Mass spectrum (ESI$^+$): m/z=561 [M+H]$^+$ (116) 1-(2-oxo-4-phenyl-butyl)-3-methyl-7-(2-butyn-1-yl)-8-[(R)-3-(tert.-butyloxycarbonylamino)-piperidin-1-yl]-xanthine Mass spectrum (ESI$^+$): m/z=563 [M+H]$^+$ (117) 1-(2-{2-oxo-1,3-bis-[(2-trimethylsilanyl-ethoxy)methyl]-2,3-dihydro-1H-benzoimidazol-4-yl}-2-oxo-ethyl)-3-methyl-7-(2-butyn-1-yl)-8-[3-(tert.-butyloxy-carbonylamino)-piperidin-1-yl]-xanthine $R_f$ value: 0.50 (silica gel, ethyl acetate/petroleum ether=1:1)

Mass spectrum (ESI$^+$): m/z=851 [M+H]$^+$ (118) 1-[(3-difluoromethyl-isoquinolin-1-yl)methyl]-3-methyl-7-(2-butyn-1-yl)-8-[3-(tert.-butyloxycarbonylamino)-piperidin-1-yl]-xanthine (By-product of the reaction of 3-methyl-7-(2-butyn-1-yl)-8-[3-(tert.-butyloxycarbonylamino)-piperidin-1-yl]-xanthine with 1-chloromethyl-3-trifluoromethyl-3,4-dihydro-isoquinoline)

$R_f$ value: 0.75 (aluminium oxide, petroleum ether/ethyl acetate=1:2)

Mass spectrum (ESI$^+$): m/z=608 [M+H]$^+$ (119) 1-[2-(2,2-difluoro-benzo[1,3]dioxol-4-yl)-2-oxo-ethyl]-3-methyl-7-(2-butyn-1-yl)-8-bromo-xanthine Mass spectrum (ESI$^+$): m/z=495, 497 [M+H]$^+$ (120) 1-[(3-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol=95:5)

Mass spectrum (ESI$^+$): m/z=561 [M+H]$^+$ (121) 1-[(5-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol/conc. aqueous ammonia=90:10:1)

Mass spectrum (ESI$^+$): m/z=561 [M+H]$^+$ (122) 1-[(6-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.10 (silica gel, ethyl acetate/methanol=98:2)

Mass spectrum (ESI$^+$): m/z=561 [M+H]$^+$ (123) 1-[(3-benzyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.60 (silica gel, methylene chloride/methanol=95:5)

Mass spectrum (ESI$^+$): m/z=637 [M+H]$^+$ (124) 1-[(4-isopropyl-quinazolin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, ethyl acetate/petroleum ether=8:2)

Mass spectrum (ESI$^+$): m/z=601 [M+H]$^+$ (125) 1-[(2,3-dihydro-benzo[1,4]dioxin-6-yl)methyl]-3-methyl-7-(2-butyn-1-yl)-8-[3-(tert.-butyloxycarbonylamino)-piperidin-1-yl]-xanthine $R_f$ value: 0.53 (silica gel, ethyl acetate/petroleum ether=3:2)

(126) 1-[(3-phenyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol=95:5)

Mass spectrum (ESI$^+$): m/z=623 [M+H]$^+$ (127) 1-[2-(naphthalen-1-yl)-2-oxo-ethyl]-3-methyl-7-(2-butyn-1-yl)-8-[3-(tert.-butyloxycarbonylamino)-piperidin-1-yl]-xanthine $R_f$ value: 0.54 (silica gel, methylene chloride/methanol=95:5)

Mass spectrum (ESI$^+$): m/z=585 [M+H]$^+$ (128) 1-[(5-methoxy-isoquinolin-8-yl)methyl]-3-methyl-7-(2-butyn-1-yl)-8-[3-(tert.-butyloxycarbonylamino)-piperidin-1-yl]-xanthine $R_f$ value: 0.50 (silica gel, ethyl acetate/methanol=24:1)

Mass spectrum (ESI$^+$): m/z=588 [M+H]$^+$ (129) 1-[(3-difluoromethyl-isoquinolin-1-yl)methyl]-3-methyl-7-(2-butyn-1-yl)-8-[3-(tert.-butyloxycarbonylamino)-piperidin-1-yl]-xanthine (By-product of the reaction of 3-methyl-7-(2-butyn-1-yl)-8-[3-(tert.-butyloxycarbonylamino)-piperidin-1-yl]-xanthine with 1-chloromethyl-3-trifluoromethyl-3,4-dihydro-isoquinoline)

$R_f$ value: 0.75 (aluminium oxide, petroleum ether/ethyl acetate=1:2)

Mass spectrum (ESI$^+$): m/z=608 [M+H]$^+$ (130) 1-{[1-(1-cyano-1-methyl-ethyl)-isoquinolin-3-yl]methyl}-3-methyl-7-(2-butyn-1-yl)-8-[3-(tert.-butyloxycarbonylamino)-piperidin-1-yl]-xanthine $R_f$ value: 0.75 (silica gel, ethyl acetate)

Mass spectrum (ESI$^+$): m/z=625 [M+H]$^+$ (132) 1-methoxycarbonylmethyl-3-methyl-7-(2-butyn-1-yl)-8-[3-(tert.-butyloxycarbonyl-amino)-piperidin-1-yl]-xanthine Mass spectrum (ESI$^+$): m/z=489 [M+H]$^+$ (133) 1-[(4-phenyl-quinazolin-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=635 [M+H]$^+$ (134) 1-[(2,3-dimethyl-quinoxalin-6-yl)methyl]-3-methyl-7-(2-butyn-1-yl)-8-[3-(tert.-butyloxycarbonylamino)-piperidin-1-yl]-xanthine (Carried out in the presence of caesium carbonate)

$R_f$ value: 0.40 (silica gel, ethyl acetate)

Mass spectrum (ESI$^+$): m/z=587 [M+H]$^+$ (135) 1-[(4-phenyl-quinazolin-2-yl)methyl]-3-methyl-7-(2-butyn-1-yl)-8-[(S)-3-(tert.-butyloxycarbonylamino)-piperidin-1-yl]-xanthine $R_f$ value: 0.55 (silica gel, ethyl acetate/petroleum ether=8:2)

Mass spectrum (ESI$^+$): m/z=635 [M+H]$^+$ (136) 1-[2-(quinolin-8-yl-)-2-oxo-ethyl]-3-methyl-7-(2-butyn-1-yl)-8-bromo-xanthine $R_f$ value: 0.55 (silica gel, methylene chloride/methanol=95:5)

Mass spectrum (ESI$^+$): m/z=466, 468 [M+H]$^+$ (137) 1-[(3,4-dimethyl-6,7-dihydro-5H-[2]pyrindin-1-yl)methyl]-3-methyl-7-(2-butyn-1-yl)-8-[3-(tert.-butyloxycarbonylamino)-piperidin-1-yl]-xanthine $R_f$ value: 0.65 (aluminium oxide, ethyl acetate/petroleum ether=3:1)

Mass spectrum (ESI$^+$): m/z=576 [M+H]$^+$ (138) 1-[(3,4-dimethyl-5,6,7,8-tetrahydro-isoquinolin-1-yl)methyl]-3-methyl-7-(2-butyn-1-yl)-8-[3-(tert.-butyloxycarbonylamino)-piperidin-1-yl]-xanthine $R_f$ value: 0.40 (aluminium oxide, methylene chloride/methanol=20:1)

Mass spectrum (ESI$^+$): m/z=590 [M+H]$^+$ (139) 1-{2-[1-(tert.-butyloxycarbonyl)-1H-indol-4-yl]-2-oxo-ethyl}-3-methyl-7-(2-butyn-1-yl)-8-[3-(tert.-butyloxycarbonylamino)-piperidin-1-yl]-xanthine $R_f$ value: 0.55 (silica gel, petroleum ether/ethyl acetate=1:2)

Mass spectrum (ESI$^+$): m/z=674 [M+H]$^+$ (140) 1-[(1-methyl-2-oxo-1,2-dihydro-quinolin-6-yl)methyl]-3-methyl-7-(2-butyn-1-yl)-8-[3-(tert.-butyloxycarbonylamino)-piperidin-1-yl]-xanthine Mass spectrum (EI): m/z=587 [M]$^+$ (141) 1-({1-[(2-trimethylsilanyl-ethoxy)methyl]-2-oxo-1,2-dihydro-quinolin-6-yl}methyl)-3-methyl-7-(2-butyn-1-yl)-8-[3-(tert.-butyloxycarbonylamino)-piperidin-1-yl]-xanthine Mass spectrum (ESI$^+$): m/z=704 [M+H]$^+$ (142) 1-[(2,3,8-trimethyl-quinoxalin-6-yl)methyl]-3-methyl-7-(2-butyn-1-yl)-8-[3-(tert.-butyloxycarbonylamino)-piperidin-1-yl]-xanthine Mass spectrum (ESI$^+$): m/z=601 [M+H]$^+$ (143) 1-[(8-methyl-quinoxalin-6-yl)methyl]-3-methyl-7-(2-butyn-1-yl)-8-[3-(tert.-butyloxycarbonylamino)-piperidin-1-yl]-xanthine Mass spectrum (ESI$^+$): m/z=573 [M+H]$^+$ (144) 1-[(4-methyl-phthalazin-1-yl)methyl]-3-methyl-7-(2-butyn-1-yl)-8-[3-(tert.-butyloxycarbonylamino)-piperidin-1-yl]-xanthine $R_f$ value: 0.65 (silica gel, methylene chloride/methanol=9:1)

Mass spectrum (ESI$^+$): m/z=573 [M+H]$^+$ (145) 1-[(4-bromo-3-methoxy-isoquinolin-1-yl)methyl]-3-methyl-7-(2-butyn-1-yl)-8-[3-(tert.-butyloxycarbonylamino)-piperidin-1-yl]-xanthine $R_f$ value: 0.65 (silica gel, methylene chloride/ethyl acetate=1:1)

Mass spectrum (ESI$^+$): m/z=666, 668 [M+H]$^+$ (146) 1-[(4-difluoromethoxy-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, methylene chloride/methanol/conc. aqueous ammonia=90:10:1)

Mass spectrum (ESI$^+$): m/z=623 [M+H]$^+$ (147) 1-{2-[1-(tert.-butyloxycarbonyl)-1H-indol-7-yl]-2-oxo-ethyl}-3-methyl-7-(2-butyn-1-yl)-8-bromo-xanthine $R_f$ value: 0.83 (silica gel, methylene chloride/methanol=95:5)

(148) 1-[(E)-3-(2-nitro-phenyl)-2-propen-1-yl]-3-methyl-7-(2-butyn-1-yl)-8-[3-(tert.-butyloxycarbonylamino)-piperidin-1-yl]-xanthine Mass spectrum (ESI$^+$): m/z=578 [M+H]$^+$ (149) 1-((E)-3-pentafluorophenyl-2-propen-1-yl)-3-methyl-7-(2-butyn-1-yl)-8-[3-(tert.-butyloxycarbonylamino)-piperidin-1-yl]-xanthine Mass spectrum (ESI$^+$): m/z=623 [M+H]$^+$ (150) 1-[(4-nitro-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.41 (silica gel, methylene chloride/methanol=95:5)

Mass spectrum (ESI$^+$): m/z=602 [M+H]$^+$ (151) 1-[(benzooxazol-2-y)methyl]-3-methyl-7-(2-butyn-1-yl)-8-[3-(tert.-butyloxycarbo-nylamino)-piperidin-1-yl]-xanthine $R_f$ value: 0.40 (silica gel, cyclohexane/ethyl acetate=3:7)

Mass spectrum (ESI$^+$): m/z=548 [M+H]$^+$ (152) 1-[(5-nitro-benzooxazol-2-y)methyl]-3-methyl-7-(2-butyn-1-yl)-8-[3-(tert.-butyloxycarbonylamino)-piperidin-1-yl]-xanthine $R_f$ value: 0.50 (silica gel, cyclohexane/ethyl acetate/methanol=5:4:1)

Mass spectrum (ESI$^+$): m/z=593 [M+H]$^+$ (153) 1-[(3-methyl-isoquinolin-1-yl)methyl]-3-methyl-7-(3-methyl-1-buten-1-yl)-8-bromo-xanthine $R_f$ value: 0.65 (silica gel, methylene chloride/methanol=95:5)

Mass spectrum (ESI$^+$): m/z=468, 470 [M+H]$^+$ (154) 1-[(quinolin-7-yl)methyl]-3-methyl-7-(2-butyn-1-yl)-8-[3-(tert.-butyloxycarbonyl-amino)-piperidin-1-yl]-xanthine Mass spectrum (ESI$^+$): m/z=558 [M+H]$^+$ (155) 1-[([1,5]naphthyridin-2-yl)methyl]-3-methyl-7-(2-butyn-1-yl)-8-[3-(tert.-butyloxycarbonylamino)-piperidin-1-yl]-xanthine Mass spectrum (ESI$^+$): m/z=559 [M+H]$^+$ (156) 1-[(8-methyl-quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.45 (silica gel, methylene chloride/methanol=19:1)

Mass spectrum (ESI$^+$): m/z=573 [M+H]$^+$ (157) 1-[(2,3,8-trimethyl-quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.32 (silica gel, methylene chloride/methanol=96:4)

Mass spectrum (ESI$^+$): m/z=601 [M+H]$^+$ (158) 1-[([1,6]naphthyridin-5-yl)methyl]-3-methyl-7-(2-butyn-1-yl)-8-[3-(tert.-butyloxycarbonylamino)-piperidin-1-yl]-xanthine $R_f$ value: 0.20 (silica gel, ethyl acetate/methanol=98:2)

Mass spectrum (ESI$^+$): m/z=559 [M+H]$^+$ (159) 1-[([1,8]naphthyridin-2-yl)methyl]-3-methyl-7-(2-butyn-1-yl)-8-[3-(tert.-butyloxycarbonylamino)-piperidin-1-yl]-xanthine $R_f$ value: 0.12 (silica gel, ethyl acetate/methanol=98:2)

Mass spectrum (ESI$^+$): m/z=559 [M+H]$^+$ (160) 1-[(4-fluoro-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.47 (silica gel, petroleum ether/ethyl acetate=1:1)

Mass spectrum (ESI$^+$): m/z=575 [M+H]$^+$ (161) 1-[([1,5]naphthyridin-2-yl)methyl]-3-methyl-7-(2-butyn-1-yl)-8-[(R)-3-(tert.-butyloxycarbonylamino)-piperidin-1-yl]-xanthine $R_f$ value: 0.39 (silica gel, ethyl acetate)

Mass spectrum (ESI$^+$): m/z=559 [M+H]$^+$ (162) 1-[2-(3-methyl-2-oxo-2,3-dihydro-benzooxazol-4-yl)-2-oxo-ethyl]-3-methyl-7-(2-butyn-1-yl)-8-[(R)-3-(tert.-butyloxycarbonylamino)-piperidin-1-yl]-xanthine $R_f$ value: 0.60 (silica gel, methylene chloride/methanol=95:5)

Mass spectrum (ESI$^+$): m/z=606 [M+H]$^+$ (163) 1-[(8-phenyl-quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.48 (silica gel, methylene chloride/methanol=95:5)

Mass spectrum (ESI$^+$): m/z=356 [M+H]$^+$ (164) 1-[([1,5]naphthyridin-4-yl)methyl]-3-methyl-7-(2-butyn-1-yl)-8-[(R)-3-(tert.-butyloxycarbonylamino)-piperidin-1-yl]-xanthine $R_f$ value: 0.25 (silica gel, ethyl acetate/petroleum ether=4:1)

Mass spectrum (ESI$^+$): m/z=559 [M+H]$^+$ (165) 1-((E)-3-pentafluorophenyl-allyl)-3-methyl-7-(2-butyn-1-yl)-8-[(R)-3-(tert.-butyloxycarbonylamino)-piperidin-1-yl]-xanthine Mass spectrum (ESI$^+$): m/z=623 [M+H]$^+$ (166) 1-[(E)-3-(2-trifluoromethyl-phenyl)-allyl]-3-methyl-7-(2-butyn-1-yl)-8-[(R)-3-(tert.-butyloxycarbonylamino)-piperidin-1-yl]-xanthine Mass spectrum (ESI$^+$): m/z=601 [M+H]$^+$ (167) 1-[(E)-3-(3-trifluoromethyl-phenyl)-allyl]-3-methyl-7-(2-butyn-1-yl)-8-[(R)-3-(tert.-butyloxycarbonylamino)-piperidin-1-yl]-xanthine
Mass spectrum (ESI$^+$): m/z=601 [M+H]$^+$ (168) 1-[(E)-3-(4-trifluoromethyl-phenyl)-allyl]-3-methyl-7-(2-butyn-1-yl)-8-[(R)-3-(tert.-butyloxycarbonylamino)-piperidin-1-yl]-xanthine
Mass spectrum (ESI$^+$): m/z=601 [M+H]$^+$ (169) 1-[(3-trifluoromethyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.68 (silica gel, cyclohexane/ethyl acetate=3:7)
Mass spectrum (ESI$^+$): m/z=626 [M+H]$^+$ (170) 1-[(3-methyl-isoquinolin-1-yl)methyl]-3-methyl-7-(2-cyano-benzyl)-8-chloro-xanthine (171) 1-[(3-difluoromethyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.38 (silica gel, cyclohexane/ethyl acetate=1:1)
Mass spectrum (ESI$^+$): m/z=608 [M+H]$^+$ (172) 1-[(4-chloro-3-methoxy-isoquinolin-1-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/ethyl acetate=1:1)
Mass spectrum (ESI$^+$): m/z=622, 624 [M+H]$^+$ (173) 1-[(4-ethoxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.25 (silica gel, methylene chloride/ethyl acetate=1:1)
Mass spectrum (ESI$^+$): m/z=603 [M+H]$^+$ (174) 1-[(4-isopropyloxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.40 (silica gel, methylene chloride/ethyl acetate=1:1)
Mass spectrum (ESI$^+$): m/z=617 [M+H]$^+$ (175) 1-[(2-methyl-benzothiazol-6-yl)methyl]-3-methyl-7-(2-butyn-1-yl)-8-[3-(tert.-butyloxycarbonylamino)-piperidin-1-yl]-xanthine
$R_f$ value: 0.56 (silica gel, methylene chloride/ethyl acetate=1:1)
Mass spectrum (ESI$^+$): m/z=578 [M+H]$^+$ (176) 1-[(3-phenyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.75 (silica gel, methylene chloride/ethyl acetate=1:1)
Mass spectrum (ESI$^+$): m/z=634 [M+H]$^+$ (177) 1-[(4-phenyloxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.35 (silica gel, methylene chloride/ethyl acetate=1:1)
Mass spectrum (ESI$^+$): m/z=651 [M+H]$^+$ (178) 1-[(4-phenyl-quinazolin-2-yl)methyl]-3-cyclopropyl-7-(2-butyn-1-yl)-8-[3-(tert.-butyloxycarbonylamino)-piperidin-1-yl]-xanthine
$R_f$ value: 0.45 (silica gel, methylene chloride/ethyl acetate=1:1)
Mass spectrum (ESI$^+$): m/z=661 [M+H]$^+$ (179) 1-[(3-methyl-isoquinolin-1-yl)methyl]-3-cyclopropyl-7-(2-butyn-1-yl)-8-[3-(tert.-butyloxycarbonylamino)-piperidin-1-yl]-xanthine
$R_f$ value: 0.50 (silica gel, methylene chloride/ethyl acetate=1:1)
Mass spectrum (ESI$^+$): m/z=598 [M+H]$^+$ (180) 1-[2-(3-difluoromethoxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.77 (silica gel, methylene chloride/ethyl acetate=1:1)
Mass spectrum (ESI$^+$): m/z=601 [M+H]$^+$ (181) 1-[(2-phenyl-quinazolin-4-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/ethyl acetate=1:1)
Mass spectrum (ESI$^+$): m/z=635 [M+H]$^+$ (182) 1-[2-(2-methoxy-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.57 (silica gel, methylene chloride/ethyl acetate=1:1)
Mass spectrum (ESI$^+$): m/z=565 [M+H]$^+$ (183) 1-[2-(3-methoxy-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.63 (silica gel, methylene chloride/ethyl acetate=1:1)
Mass spectrum (ESI$^+$): m/z=565 [M+H]$^+$ (184) 1-[2-(3-trifluoromethoxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.64 (silica gel, methylene chloride/ethyl acetate=1:1)
Mass spectrum (ESI$^+$): m/z=619 [M+H]$^+$ (185) 1-[2-(biphenyl-2-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.70 (silica gel, methylene chloride/ethyl acetate=1:1)
Mass spectrum (ESI$^+$): m/z=611 [M+H]$^+$ (186) 1-[2-(biphenyl-3-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.75 (silica gel, methylene chloride/ethyl acetate=1:1)
Mass spectrum (ESI$^+$): m/z=611 [M+H]$^+$ (187) 1-[2-(3-isopropyloxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.66 (silica gel, methylene chloride/ethyl acetate=1:1)
Mass spectrum (ESI$^+$): m/z=593 [M+H]$^+$ (188) 1-[(3-methyl-isoquinolin-1-yl)methyl]-3-cyclopropyl-7-(2-butyn-1-yl)-8-[(R)-3-(tert.-butyloxycarbonylamino)-piperidin-1-yl]-xanthine
$R_f$ value: 0.50 (silica gel, methylene chloride/ethyl acetate=1:1)
Mass spectrum (ESI$^+$): m/z=598 [M+H]$^+$ (189) 1-[(4-phenyl-quinazolin-2-yl)methyl]-3-cyclopropyl-7-(2-butyn-1-yl)-8-[(R)-3-(tert.-butyloxycarbonylamino)-piperidin-1-yl]-xanthine
$R_f$ value: 0.50 (silica gel, methylene chloride/ethyl acetate=1:1)
Mass spectrum (ESI$^+$): m/z=661 [M+H]$^+$ (190) 1-[(4-cyano-naphthalen-1-yl)methyl]-3-cyclopropyl-7-(2-butyn-1-yl)-8-[(R)-3-(tert.-butyloxycarbonylamino)-piperidin-1-yl]-xanthine R$_f$ value: 0.75 (silica gel, methylene chloride/ethyl acetate=1:1)

Mass spectrum (ESI$^+$): m/z=608 [M+H]$^+$ (191) 1-[2-(2-phenyloxy-phenyl)-2-oxo-ethyl]-3-methyl-7-(2-butyn-1-yl)-8-[(R)-3-(tert.-butyloxycarbonylamino)-piperidin-1-yl]-xanthine R$_f$ value: 0.85 (silica gel, methylene chloride/ethyl acetate=1:1)

Mass spectrum (ESI$^+$): m/z=627 [M+H]$^+$ (192) 1-[2-(3-ethoxy-phenyl)-2-oxo-ethyl]-3-methyl-7-(2-butyn-1-yl)-8-[(R)-3-(tert.-butyloxycarbonylamino)-piperidin-1-yl]-xanthine R$_f$ value: 0.72 (silica gel, methylene chloride/ethyl acetate=1:1)

Mass spectrum (ESI$^+$): m/z=579 [M+H]$^+$ (193) 1-[2-(3-methoxy-phenyl)-2-oxo-ethyl]-3-methyl-7-(2-butyn-1-yl)-8-[(R)-3-(tert.-butyloxycarbonylamino)-piperidin-1-yl]-xanthine R$_f$ value: 0.67 (silica gel, methylene chloride/ethyl acetate=1:1)

Mass spectrum (ESI$^+$): m/z=565 [M+H]$^+$ (194) 1-[2-(2-methoxy-phenyl)-2-oxo-ethyl]-3-methyl-7-(2-butyn-1-yl)-8-[(R)-3-(tert.-butyloxycarbonylamino)-piperidin-1-yl)-xanthine R$_f$ value: 0.57 (silica gel, methylene chloride/ethyl acetate=1:1)

Mass spectrum (ESI$^+$): m/z=565 [M+H]$^+$ (195) 1-[(3-methyl-isoquinolin-1-yl)methyl]-3-methyl-7-(2-chloro-benzyl)-8-bromo-xanthine (196) 1-[(3-methyl-isoquinolin-1-yl)methyl]-3-methyl-7-(2-bromo-benzyl)-8-[(R)-3-(tert.-butyloxycarbonylamino)-piperidin-1-yl]-xanthine (197) 1-[(1,2,3,4-tetrahydro-phenanthridin-6-yl)methyl]-3-methyl-7-(2-butyn-1-yl)-8-[3-(tert.-butyloxycarbonylamino)-piperidin-1-yl]-xanthine R$_f$ value: 0.55 (silica gel, ethyl acetate/petroleum ether=2:1)

Mass spectrum (ESI$^+$): m/z=612 [M+H]$^+$

EXAMPLE VI 1-(2-{3-[(methanesulphinyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine To a solution of 402 mg of 1-(2-{3-[(methylsulphanyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine in 10 ml hexafluoroisopropanol are added 0.15 ml of a 35% hydrogen peroxide solution. The reaction mixture is stirred for half an hour at ambient temperature. Then 5 ml of a 10% sodium thiosulphate solution are added. The aqueous phase is extracted twice with 5 ml of methylene chloride. The combined extracts are dried over sodium sulphate and evaporated down. The yellow residue is purified by chromatography through a silica gel column with cyclohexane/ethyl acetate/methanol (5:4:1) as eluant.

Yield: 299 mg (73% of theory)

R$_f$ value: 0.28 (silica gel, cyclohexane/ethyl acetate/methanol=5:4:1)

Mass spectrum (ESI$^+$): m/z=643 [M+H]$^+$

The following compounds are obtained analogously to Example VI:

(1) 1-[2-(3-methanesulphinyl-phenyl)-2-oxo-ethyl]-3-methyl-7-(3-methyl-2-buten-1-yl)-8-[3-(tert.-butyloxycarbonylamino)-piperidin-1-yl]-xanthine R$_f$ value: 0.05 (silica gel, ethyl acetate/cyclohexane=3:1)

Mass spectrum (ESI$^+$): m/z=613 [M+H]$^+$ (2) 1-(2-{2-[(methanesulphinyl)methoxy]-phenyl}-2-oxo-ethyl)-3-methyl-7-(2-butyn-1-yl)-8-[3-(tert.-butyloxycarbonylamino)-piperidin-1-yl]-xanthine Mass spectrum (ESI$^+$): m/z=627 [M+H]$^+$

EXAMPLE VII

3-[(2-tri methylsilanyl-ethoxy)methyl]-7-(3-methyl-2-buten-1-yl)-8-[3-(tert.-butyloxycarbonylamino)-piperidin-1-yl]-xanthine 236 µl of 1,8-diazabicyclo[5.4.0]undec-7-ene are added dropwise to 630 mg of 7-(3-methyl-2-buten-1-yl)-8-[3-(tert.-butyloxycarbonylamino)-piperidin-1-yl]-xanthine in 11 ml of acetonitrile. The solution is stirred for two hours at ambient temperature, then the acetonitrile is distilled off in vacuo. The flask residue is taken up in 11 ml of N,N-dimethylformamide and combined with 258 mg of (2-trimethylsilanyl-ethoxy) methyl chloride. The reaction mixture is stirred for three hours at 120° C. For working up water is added, the precipitate formed is filtered off and taken up in ethyl acetate. The solution is dried over magnesium sulphate, evaporated down and chromatographed through a silica gel column with cyclohexane/ethyl acetate/methanol (6:1:0 to 0:5:1) as eluant.

Yield: 435 mg (53% of theory)

Mass spectrum (ESI$^+$): m/z=549 [M+H]$^+$

The following compounds are obtained analogously to Example VII:

(1) 3-[(2-trimethylsilanyl-ethoxy)methyl]-7-(2-cyano-benzyl)-xanthine

Mass spectrum (ESI$^-$): m/z=396 [M-H]$^-$ (2) 3-[(methoxycarbonyl)methyl]-7-(3-methyl-2-buten-1-yl)-8-[3-(tert.-butyloxy-carbonylamino)-piperidin-1-yl]-xanthine R$_f$ value: 0.31 (silica gel, methylene chloride/methanol/conc. aqueous ammonia=90:10:1)

Mass spectrum (ESI$^+$): m/z=491 [M+H]$^+$

EXAMPLE VIII 7-(3-methyl-2-buten-1-yl)-8-[3-(tert.-butyloxycarbonylamino)-piperidin-1-yl]-xanthine 510 mg of potassium-tert. butoxide are added to 2.32 g of 2-[3-(tert.-butyloxycarbonylamino)-piperidin-1-yl]-3-(3-methyl-2-buten-1-yl)-4-ethoxycarbonyl-5-{[(ethoxycarbonylamino)carbonyl]amino}-3H-imidazole in 35 ml of ethanol. The yellow solution is refluxed for five hours. After cooling to ambient temperature it is diluted with methylene chloride. The organic phase is washed with saturated ammonium chloride solution and saturated sodium chloride solution, dried over magnesium sulphate and evaporated down. The crude product is purified by chromatography through a silica gel column with methylene chloride/methanol/conc. methanolic ammonia (95:5:1 to 90:10:1) as eluant.

Yield: 630 mg (35% of theory)

R$_f$ value: 0.24 (silica gel, methylene chloride/methanol/conc. aqueous ammonia=90:10:1)

Mass spectrum (ESI$^+$): m/z=419 [M+H]$^+$

EXAMPLE IX

2-[3-(tert.-butyloxycarbonylamino)-piperidin-1-yl]-3-(3-methyl-2-buten-1-yl)-4-ethoxycarbonyl-5-{[(ethoxycarbonylamino)carbonyl]amino}-3H-imidazole 2.97 ml of ethyl isocanatoformate are added to 4.00 g of 2-[3-(tert.-butyloxycarbonylamino)-piperidin-1-yl]-3-(3-methyl-2-buten-1-yl)-4-ethoxycarbonyl-5-amino-3H-imidazole in 90 ml of 1,2-dimethoxyethane and the light brown solution is heated overnight at 120° C. in an oil bath. Then a further 0.6 ml of ethyl isocyanatoformate is added and heating is continued for a further four hours. For working up the reaction mixture is combined with saturated potassium carbonate solution and extracted with ethyl acetate. The organic phase is dried over magnesium sulphate, evaporated down and purified through a silica gel column with methylene chloride/methanol/conc. methanolic ammonia (98:2:1 to 90:10:1) as eluant.

Yield: 2.27 g (45% of theory)

$R_f$ value: 0.29 (silica gel, methylene chloride/methanol/conc. aqueous ammonia=90:10:1)

Mass spectrum (ESI$^+$): m/z=537 [M+H]$^+$

EXAMPLE X

2-[3-(tert.-butyloxycarbonylamino)-piperidin-1-yl]-3-(3-methyl-2-buten-1-yl)-4-ethoxycarbonyl-5-amino-3H-imidazole Prepared by refluxing cyanimino-[N-(3-methyl-2-buten-1-yl)-N-(ethoxy-carbonylmethyl)-amino]-[3-(tert.-butyloxycarbonylamino)-piperidin-1-yl]-methane with sodium in ethanol.

$R_f$ value: 0.26 (aluminium oxide, ethyl acetate/petroleum ether=8:2)

Mass spectrum (ESI$^+$): m/z=422 [M+H]$^+$

EXAMPLE XI

Cyanimino-[N-(3-methyl-2-buten-1-yl)-N-(ethoxy-carbonylmethyl)-amino]-[3-(tert.-butyloxycarbonylamino)-piperidin-1-yl]-methane Prepared by reacting cyanimino-[N-(3-methyl-2-buten-1-yl)-N-(ethoxy-carbonylmethyl)-amino]-phenyloxy-methane with 3-(tert.-butyloxycarbonylamino)-piperidine in the presence of potassium carbonate in N,N-dimethylformamide at ambient temperature.

$R_f$ value: 0.10 (silica gel, petroleum ether/ethyl acetate=6:4)

Mass spectrum (ESI$^+$): m/z=422 [M+H]$^+$

EXAMPLE XII cyanimino-[N-(3-methyl-2-buten-1-yl)-N-(ethoxy-carbonylmethyl)-amino]-phenyloxy-methane Prepared by reacting cyanimino-[(ethoxycarbonylmethyl)amino]-phenyloxy-methane with 1-bromo-3-methyl-2-butene in the presence of potassium carbonate in acetone at ambient temperature.

$R_f$ value: 0.70 (silica gel, cyclohexane/ethyl acetate=1:1)

Mass spectrum (ESI$^+$): m/z=316 [M+H]$^+$

EXAMPLE XIII cyanimino-[(ethoxycarbonylmethyl)amino]-phenyloxy-methan

Prepared by reacting diphenylcyanocarbonimidate with ethyl aminoacetate-hydrochloride in the presence of triethylamine in isopropanol at ambient temperature (analogously to R. Besse et al., *Tetrahedron* 1990, 46, 7803-7812).

$R_f$ value: 0.73 (silica gel, petroleum ether/ethyl acetate=8:2)

Mass spectrum (ESI$^+$): m/z=248 [M+H]$^+$

EXAMPLE XIV 1-methyl-3-[(methoxycarbonyl)methyl]-7-(2-cyano-benzyl)-8-chloro-xanthine Prepared by reacting 1-methyl-7-(2-cyano-benzyl)-8-chloro-xanthine with methyl bromoacetate in the presence of potassium carbonate in N,N-dimethylformamide at ambient temperature.

$R_f$ value: 0.80 (silica gel, methylene chloride/methanol=9:1)

Mass spectrum (ESI$^+$): m/z=388, 390 [M+H]$^+$

The following compounds are obtained analogously to Example XIV:

(1) 1-methyl-3-cyanomethyl-7-(2-cyano-benzyl)-8-chloro-xanthine

Mass spectrum (ESI$^+$): m/z=355, 357 [M+H]$^+$ (2) 1-methyl-3-(2-propyn-1-yl)-7-(2-cyano-benzyl)-8-chloro-xanthine $R_f$ value: 0.80 (silica gel, methylene chloride/methanol=95:5)

Mass spectrum (ESI$^+$): m/z=354, 356 [M+H]$^+$ (3) 1-methyl-3-(2-propen-1-yl)-7-(2-cyano-benzyl)-8-chloro-xanthine $R_f$ value: 0.90 (silica gel, methylene chloride/methanol=95:5)

Mass spectrum (ESI$^+$): m/z=356, 358 [M+H]$^+$ (4) 1-(2-phenyl-2-oxo-ethyl)-3-cyanomethyl-7-(3-methyl-2-buten-1-yl)-8-[3-(tert.-butyloxycarbonylamino)-piperidin-1-yl]-xanthine $R_f$ value: 0.78 (silica gel, methylene chloride/methanol/conc. aqueous ammonia=90:10:1)

Mass spectrum (ESI$^+$): m/z=576 [M+H]$^+$ (5) 1-methyl-3-isopropyl-7-(2-cyano-benzyl)-8-chloro-xanthine Mass spectrum (ESI$^+$): m/z=358, 360 [M+H]$^+$

EXAMPLE XV 1-methyl-7-(2-cyano-benzyl)-8-chloro-xanthine

Prepared by treating 1-methyl-3-[(2-trimethylsilanylethoxy)methyl]-7-(2-cyano-benzyl)-8-chloro-xanthine with trifluoroacetic acid in methylene chloride at ambient temperature.

$R_f$ value: 0.50 (silica gel, methylene chloride/methanol=9:1)

Mass spectrum (ESI$^+$): m/z=316, 318 [M+H]$^+$

The following compounds are obtained analogously to Example XV:

(1) 1-(2-phenyl-2-oxo-ethyl)-3-methyl-8-bromo-xanthine $R_f$ value: 0.26 (silica gel, methylene chloride/methanol=95:5)

Mass spectrum (ESI$^-$): m/z=361, 363 [M-H]

(2) 1-[(4-oxo-3,4-dihydro-phthalazin-1-yl)methyl]-3-methyl-7-(3-methyl-2-buten-1-yl)-8-(3-amino-piperidin-1-yl)-xanthine (As the compound still contains impurities which cannot be removed by chromatography, the material is again converted into the BOC-protected derivative and then purified by chromatography, cf. Ex. XXV(1).)

Mass spectrum (ESI$^+$): m/z=491 [M+H]$^+$

EXAMPLE XVI 1-methyl-3-[(2-tri methylsilanyl-ethoxy)methyl]-7-(2-cyano-benzyl)-8-chloro-xanthine Prepared by chlorination of 1-methyl-3-[(2-trimethylsilanyl-ethoxy)methyl]-7-(2-cyano-benzyl)-xanthine with N-chlorosuccinimide in dichloroethane while refluxing.

Mass spectrum (EI): m/z=445, 447 [M]+

EXAMPLE XVII 7-(2-cyano-benzyl)-xanthine

Prepared by treating 16.68 g of 2-amino-7-(2-cyano-benzyl)-1,7-dihydro-purin-6-one with 17.00 g of sodium nitrite in a mixture of 375 ml of conc. acetic acid, 84 ml of water and 5.2 ml of conc. hydrochloric acid at 50° C.

Yield: 8.46 g (50% of theory)

Mass spectrum (ESI$^+$): m/z=268 [M+H]$^+$

EXAMPLE XVIII 2-amino-7-(2-cyano-benzyl)-1,7-dihydro-purin-6-one

Prepared by reacting 20.00 g of guanosine-hydrate with 22.54 g of 2-cyano-benzylbromide in dimethylsulphoxide at 60° C. and subsequent treatment with 57 ml of conc. hydrochloric acid.

Yield: 18.00 g (97% of theory)

Mass spectrum (ESI$^+$): m/z=267 [M+H]$^+$

EXAMPLE XIX

1-{2-[3-(2-oxo-imidazolidin-1-yl)-phenyl]-2-oxo-ethyl}-3-methyl-7-(3-methyl-2-buten-1-yl)-8-[3-(tert.-butyloxycarbonylamino)-piperidin-1-yl]-xanthine Prepared by treating 1-[2-(3-{[(2-chloro-ethylamino)carbonyl]amino}-phenyl)-2-oxo-ethyl]-3-methyl-7-(3-methyl-2-buten-1-yl)-8-[3-(tert.-butyloxy-carbonylamino)-piperidin-1-yl]-xanthine with potassium-tert. butoxide in N,N-dimethylformamide at ambient temperature.

R$_f$ value: 0.50 (silica gel, methylene chloride/methanol=9:1)

EXAMPLE XX

1-[2-(3-{[(2-chloro-ethylamino)carbonyl]amino}-phenyl)-2-oxo-ethyl]-3-methyl-7-(3-methyl-2-buten-1-yl)-8-[3-(tert.-butyloxycarbonylamino)-piperidin-1-yl]-xanthine Prepared by reacting 221 mg of 1-[2-(3-amino-phenyl)-2-oxo-ethyl]-3-methyl-7-(3-methyl-2-buten-1-yl)-8-[3-(tert.-butyloxycarbonylamino)-piperidin-1-yl]-xanthine with 60 μl of 2-chloroethyl isocyanate in 3 ml methylene chloride at ambient temperature.

Yield: 163 mg (64% of theory)

R$_f$ value: 0.20 (silica gel, cyclohexane/ethyl acetate/methanol=6:3:1)

Mass spectrum (ESI$^+$): m/z=671, 673 [M+H]$^+$

The following compounds are obtained analogously to Example XX:

(1) 1-[2-(2-{[(ethoxycarbonylamino)carbonyl]amino}-phenyl)-2-oxo-ethyl]-3-methyl-7-(3-methyl-2-buten-1-yl)-8-[3-(tert.-butyloxycarbonylamino)-piperidin-1-yl]-xanthine (Carried out in N,N-dimethylformamide at 30° C.)

R$_f$ value: 0.26 (silica gel, cyclohexane/ethyl acetate=4:6)

Mass spectrum (ESI$^+$): m/z=681 [M+H]$^+$

EXAMPLE XXI

1-[2-(3-amino-phenyl)-2-oxo-ethyl]-3-methyl-7-(3-methyl-2-buten-1-yl)-8-[3-(tert.-butyloxycarbonylamino)-piperidin-1-yl]-xanthine Prepared by treating 1-[2-(3-nitro-phenyl)-2-oxo-ethyl]-3-methyl-7-(3-methyl-2-buten-1-yl)-8-[3-(tert.-butyloxycarbonylamino)-piperidin-1-yl]-xanthine with iron powder in a mixture of ethanol, water and glacial acetic acid (80:25:10) at 100° C.

R$_f$ value: 0.55 (silica gel, cyclohexane/ethyl acetate/methanol/conc. aqueous ammonia=50:30:20:1)

Mass spectrum (ESI$^+$): m/z=566 [M+H]$^+$

The following compounds are obtained analogously to Example XXI:

(1) 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine Mass spectrum (ESI$^+$): m/z=566 [M+H]$^+$ (2) 1-[2-(2-amino-phenyl)-2-oxo-ethyl]-3-methyl-7-(3-methyl-2-buten-1-yl)-8-[(S)-3-(tert.-butyloxycarbonylamino)-piperidin-1-yl]-xanthine Mass spectrum (ESI$^+$): m/z=566 [M+H]$^+$ (3) 1-[(5-amino-isoquinolin-1-yl)methyl]-3-methyl-7-(3-methyl-2-buten-1-yl)-8-[3-(tert.-butyloxycarbonylamino)-piperidin-1-yl]-xanthine R$_f$ value: 0.22 (silica gel, ethyl acetate)

Mass spectrum (ESI$^+$): m/z=589 [M+H]$^+$ (4) 1-[2-(2-amino-phenyl)-2-oxo-ethyl]-3-methyl-7-[(1-cyclopenten-1-yl)methyl]-8-bromo-xanthine Mass spectrum (ESI$^+$): m/z=458, 460 [M+H]$^+$ (5) 1-[2-(2-amino-phenyl)-2-oxo-ethyl]-3-methyl-7-((E)-2-buten-1-yl)-8-bromo-xanthine (product contains approx. 10% of Z isomer)

R$_f$ value: 0.55 (silica gel, cyclohexane/ethyl acetate=4:6)

Mass spectrum (ESI$^+$): m/z=432, 434 [M+H]$^+$ (6) 1-[2-(2-amino-phenyl)-2-oxo-ethyl]-3-methyl-7-(2-butyn-1-yl)-8-bromo-xanthine R$_f$ value: 0.50 (silica gel, methylene chloride/methanol=95:5)

Mass spectrum (ESI$^+$): m/z=430, 432 [M+H]$^+$ (7) 1-[2-(2-amino-phenyl)-2-oxo-ethyl]-3-methyl-7-((E)-2-buten-1-yl)-8-[(R)-3-(tert.-butyloxycarbonylamino)-piperidin-1-yl]-xanthine Mass spectrum (ESI$^+$): m/z=552 [M+H]$^+$ (8) 1-[2-(2-amino-phenyl)-2-oxo-ethyl]-3-methyl-7-((E)-2-buten-1-yl)-8-[(S)-3-(tert.-butyloxycarbonylamino)-piperidin-1-yl]-xanthine Mass spectrum (ESI$^+$): m/z=552 [M+H]$^+$ (9) 1-[2-(2-amino-3-methoxy-phenyl)-2-oxo-ethyl]-3-methyl-7-(3-methyl-2-buten-1-yl)-8-[3-(tert.-butyloxycarbonylamino)-piperidin-1-yl]-xanthine $R_f$ value: 0.82 (silica gel, ethyl acetate/petroleum ether=4:1)

Mass spectrum (ESI$^+$): m/z=596 [M+H]$^+$

EXAMPLE XXII 1-(2-{2-[(ethylcarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine Prepared by reacting 248 mg of 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine with 40 μl of propionic acid chloride in the presence of 60 μl of pyridine in N,N-dimethylformamide at 80° C.

Yield: 168 mg (62% of theory)

$R_f$ value: 0.55 (silica gel, cyclohexane/ethyl acetate=3:7)

Mass spectrum (ESI$^+$): m/z=622 [M+H]$^+$

The following compounds are obtained analogously to Example XXII:

(1) 1-({5-[(methoxycarbonyl)methylamino]-isoquinolin-1-yl}methyl)-3-methyl-7-(3-methyl-2-buten-1-yl)-8-[3-(tert.-butyloxycarbonylamino)-piperidin-1-yl]-xanthine (Carried out with methyl bromoacetate and potassium carbonate)

$R_f$ value: 0.42 (silica gel, methylene chloride/methanol=95:5)

Mass spectrum (ESI$^+$): m/z=661 [M+H]$^+$ (2) 1-[2-(2-acetylamino-phenyl)-2-oxo-ethyl]-3-methyl-7-((E)-2-buten-1-yl)-8-[3-(tert.-butyloxycarbonylamino)-piperidin-1-yl]-xanthine (product contains approx. 10% of Z isomer)

Mass spectrum (ESI$^+$): m/z=594 [M+H]$^+$ (3) 1-(2-{2-[(isopropylcarbonyl)amino]-phenyl}-2-oxo-ethyl)-3-methyl-7-((E)-2-buten-1-yl)-8-[3-(tert.-butyloxycarbonylamino)-piperidin-1-yl]-xanthine (product contains approx. 10% of Z isomer)

Mass spectrum (ESI$^+$): m/z=622 [M+H]$^+$ (4) 1-[2-(2-acetylamino-phenyl)-2-oxo-ethyl]-3-methyl-7-(3-methyl-2-buten-1-yl)-8-[(S)-3-(tert.-butyloxycarbonylamino)-piperidin-1-yl]-xanthine $R_f$ value: 0.50 (silica gel, cyclohexane/ethyl acetate=3:7)

Mass spectrum (ESI$^+$): m/z=608 [M+H]$^+$ (5) 1-[2-(2-acetylamino-phenyl)-2-oxo-ethyl]-3-methyl-7-(2-butyn-1-yl)-8-[3-(tert.-butyloxycarbonylamino)-piperidin-1-yl]-xanthine $R_f$ value: 0.34 (silica gel, cyclohexane/ethyl acetate=3:7)

Mass spectrum (ESI$^+$): m/z=592 [M+H]$^+$ (6) 1-(2-{2-[(isopropylcarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine $R_f$ value: 0.25 (silica gel, cyclohexane/ethyl acetate=1:1)

Mass spectrum (ESI$^+$): m/z=636 [M+H]$^+$ (7) 1-(2-{2-[(isopropylcarbonyl)amino]-phenyl}-2-oxo-ethyl)-3-methyl-7-(2-butyn-1-yl)-8-[3-(tert.-butyloxycarbonylamino)-piperidin-1-yl]-xanthine $R_f$ value: 0.44 (silica gel, methylene chloride/methanol=95:5)

Mass spectrum (ESI$^+$): m/z=620 [M+H]$^+$ (8) 1-[2-(2-acetylamino-phenyl)-2-oxo-ethyl]-3-methyl-7-(2-butyn-1-yl)-8-[(S)-3-(tert.-butyloxycarbonylamino)-piperidin-1-yl]-xanthine $R_f$ value: 0.34 (silica gel, cyclohexane/ethyl acetate=3:7)

Mass spectrum (ESI$^+$): m/z=592 [M+H]$^+$ (9) 1-(2-{2-[(isopropylcarbonyl)amino]-phenyl}-2-oxo-ethyl)-3-methyl-7-(2-butyn-1-yl)-8-[(S)-3-(tert.-butyloxycarbonylamino)-piperidin-1-yl]-xanthine $R_f$ value: 0.44 (silica gel, methylene chloride/methanol=95:5)

Mass spectrum (ESI$^+$): m/z=620 [M+H]$^+$

(10) 1-(2-{2-[(methoxycarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine (Carried out in acetonitrile at 55° C.)

$R_f$ value: 0.25 (silica gel, cyclohexane/ethyl acetate=1:1)

Mass spectrum (ESI$^+$): m/z=624 [M+H]$^+$

(11) 1-(2-{2-[(isopropylcarbonyl)amino]-phenyl}-2-oxo-ethyl)-3-methyl-7-((E)-2-buten-1-yl)-8-[(S)-3-(tert.-butyloxycarbonylamino)-piperidin-1-yl]-xanthine (Carried out in acetonitrile at 65° C.)

$R_f$ value: 0.50 (silica gel, cyclohexane/ethyl acetate/isopropanol=14:3:3)

Mass spectrum (ESI$^+$): m/z=622 [M+H]$^+$

(12) 1-(2-{2-[(ethylcarbonyl)amino]-phenyl}-2-oxo-ethyl)-3-methyl-7-((E)-2-buten-1-yl)-8-[(R)-3-(tert.-butyloxycarbonylamino)-piperidin-1-yl]-xanthine Mass spectrum (ESI$^+$): m/z=608 [M+H]$^+$

(13) 1-[2-(2-acetylamino-phenyl)-2-oxo-ethyl]-3-methyl-7-((E)-2-buten-1-yl)-8-[(R)-3-(tert.-butyloxycarbonylamino)-piperidin-1-yl]-xanthine Mass spectrum (ESI$^+$): m/z=594 [M+H]$^+$

(14) 1-[2-(2-acetylamino-phenyl)-2-oxo-ethyl]-3-methyl-7-((E)-2-buten-1-yl)-8-[(S)-3-(tert.-butyloxycarbonylamino)-piperidin-1-yl]-xanthine $R_f$ value: 0.28 (silica gel, cyclohexane/ethyl acetate/isopropanol=8:1:1)

Mass spectrum (ESI$^+$): m/z=594 [M+H]$^+$

(15) 1-(2-{2-[(isopropylcarbonyl)amino]-phenyl}-2-oxo-ethyl)-3-methyl-7-(2-butyn-1-yl)-8-[(R)-3-(tert.-butyloxycarbonylamino)-piperidin-1-yl]-xanthine $R_f$ value: 0.90 (silica gel, methylene chloride/methanol=9:1)

(16) 1-(2-{2-[(isopropylcarbonyl)amino]-phenyl}-2-oxo-ethyl)-3-methyl-7-((E)-2-buten-1-yl)-8-[(R)-3-(tert.-butyloxycarbonylamino)-piperidin-1-yl])-xanthine (Carried out in 1,2-dichloroethane at 45° C.)

$R_f$ value: 0.30 (silica gel, cyclohexane/ethyl acetate/isopropanol=8:1:1)

Mass spectrum (ESI$^+$): m/z=622 [M+H]$^+$

(17) 1-(2-{2-[(ethylcarbonyl)amino]-phenyl}-2-oxo-ethyl)-3-methyl-7-((E)-2-buten-1-yl)-8-[(S)-3-(tert.-butyloxycarbonylamino)-piperidin-1-yl]-xanthine $R_f$ value: 0.48 (silica gel, cyclohexane/ethyl acetate/isopropanol=14:3:3)

Mass spectrum (ESI$^+$): m/z=608 [M+H]$^+$

(18) 1-(2-{2-[(ethylcarbonyl)amino]-phenyl}-2-oxo-ethyl)-3-methyl-7-(2-butyn-1-yl)-8-[(R)-3-(tert.-butyloxycarbonylamino)-piperidin-1-yl]-xanthine Mass spectrum (ESI$^+$): m/z=606 [M+H]$^+$

(19) 1-(2-{2-[(ethylcarbonyl)amino]-phenyl}-2-oxo-ethyl)-3-methyl-7-(2-butyn-1-yl)-8-[(S)-3-(tert.-butyloxycarbonylamino)-piperidin-1-yl]-xanthine $R_f$ value: 0.22 (silica gel, methylene chloride/methanol=95:5)

(20) 1-(2-{2-[(phenylcarbonyl)amino]-phenyl}-2-oxo-ethyl)-3-methyl-7-((E)-2-buten-1-yl)-8-[3-(tert.-butyloxycarbonylamino)-piperidin-1-yl]-xanthine R$_f$ value: 0.55 (silica gel, cyclohexane/ethyl acetate/isopropanol=14:3:3)

Mass spectrum (ESI$^+$): m/z=656 [M+H]$^+$

(21) 1-(2-{2-[(cyclopropylcarbonyl)amino]-phenyl}-2-oxo-ethyl)-3-methyl-7-[(1-cyclopenten-1-yl)methyl]-8-[3-(tert.-butyloxycarbonylamino)-piperidin-1-yl]-xanthine (Carried out with Hünig base and 4-dimethylamino-pyridine in methylene chloride)

R$_f$ value: 0.60 (silica gel, methylene chloride/methanol=18:1)

EXAMPLE XXIII 1-(2-{3-[(methoxycarbonyl)methoxy]-phenyl}-2-oxo-ethyl)-3-methyl-7-(3-methyl-2-buten-1-yl)-8-(3-amino-piperidin-1-yl)-xanthine Prepared by treating 1-(2-{3-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine with trifluoroacetic acid in methylene chloride at ambient temperature.

Mass spectrum (ESI$^+$): m/z=539 [M+H]$^+$

The following compounds are obtained analogously to Example XXIII:
(1) 1-(2-{2-[(methoxycarbonyl)methoxy]-phenyl}-2-oxo-ethyl)-3-methyl-7-(3-methyl-2-buten-1-yl)-8-(3-amino-piperidin-1-yl)-xanthine Mass spectrum (ESI$^+$): m/z=539 [M+H]$^+$

EXAMPLE XXIV 1-methyl-3-phenyl-7-(2-cyano-benzyl)-8-chloro-xanthine

A mixture of 829 mg of 1-methyl-7-(2-cyano-benzyl)-8-chloro-xanthine, 640 mg of phenylboric acid, 509 mg of anhydrous copper acetate and 0.43 ml of pyridine in 20 ml methylene chloride is stirred for four days at ambient temperature in the presence of 100 mg of 4 Å molecular sieves. Then another 320 mg of phenylboric acid are added and the reaction mixture is stirred for another day at ambient temperature. For working up the mixture is filtered through talc and washed with ethyl acetate. The filtrate is evaporated down and chromatographed through a silica gel column with cyclohexane/ethyl acetate (7:3 to 1:1) as eluant.

Yield: 142 mg (14% of theory)

Mass spectrum (ESI$^+$): m/z=392, 394 [M+H]$^+$

EXAMPLE XXV 1-(2-phenyl-2-oxo-ethyl)-7-(3-methyl-2-buten-1-yl)-8-[3-(tert.-butyloxycarbonyl-amino)-piperidin-1-yl]-xanthine Prepared by reacting 1-(2-phenyl-2-oxo-ethyl)-7-(3-methyl-2-buten-1-yl)-8-(3-amino-piperidin-1-yl)-xanthine with di-tert.butyl pyrocarbonate in the presence of Hünig base in methylene chloride at ambient temperature.

R$_f$ value: 0.27 (silica gel, methylene chloride/methanol/conc. aqueous ammonia=90:10:1)

The following compounds are obtained analogously to Example XXV:
(1) 1-[(4-oxo-3,4-dihydro-phthalazin-1-yl)methyl]-3-methyl-7-(3-methyl-2-buten-1-yl)-8-[3-(tert.-butyloxycarbonyl-amino)-piperidin-1-yl]-xanthine R$_f$ value: 0.27 (silica gel, methylene chloride/methanol=95:5)

Mass spectrum (ESI$^+$): m/z=591 [M+H]$^+$ (2) 7-acetyl-1-(tert.-butyloxycarbonyl)-1H-indole R$_f$ value: 0.82 (silica gel, methylene chloride/petroleum ether/ethyl acetate=5:4:1)

Mass spectrum (ESI$^+$): m/z=260 [M+H]$^+$

EXAMPLE XXVI

1-[(cinnolin-4-yl)methyl]-3-methyl-7-(3-methyl-2-buten-1-yl)-8-chloro-xanthine and 1-[(1,4-di hydro-cinnolin-4-yl)methyl]-3-methyl-7-(3-methyl-2-buten-1-yl)-8-chloro-xanthine 510 mg of a mixture of (cinnolin-4-yl)-methanol and (1,4-dihydro-cinnolin-4-yl)-methanol (see Ex. XXVII) are added to 830 mg of 3-methyl-7-(3-methyl-2-buten-1-yl)-8-chloro-xanthine and 1.25 g of triphenylphosphine in 25 ml of tetrahydrofuran. The reaction mixture is combined with 0.92 ml diethyl azodicarboxylate and stirred overnight at ambient temperature. Then it is evaporated down and chromatographed through a silica gel column with ethyl acetate/petroleum ether (7:3 to 0:1) as eluant. A mixture of cinnoline and 1,4-dihydro-cinnoline compound is obtained.

Yield: 660 mg (52% of theory)

R$_f$ value: 0.60 (silica gel, ethyl acetate/petroleum ether=7:3)

The following compounds are obtained analogously to Example XXVI:
(1) 1-({4-oxo-3-[(2-tri methylsilanyl-ethoxy)methyl]-3,4-dihydro-phthalazin-1-yl}methyl)-3-methyl-7-(3-methyl-2-buten-1-yl)-8-chloro-xanthine R$_f$ value: 0.85 (silica gel, methylene chloride/methanol=95:5)

Mass spectrum (ESI$^+$): m/z=557, 559 [M+H]$^+$ (2) 1-[(isoquinolin-3-yl)methyl]-3-methyl-7-(3-methyl-2-buten-1-yl)-8-chloro-xanthine Melting point: 194-195° C.

Mass spectrum (ESI$^+$): m/z=410, 412 [M+H]$^+$ (3) 1-[(3-methyl-4-oxo-3,4-di hydro-phthalazin-1-yl)methyl]-3-methyl-7-(3-methyl-2-buten-1-yl)-8-chloro-xanthine R$_f$ value: 0.66 (silica gel, ethyl acetate)

Mass spectrum (ESI$^+$): m/z=441, 443 [M+H]$^+$ (4) 1-[(quinolin-4-yl)methyl]-3-methyl-7-(2-butyn-1-yl)-8-bromo-xanthine (Carried out with potassium carbonate)

R$_f$ value: 0.45 (silica gel, ethyl acetate)

Mass spectrum (ESI$^+$): m/z=438, 440 [M+H]$^+$ (5) 1-[(isoquinolin-1-yl)methyl]-3-methyl-7-(2-butyn-1-yl)-8-bromo-xanthine R$_f$ value: 0.78 (silica gel, ethyl acetate)

Mass spectrum (ESI$^+$): m/z=438, 440 [M+H]$^+$ (6) 1-[(4-dimethylamino-naphthalen-1-yl)methyl]-3-methyl-7-(2-butyn-1-yl)-8-[3-(tert.-butyloxycarbonylamino)-piperidin-1-yl]-xanthine R$_f$ value: 0.80 (silica gel, ethyl acetate)

Mass spectrum (ESI$^+$): m/z=600 [M+H]$^+$ (7) 1-[(isoquinolin-1-yl)methyl]-3-methyl-7-((E)-2-buten-1-yl)-8-bromo-xanthine (The product contains approx. 20% of Z isomer)

$R_f$ value: 0.71 (silica gel, ethyl acetate)

Mass spectrum (ESI$^+$): m/z=440, 442 [M+H]$^+$ (8) 1-[(1-methyl-1H-indol-2-yl)methyl]-3-methyl-7-(2-butyn-1-yl)-8-bromo-xanthine $R_f$ value: 0.95 (silica gel, methylene chloride/methanol=95:5)

Mass spectrum (ESI$^+$): m/z=440, 442 [M+H]$^+$ (9) 1-[(quinolin-3-yl)methyl]-3-methyl-7-(2-butyn-1-yl)-8-bromo-xanthine $R_f$ value: 0.55 (silica gel, ethyl acetate/petroleum ether=8:2)

Mass spectrum (ESI$^+$): m/z=438, 440 [M+H]$^+$

(10) 1-{[1-(tert.-butyloxycarbonylamino)-1H-indol-2-yl]methyl}-3-methyl-7-(2-butyn-1-yl)-8-bromo-xanthine $R_f$ value: 0.74 (silica gel, petroleum ether/ethyl acetate=1:1)

Mass spectrum (ESI$^+$): m/z=526, 528 [M+H]$^+$

(11) 1-({2-methyl-1-[(2-trimethylsilanyl-ethoxy)methyl]-1H-benzoimidazol-5-yl}methyl)-3-methyl-7-(2-butyn-1-yl)-8-bromo-xanthine (mixed with 1-({2-methyl-3-[(2-trimethylsilanyl-ethoxy)methyl]-3H-benzoimidazol-5-yl}methyl)-3-methyl-7-(2-butyn-1-yl)-8-bromo-xanthine)

Mass spectrum (ESI$^+$): m/z=571, 573 [M+H]$^+$

(12) 1-[(1-[(2-trimethylsilanyl-ethoxy)methyl]-1H-benzoimidazol-5-yl)methyl]-3-methyl-7-(2-butyn-1-yl)-8-bromo-xanthine (mixed with 1-[(3-[(2-tri methylsilanyl-ethoxy)methyl]-3H-benzoimidazol-5-yl)methyl]-3-methyl-7-(2-butyn-1-yl)-8-bromo-xanthine)

$R_f$ value: 0.50 (silica gel, methylene chloride/methanol=95:5)

Mass spectrum (ESI$^+$): m/z=557, 559 [M+H]$^+$

(13) 1-[(pyrazolo[1,5-a]pyridin-2-yl)methyl]-3-methyl-7-(2-butyn-1-yl)-8-bromo-xanthine $R_f$ value: 0.35 (silica gel, petroleum ether/ethyl acetate=1:2)

Mass spectrum (ESI$^+$): m/z=427, 429 [M+H]$^+$

EXAMPLE XXVII (cinnolin-4-yl)-methanol and (1,4-dihydro-cinnolin-4-yl)-methanol A solution of 1.00 g of methyl cinnolin-4-carboxylate in 15 ml diethyl ether is added dropwise at 0° C. to a suspension of 222 mg of lithium aluminium hydride in 5 ml of diethyl ether. After 1.5 hours water is carefully added dropwise to the reaction mixture, this is stirred with methylene chloride and suction filtered through a glass fibre filter. The aqueous phase is extracted with methylene chloride and the combined organic phases are dried over magnesium sulphate and evaporated down. According to $^1$H-NMR a mixture of cinnoline and 1,4-dihydro-cinnoline compound is obtained as a yellow oil which is reacted further without any more purification.

Yield: 530 mg (62% of theory)

$R_f$ value: 0.63 (silica gel, ethyl acetate)

Mass spectrum (ESI$^+$): m/z=161 [M1+H]$^+$ $^{and}$ 163 [M2+H]$^+$

The following compounds are obtained analogously to Example XXVII:

(1) {2-methyl-1-[(2-trimethylsilanyl-ethoxy)methyl]-1H-benzoimidazol-5-yl}-methanol (mixed with {2-methyl-3-[(2-trimethylsilanyl-ethoxy)methyl]-3H-benzoimidazol-5-yl}-methanol)

Mass spectrum (ESI$^+$): m/z=293 [M+H]$^+$ (2) (2,3,8-trimethyl-quinoxalin-6-yl)-methanol $R_f$ value: 0.45 (silica gel, petroleum ether/ethyl acetate=1:2)

Mass spectrum (ESI$^+$): m/z=203 [M+H]$^+$ (3) (8-methyl-quinoxalin-6-yl)-methanol $R_f$ value: 0.18 (silica gel, cyclohexane/ethyl acetate=1:1)

Mass spectrum (ESI$^+$): m/z=175 [M+H]$^+$ (4) (E)-3-pentafluorophenyl-2-propen-1-ol (Carried out with diisobutylaluminium hydride in toluene)

Mass spectrum (EI): m/z=224 [M]$^+$ (5) (E)-3-(2-trifluoromethyl-phenyl)-2-propen-1-ol (Carried out with diisobutylaluminium hydride in toluene)

(6) (E)-3-(3-trifluoromethyl-phenyl)-2-propen-1-ol (Carried out with diisobutylaluminium hydride in toluene)

Mass spectrum (EI): m/z=202 [M]$^+$ (7) (E)-3-(4-trifluoromethyl-phenyl)-2-propen-1-ol (Carried out with diisobutylaluminium hydride in toluene)

EXAMPLE XXVIII 4-hydroxymethyl-2-[(2-trimethylsilanyl-ethoxy)methyl]-2H-phthalazin-1-one Prepared by treating methyl 4-oxo-3-[(2-trimethylsilanyl-ethoxy)methyl]-3,4-dihydro-phthalazin-1-carboxylate with sodium borohydride in tetrahydrofuran at 40° C.

$R_f$ value: 0.55 (silica gel, cyclohexane/ethyl acetate 1:1)

Mass spectrum (ESI$^+$): m/z=307 [M+H]$^+$

The following compounds are obtained analogously to Example XXVIII:

(1) (3,4-dimethyl-isoquinolin-1-yl)-methanol (Carried out with lithium borohydride in tetrahydrofuran)

$R_f$ value: 0.35 (silica gel, petroleum ether/ethyl acetate=2:1)

Mass spectrum (ESI$^+$): m/z=188 [M+H]$^+$ (2) (3-methyl-imidazo[1,2-a]pyridin-2-yl)-methanol (Carried out with lithium borohydride in tetrahydrofuran)

$R_f$ value: 0.48 (silica gel, methylene chloride/methanol/conc. aqueous ammonia=90:10:1)

Mass spectrum (ESI$^+$): m/z=163 [M+H]$^+$ (3) (3,4-dimethyl-6,7-dihydro-5H-[2]pyrindin-1-yl)-methanol (Carried out with lithium borohydride in tetrahydrofuran)

$R_f$ value: 0.40 (aluminium oxide, petroleum ether/ethyl acetate=1:1)

Mass spectrum (ESI$^+$): m/z=178 [M+H]$^+$ (4) (3,4-dimethyl-5,6,7,8-tetrahydro-isoquinolin-1-yl)-methanol (Carried out with lithium borohydride in tetrahydrofuran)

$R_f$ value: 0.45 (aluminium oxide, petroleum ether/ethyl acetate=3:1)

Mass spectrum (ESI$^+$): m/z=192 [M+H]$^+$ (5) 6-hydroxymethyl-1,2,3,4-tetrahydro-phenanthridine (Carried out with lithium borohydride in tetrahydrofuran at ambient temperature)

$R_f$ value: 0.40 (silica gel, petroleum ether/ethyl acetate=2:1)

Mass spectrum (ESI$^+$): m/z=214 [M+H]$^+$

EXAMPLE XXIX

Methyl 4-oxo-3-[(2-tri methylsilanyl-ethoxy)methyl]-3,4-dihydro-phthalazin-1-carboxylate Prepared by reacting methyl 4-oxo-3,4-dihydro-phthalazin-1-carboxylate with (2-trimethylsilanyl-ethoxy)methylchloride in the presence of Hünig base in methylene chloride at ambient temperature.

$R_f$ value: 0.75 (silica gel, cyclohexane/ethyl acetate 6:4)

Mass spectrum (ESI$^+$): m/z=335 [M+H]$^+$

The following compounds are obtained analogously to Example XXIX:

(1) 7-acetyl-3-[(2-tri methylsilanyl-ethoxy)methyl]-3H-benzooxazol-2-one

Mass spectrum (ESI$^+$): m/z=308 [M+H]$^+$ (2) 4-acetyl-3-[(2-tri methylsilanyl-ethoxy)methyl]-3H-benzooxazol-2-one $R_f$ value: 0.87 (silica gel, methylene chloride/methanol=99:1)

(3) 4-acetyl-1,3-bis-[(2-trimethylsilanyl-ethoxy)methyl]-1,3-dihydro-benzoimidazol-2-one (Carried out with potassium-tert. butoxide in N,N-dimethylformamide)

$R_f$ value: 0.90 (silica gel, petroleum ether/ethyl acetate=1:1)

Mass spectrum (ESI$^+$): m/z=437 [M+H]$^+$ (4) 6-methyl-1-[(2-trimethylsilanyl-ethoxy)methyl]-1H-quinolin-2-one $R_f$ value: 0.78 (silica gel, petroleum ether/ethyl acetate=1:1)

Mass spectrum (ESI$^+$): m/z=290 [M+H]$^+$ (5) methyl {2-methyl-1-[(2-trimethylsilanyl-ethoxy)methyl]-1H-benzoimidazol-5-yl}-carboxylate (mixed with methyl {2-methyl-3-[(2-trimethylsilanyl-ethoxy)methyl]-3H-benzoimidazol-5-yl}-carboxylate)

Mass spectrum (ESI$^+$): m/z=321 [M+H]$^+$

EXAMPLE XXX

1-[2-(3-methanesulphonyl-phenyl)-2-oxo-ethyl]-3-methyl-7-(3-methyl-2-buten-1-yl)-8-[3-(tert.-butyloxycarbonylamino)-piperidin-1-yl]-xanthine 0.22 ml of a 35% hydrogen peroxide solution and 20 mg of sodium tungstate are added to 500 mg of 1-[2-(3-methylsulphanyl-phenyl)-2-oxo-ethyl]-3-methyl-7-(3-methyl-2-buten-1-yl)-8-[3-(tert.-butyloxycarbonylamino)-piperidin-1-yl]-xanthine in 5 ml methylene chloride. The reaction mixture is stirred overnight at ambient temperature, then 1 ml of methanol is added. After another 48 hours a further 1.5 ml of 35% hydrogen peroxide solution, a spatula tip of sodium tungstate and two drops of water are added. The next morning, the oxidation is complete according to thin layer chromatography and the reaction mixture is diluted with 50 ml methylene chloride and washed twice with 30 ml of 10% sodium thiosulphate solution. The organic phase is dried over magnesium sulphate and evaporated down, leaving a viscous resin which is reacted further without any more purification.

Yield: 530 mg (100% of theory)

$R_f$ value: 0.72 (silica gel, ethyl acetate)

Mass spectrum (ESI$^+$): m/z=629 [M+H]$^+$

EXAMPLE XXXI

1-[2-(3-carboxy-phenyl)-2-oxo-ethyl]-3-methyl-7-(3-methyl-2-buten-1-yl)-8-[3-(tert.-butyloxycarbonylamino)-piperidin-1-yl]-xanthine Prepared by treating 1-[2-(3-methoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine with 3 M sodium hydroxide solution in methanol at ambient temperature.

$R_f$ value: 0.34 (silica gel, methylene chloride/methanol=9:1)

Mass spectrum (ESI$^+$): m/z=595 [M+H]$^+$

The following compounds are obtained analogously to Example XXXI:

(1) 1-[2-(2-carboxy-phenyl)-2-oxo-ethyl]-3-methyl-7-(3-methyl-2-buten-1-yl)-8-[3-(tert.-butyloxycarbonylamino)-piperidin-1-yl]-xanthine $R_f$ value: 0.49 (silica gel, methylene chloride/methanol=9:1)

(2) 1-[2-(2-carboxymethoxy-phenyl)-2-oxo-ethyl]-3-methyl-7-(2-butyn-1-yl)-8-[3-(tert.-butyloxycarbonylamino)-piperidin-1-yl]-xanthine (Carried out with 4 M potassiuim hydroxide solution in tetrahydrofuran)

Mass spectrum (ESI$^+$): m/z=609 [M+H]$^+$ (3) 1-[2-(2-carboxymethylamino-phenyl)-2-oxo-ethyl]-3-methyl-7-((E)-2-buten-1-yl)-8-[(R)-3-(tert.-butyloxycarbonylamino)-piperidin-1-yl]-xanthine (Carried out with 4 M potassium hydroxide solution in tetrahydrofuran)

$R_f$ value: 0.65 (silica gel, cyclohexane/ethyl acetate=3:7)

Mass spectrum (ESI$^+$): m/z=610 [M+H]$^+$ (4) 1-carboxymethyl-3-methyl-7-(2-butyn-1-yl)-8-[3-(tert.-butyloxycarbonylamino)-piperidin-1-yl]-xanthine Mass spectrum (ESI$^+$): m/z=475 [M+H]$^+$

EXAMPLE XXXII

1-{2-[3-(methylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine A mixture of 190 mg of 1-[2-(3-carboxy-phenyl)-2-oxo-ethyl]-3-methyl-7-(3-methyl-2-buten-1-yl)-8-[3-(tert.-butyloxycarbonylamino)-piperidin-1-yl]-xanthine, 43 μl of a 40% aqueous methylamine solution, 103 mg of O-(benzotriazol-1-yl)-N,N,N',N'-tetramethyluronium tetrafluoroborate, 43 mg of N-hydroxybenzotriazole and 45 μl of triethylamine in 3 ml of tetrahydrofuran is stirred for eight hours at ambient temperature. For working up the reaction mixture is diluted with ethyl acetate and washed with water, 10% citric acid solution, 10% potassium carbonate solution and saturated sodium chloride solution. The organic phase is evaporated down and chromatographed through a silica gel column with methylene chloride/methanol (98:2 to 80:20) as eluant.

Yield: 173 mg (89% of theory)

$R_f$ value: 0.30 (silica gel, methylene chloride/methanol=20:1)

Mass spectrum (ESI$^+$): m/z=608 [M+H]$^+$

The following compounds are obtained analogously to Example XXXII:

(1) 1-{2-[3-(dimethylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.28 (silica gel, methylene chloride/methanol=20:1)

Mass spectrum (ESI$^+$): m/z=622 [M+H]$^+$ (2) 1-{2-[3-(morpholin-4-yl-carbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.30 (silica gel, methylene chloride/methanol=20:1)

Mass spectrum (ESI$^+$): m/z=664 [M+H]$^+$ (3) 1-{2-[2-(dimethylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.30 (silica gel, methylene chloride/methanol=20:1)

Mass spectrum (ESI$^+$): m/z=622 [M+H]$^+$ (4) 1-{2-[2-(morpholin-4-yl-carbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.30 (silica gel, methylene chloride/methanol=20:1)

Mass spectrum (ESI$^+$): m/z=664 [M+H]$^+$ (5) 1-(2-{2-[(isopropylaminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine (Carried out with Hünig base in N,N-dimethylformamide)

Mass spectrum (ESI$^+$): m/z=650 [M+H]$^+$ (6) 1-(2-{2-[(ethylaminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine (Carried out with Hünig base in N,N-dimethylformamide)

Mass spectrum (ESI$^+$): m/z=636 [M+H]$^+$ (7) 1-(2-{2-[2-oxo-2-(pyrrolidin-1-yl)-ethoxy]-phenyl}-2-oxo-ethyl)-3-methyl-7-(2-butyn-1-yl)-8-[3-(tert.-butyloxycarbonylamino)-piperidin-1-yl]-xanthine (Carried out with Hünig base in N,N-dimethylformamide)

Mass spectrum (ESI$^+$): m/z=662 [M+H]$^+$ (8) 1-(2-{2-[2-(morphol in-4-yl)-2-oxo-ethoxy]-phenyl}-2-oxo-ethyl)-3-methyl-7-(2-butyn-1-yl)-8-[3-(tert.-butyloxycarbonylamino)-piperidin-1-yl]-xanthine (Carried out with Hünig base in N,N-dimethylformamide)

Mass spectrum (ESI$^+$): m/z=678 [M+H]$^+$ (9) 1-(2-{2-[(methylaminocarbonyl)methylamino]-phenyl}-2-oxo-ethyl)-3-methyl-7-((E)-2-buten-1-yl)-8-[(R)-3-(tert.-butyloxycarbonylamino)-piperidin-1-yl]-xanthine $R_f$ value: 0.40 (silica gel, cyclohexane/ethyl acetate/methanol=5:4:1)

Mass spectrum (ESI$^+$): m/z=623 [M+H]$^+$

(10) 1-[(2-amino-phenylaminocarbonyl)methyl]-3-methyl-7-(2-butyn-1-yl)-8-[3-(tert.-butyloxycarbonylamino)-piperidin-1-yl]-xanthine $R_f$ value: 0.40 (silica gel, cyclohexane/ethyl acetate/methanol=5:4:1)

Mass spectrum (ESI$^+$): m/z=565 [M+H]$^+$

EXAMPLE XXXIII 1-chloromethyl-4-methyl-isoquinoline-hydrochloride

Prepared by treating (4-methyl-isoquinolin-1-yl)-methanol with thionyl chloride in methylene chloride.

$R_f$ value: 0.76 (silica gel, methylene chloride/methanol/conc. aqueous ammonia=95:5:0.1)

Mass spectrum (ESI$^+$): m/z=192, 194 [M+H]$^+$

The following compounds are obtained analogously to Example XXXIII:

(1) 1-chloromethyl-3,4-dimethyl-isoquinoline-hydrochloride $R_f$ value: 0.65 (silica gel, petroleum ether/ethyl acetate=2:1)

Mass spectrum (ESI$^+$): m/z=206, 208 [M+H]$^+$ (2) 5-chloromethyl-8-methoxy-quinoline-hydrochloride Mass spectrum (ESI$^+$): m/z=208, 210 [M+H]$^+$ (3) 8-chloromethyl-5-methoxy-quinoline-hydrochloride Mass spectrum (EI): m/z=207, 209 [M]$^+$ (4) 2-chloromethyl-3-methyl-imidazo[1,2-a]pyridine-hydrochloride $R_f$ value: 0.55 (silica gel, methylene chloride/methanol/conc. aqueous ammonia=90:10:1)

Mass spectrum (ESI$^+$): m/z=181, 183 [M+H]$^+$ (5) 8-chloromethyl-5-methoxy-isoquinoline-hydrochloride Mass spectrum (ESI$^+$): m/z=208, 210 [M+H]$^+$ (6) 1-chloromethyl-3,4-dimethyl-6,7-dihydro-5H-[2]pyridine-hydrochloride $R_f$ value: 0.50 (aluminium oxide, petroleum ether/ethyl acetate=10:1)

Mass spectrum (ESI$^+$): m/z=196, 198 [M+H]$^+$ (7) 1-chloromethyl-3,4-dimethyl-5,6,7,8-tetrahydro-isoquinoline-hydrochloride $R_f$ value: 0.50 (aluminium oxide, petroleum ether/ethyl acetate=10:1)

Mass spectrum (ESI$^+$): m/z=210, 212 [M+H]$^+$ (8) 6-chloromethyl-2,3,8-trimethyl-quinoxaline-hydrochloride Mass spectrum (ESI$^+$): m/z=221, 223 [M+H]$^+$ (9) 6-chloromethyl-8-methyl-quinoxaline-hydrochloride Mass spectrum (ESI$^+$): m/z=193,195 [M+H]$^+$

(10) 6-chloromethyl-1,2,3,4-tetrahydro-phenanthridine-hydrochloride $R_f$ value: 0.50 (silica gel, petroleum ether/ethyl acetate=5:1)

Mass spectrum (ESI$^+$): m/z=232, 234 [M+H]$^+$

EXAMPLE XXXIV

1-[(4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine 0.5 ml of a 1 M sodium methoxide solution in methanol is added dropwise to a solution of 428 mg of 1-cyanomethyl-3-methyl-7-(2-butyn-1-yl)-8-[3-(tert.-butyloxycarbonylamino)-piperidin-1-yl]-xanthine in 3 ml of methanol at ambient temperature. After about 20 minutes the thick suspension formed is heated gently in a water bath and diluted with 2 ml of methanol. As soon as the reaction to form the iminoester is complete according to thin layer chromatography, the reaction mixture is neutralised with 0.5 ml 1 M glacial acetic acid solution in methanol and combined with a solution of 130 mg of anthranilic acid in 2 ml of methanol. Gentle heating produces a clear solution, which is stirred for 2.5 hours at ambient temperature. Then the reaction mixture is gently refluxed for about 3.5 hours. After standing overnight at ambient temperature the methanol is distilled off and the residue is stirred with cold water, suction filtered and dried. The crude product is suspended in 5 ml of methanol, gently heated and after cooling suction filtered, washed with methanol and dried in the desiccator.

Yield: 302 mg (56% of theory)

$R_f$ value: 0.55 (silica gel, ethyl acetate)

Mass spectrum (ESI$^+$): m/z=575 [M+H]$^+$

The following compounds are obtained analogously to Example XXXV:

(1) (4-difluoromethoxy-naphthalen-1-yl)-methanol $R_f$ value: 0.33 (silica gel, cyclohexane/ethyl acetate=6:4)

Mass spectrum (ESI$^-$): m/z=223 [M-H]

EXAMPLE XXXV (4-dimethylamino-naphthalen-1-yl)-methanol prepared by reduction of 4-dimethylamino-naphthalene-1-carbaldehyde with sodium borohydride in aqueous tetrahydrofuran.

$R_f$ value: 0.67 (silica gel, cyclohexane/ethyl acetate=1:1)

EXAMPLE XXXVI 2-bromo-1-(2,3-dihydro-benzo[1,4]dioxin-5-yl)-ethanone prepared by bromination of 1-(2,3-dihydro-benzo[1,4]dioxin-5-yl)-ethanone in methylene chloride while cooling gently with an ice bath. The dibromo compound formed as a by-product is separated off by column chromatography.

Mass spectrum (ESI$^+$): m/z=257, 259 [M+H]$^+$ $R_f$ value: 0.92 (silica gel, methylene chloride)

The following compounds are obtained analogously to Example XXXVI:

(1) 7-(2-bromo-acetyl)-3-methyl-3H-benzooxazol-2-one (bromination is carried out in dioxane at 40° C.; the product is contaminated with approx. 20% dibromo compound)

$R_f$ value: 0.44 (silica gel, petroleum ether/ethyl acetate=1:1)

Mass spectrum (ESI$^+$): m/z=270, 272 [M+H]$^+$ (2) 1-benzo[1,3]dioxol-4-yl-2-bromo-ethanone Mass spectrum (ESI$^+$): m/z=243, 245 [M+H]$^+$ $R_f$ value: 0.94 (silica gel, methylene chloride)

(3) 2-[2-(2-bromo-acetyl)-phenoxy]-N-ethyl-acetamide (bromination is carried out with copper(II)bromide in dioxane)

Mass spectrum (ESI$^+$): m/z=300, 302 [M+H]$^+$ (4) 4-(2-bromo-acetyl)-3-methyl-3H-benzooxazol-2-one $R_f$ value: 0.67 (silica gel, methylene chloride/methanol=99:1)

Mass spectrum (ESI$^+$): m/z=270, 272 [M+H]$^+$ (5) 2-[2-(2-bromo-acetyl)-phenoxy]-N-methyl-acetamide Mass spectrum (ESI$^+$): m/z=386, 388 [M+H]$^+$ (6) 7-(2-bromo-acetyl)-3-[(2-trimethylsilanyl-ethoxy)methyl]-3H-benzooxazol-2-one $R_f$ value: 0.84 (silica gel, methylene chloride/methanol=99:1)

Mass spectrum (ESI$^+$): m/z=384, 386 [M+H]$^+$ (7) 4-(2-bromo-acetyl)-1,3-dimethyl-1,3-dihydro-benzoimidazol-2-one $R_f$ value: 0.38 (silica gel, ethyl acetate/petroleum ether=1:1)

Mass spectrum (ESI$^+$): m/z=283, 285 [M+H]$^+$ (8) 4-(2-bromo-acetyl)-3-[(2-trimethylsilanyl-ethoxy)methyl]-3H-benzooxazol-2-one $R_f$ value: 0.82 (silica gel, methylene chloride/methanol=99:1)

(9) 4-(2-bromo-acetyl)-1-ethoxycarbonyl-3-methyl-1,3-dihydro-benzoimidazol-2-one $R_f$ value: 0.39 (silica gel, petroleum ether/ethyl acetate=2:1)

Mass spectrum (ESI$^+$): m/z=341, 343 [M+H]$^+$

(10) 2-bromo-1-(2,2-difluoro-benzo[1,3]dioxol-4-yl)-ethanone

Mass spectrum (ESI$^-$): m/z=277, 279 [M-H]

EXAMPLE XXXVII (2,3-dihydro-benzo[1,4]dioxin-5-yl)-ethanone

Prepared by reacting 1-(2,3-dihydroxy-phenyl)-ethanone with 1,2-dibromoethane in the presence of potassium carbonate in N,N-dimethylformamide at 100° C.

$R_f$ value: 0.43 (silica gel, ethyl acetate/petroleum ether=1:4)

Mass spectrum (ESI$^+$): m/z=179 [M+H]$^+$

EXAMPLE XXXVIII

1-[(3-methyl-4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine Prepared by reacting 1-[(4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine with methyl iodide in the presence of potassium carbonate in N,N-dimethylformamide at ambient temperature.

$R_f$ value: 0.50 (silica gel, ethyl acetate)

Mass spectrum (ESI$^+$): m/z=589 [M+H]$^+$

The following compounds are obtained analogously to Example XXXVIII:

(1) 7-acetyl-3-methyl-3H-benzooxazol-2-one (The methylation is carried out in the presence of sodium carbonate in methanol)

$R_f$ value: 0.46 (silica gel, petroleum ether/ethyl acetate=1:1)

Mass spectrum (ESI$^+$): m/z=192 [M+H]$^+$ (2) 4-acetyl-3-methyl-3H-benzooxazol-2-one (The methylation is carried out in the presence of sodium carbonate in methanol while refluxing)

$R_f$ value: 0.67 (silica gel, methylene chloride/methanol=99:1)

Mass spectrum (ESI$^+$): m/z=192 [M+H]$^+$ (3) 4-acetyl-1,3-dimethyl-1,3-dihydro-benzoimidazol-2-one (Carried out in the presence of potassium-tert. butoxide)

$R_f$ value: 0.40 (silica gel, ethyl acetate/petroleum ether=2:1)

Mass spectrum (ESI$^+$): m/z=205 [M+H]$^+$ (4) 4-acetyl-1-ethoxycarbonyl-3-methyl-1,3-dihydro-benzoimidazol-2-one $R_f$ value: 0.23 (silica gel, petroleum ether/ethyl acetate=2:1)

Mass spectrum (ESI$^+$): m/z=263 [M+H]$^+$ (5) 1-[(1-methyl-1H-benzoimidazol-2-yl)methyl]-3-methyl-7-(2-butyn-1-yl)-8-[3-(tert.-butyloxycarbonylamino)-piperidin-1-yl]-xanthine Mass spectrum (ESI$^+$): m/z=561 [M+H]$^+$ (6) 1-{[1-(2-cyano-ethyl)-1H-benzoimidazol-2-yl]methyl}-3-methyl-7-(2-butyn-1-yl)-8-[3-(tert.-butyloxycarbonylamino)-piperidin-1-yl]-xanthine $R_f$-value: 0.50 (silica gel, cyclohexane/ethyl acetate/methanol=5:4:1)

Mass spectrum (ESI$^+$): m/z=600 [M+H]$^+$ (7) 1-({1-[(methylaminocarbonyl)methyl]-1H-benzoimidazol-2-yl}methyl)-3-methyl-7-(2-butyn-1-yl)-8-[3-(tert.-butyloxycarbonylamino)-piperidin-1-yl]-xanthine $R_f$-value: 0.45 (silica gel, cyclohexane/ethyl acetate/methanol=5:4:1)

Mass spectrum (ESI$^+$): m/z=618 [M+H]$^+$ (8) 1-[(1-benzyl-1H-benzoimidazol-2-yl)methyl]-3-methyl-7-(2-butyn-1-yl)-8-[3-(tert.-butyloxycarbonylamino)-piperidin-1-yl]-xanthine $R_f$-value: 0.50 (silica gel, cyclohexane/ethyl acetate/methanol=5:4:1)

Mass spectrum (ESI$^+$): m/z=637 [M+H]$^+$

EXAMPLE XXXIX

1-[2-(2-cyanomethylamino-phenyl)-2-oxo-ethyl]-3-methyl-7-(3-methyl-2-buten-1-yl)-8-[3-(tert.-butyloxycarbonylamino)-piperidin-1-yl]-xanthine Prepared by reacting 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine with paraformaldehyde and potassium cyanide in the presence of zinc chloride in glacial acetic acid at 40° C.

$R_f$-value: 0.45 (silica gel, cyclohexane/ethyl acetate=3:7)

Mass spectrum (ESI$^+$): m/z=605 [M+H]$^+$

EXAMPLE XL

1-[2-(2-amino-phenyl)-2-oxo-ethyl]-3-methyl-7-(2-butyn-1-yl)-8-[(S)-3-(tert.-butyloxycarbonylamino)-piperidin-1-yl]-xanthine prepared by reduction of 1-[2-(2-nitro-phenyl)-2-oxo-ethyl]-3-methyl-7-(2-butyn-1-yl)-8-[(S)-3-(tert.-butyloxycarbonylamino)-piperidin-1-yl]-xanthine with sodium dithionite in a mixture of methylglycol and water (2:1) at 100° C.

$R_f$ value: 0.34 (silica gel, methylene chloride/methanol=95:5)

The following compounds are obtained analogously to Example XL:

(1) 1-[2-(2-amino-phenyl)-2-oxo-ethyl]-3-methyl-7-(2-butyn-1-yl)-8-[(R)-3-(tert.-butyloxycarbonylamino)-piperidin-1-yl]-xanthine $R_f$-value: 0.50 (silica gel, cyclohexane/ethyl acetate=4:6)

EXAMPLE XLI 2-chloromethyl-4-methyl-quinazoline prepared by treatment of 2.95 g of 2-chloromethyl-4-methyl-quinazoline-3-oxide with 6 ml phosphorus trichloride in 150 ml chloroform while refluxing.

Yield: 1.75 g (57% of theory)

$R_f$ value: 0.81 (silica gel, methylene chloride/methanol=95:5)

Mass spectrum (ESI$^+$): m/z=193,195 [M+H]$^+$

EXAMPLE XLII 2-chloromethyl-4-dimethylamino-quinazoline

A freshly prepared solution of 202 mg of dimethylamine in 3.2 ml of tetrahydrofuran is added dropwise to 500 mg of 4-chloro-2-chloromethyl-quinazoline in 5 ml of tetrahydrofuran while cooling with an ice bath. Then the reaction mixture is stirred for another 3.5 hours while cooling with an ice bath and then for a further 30 minutes at ambient temperature.

The solvent is then gently distilled off using a rotary evaporator and the residue is taken up in methylene chloride. The solution is washed with saturated sodium hydrogen carbonate solution and with water, dried over magnesium sulphate and evaporated down. The solid residue is stirred with a little tert.-butylmethylether, suction filtered, washed with petroleum ether and dried in vacuo.

Yield: 323 mg (62% of theory)

$R_f$-value: 0.60 (silica gel, cyclohexane/ethyl acetate=1:1)

Mass spectrum (ESI$^+$): m/z=222, 224 [M+H]$^+$

The following compounds are obtained analogously to Example XLII:

(1) 2-chloromethyl-4-(morpholine-4-yl)-quinazoline $R_f$-value: 0.50 (silica gel, cyclohexane/ethyl acetate=1:1)

Mass spectrum (ESI$^+$): m/z=264, 266 [M+H]$^+$ (2) 2-chloromethyl-4-(piperidin-1-yl)-quinazoline $R_f$-value: 0.70 (silica gel, cyclohexane/ethyl acetate=1:1)

Mass spectrum (ESI$^+$): m/z=262, 264 [M+H]$^+$ (3) 4-[4-(tert.-butyloxycarbonyl)-piperazin-1-yl]-2-chloromethyl-quinazoline $R_f$-value: 0.57 (silica gel, cyclohexane/ethyl acetate=1:1)

Mass spectrum (ESI$^+$): m/z=363, 365 [M+H]$^+$ (4) 2-chloromethyl-4-(pyrrolidin-1-yl)-quinazoline $R_f$-value: 0.50 (silica gel, cyclohexane/ethyl acetate=1:1)

Mass spectrum (ESI$^+$): m/z=248, 250 [M+H]$^+$ (5) 2-chloromethyl-4-ethoxy-quinazoline (The reaction is carried out with sodium ethoxide in ethanol at ambient temperature.)

$R_f$-value: 0.50 (silica gel, cyclohexane/ethyl acetate=3:1)

Mass spectrum (ESI$^+$): m/z=223, 225 [M+H]$^+$ (6) 2-chloromethyl-4-isopropyloxy-quinazoline (The reaction is carried out with sodium isopropoxide in isopropanol at ambient temperature.)

$R_f$-value: 0.70 (silica gel, cyclohexane/ethyl acetate=3:1)

Mass spectrum (ESI$^+$): m/z=237, 239 [M+H]$^+$ (7) 2-chloromethyl-4-phenyloxy-quinazoline (The reaction is carried out with sodium hydride and phenol in tetrahydrofuran at ambient temperature.)

$R_f$-value: 0.65 (silica gel, cyclohexane/ethyl acetate=3:1)

Mass spectrum (ESI$^+$): m/z=271, 273 [M+H]$^+$

EXAMPLE XLIII 1-(2-{2-[(ethoxycarbonyl)methylamino]-phenyl}-2-oxo-ethyl)-3-methyl-7-((E)-2-buten-1-yl)-8-[3-(tert.-butyloxycarbonylamino)-piperidin-1-yl]-xanthine A solution of 110 μL of ethyl diazoacetate in 0.5 ml of toluene is added dropwise to 531 mg of 1-[2-(2-amino-phenyl)-2-oxo-ethyl]-3-methyl-7-((E)-2-buten-1-yl)-8-[3-(tert.-butyloxycarbonylamino)-piperidin-1-yl]-xanthine and 10 mg of methyltrioxorhenium in 4.5 ml of toluene at ambient temperature under an argon atmosphere. The reaction mixture is stirred for 15 hours at ambient temperature. Then approx. another 5 mg of methyltrioxorhenium and 20 μL ethyl diazoacetate are added and the reaction mixture is heated to 50° C. for two hours. After cooling to ambient temperature another 5 mg of methyltrioxorhenium and 20 μL ethyl diazoacetate are added. After another 16 hours at ambient temperature the reaction mixture is combined with 5 ml of conc. aqueous ammonia, shaken thoroughly and added to an Extrelut pack.

After 15 min it is rinsed with 200 ml methylene chloride. The methylene chloride solution is evaporated down and chromatographed through a silica gel column with cyclohexane/ethyl acetate/isopropanol (8:2:0 to 8:1:1) as eluant.

Yield: 220 mg (36% of theory)
$R_f$ value: 0.40 (silica gel, cyclohexane/ethyl acetate=1:1)
Mass spectrum (ESI$^+$): m/z=638 [M+H]$^+$

EXAMPLE XLIV

1-[(2-cyano-benzofuran-3-yl)methyl]-3-methyl-7-(2-butyn-1-yl)-8-[3-(tert.-butyloxycarbonylamino)-piperidin-1-yl]-xanthine A mixture of 215 mg of 1-{2-[2-cyanomethoxy-phenyl]-2-oxo-ethyl}-3-methyl-7-(2-butyn-1-yl)-8-[3-(tert.-butyloxycarbonylamino)-piperidin-1-yl]-xanthine and 244 mg of caesium carbonate in 4 ml of N,N-dimethylformamide is stirred for two hours at 50° C., then a further three hours at 70° C. For working up the reaction mixture is combined with water and the precipitate formed is suction filtered and dried.

Yield: 130 mg (62% of theory)
Mass spectrum (ESI$^+$): m/z=572 [M+H]$^+$

EXAMPLE XLV

1-[2-(3-methyl-2-oxo-2,3-dihydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine Prepared by treating 1-[2-(1-ethoxycarbonyl-3-methyl-2-oxo-2,3-dihydro-1H-benzoimidazol-4-yl)-2-oxo-ethyl]-3-methyl-7-(2-butyn-1-yl)-8-[3-(tert.-butyloxy-carbonylamino)-piperidin-1-yl]-xanthine with 1 N sodium hydroxide solution in methanol at ambient temperature.

$R_f$ value: 0.36 (silica gel, ethyl acetate)
Mass spectrum (ESI$^+$): m/z=605 [M+H]$^+$

EXAMPLE XLVI 4-acetyl-1-ethoxycarbonyl-1,3-di hydro-benzoimidazol-2-one 5.29 g of diethyldicarbonate and 611 mg of dimethylaminopyridine are added to 1.50 g of 1-(2,3-diamino-phenyl)-ethanone in 75 ml methylene chloride. The reaction mixture is stirred for three hours at ambient temperature, then another 100 mg of dimethylaminopyridine and 1 ml of diethyldicarbonate are added and the mixture is stirred for a further 20 hours at ambient temperature. For working up the reaction mixture is diluted with methylene chloride, washed with 2 N citric acid solution as well as saturated sodium hydrogen carbonate solution and saturated sodium chloride solution, dried over magnesium sulphate and evaporated down. The residue is chromatographed through a silica gel column with petroleum ether/ethyl acetate (3:1 to 1:2) as eluant. The desired product is stirred with a little tert.-butylmethylether, suction filtered, nachwashed with a little ethyl acetate and tert.-butylmethylether and dried.

Yield: 900 mg (36% of theory)
$R_f$ value: 0.15 (silica gel, petroleum ether/ethyl acetate=2:1)
Mass spectrum (ESI$^+$): m/z=249 [M+H]$^+$

EXAMPLE XLVII

1-[(4-amino-quinazolin-2-yl)methyl]-3-methyl-7-(2-butyn-1-yl)-8-[3-(tert.-butyloxycarbonylamino)-piperidin-1-yl]-xanthine 501 mg of 1-cyanomethyl-3-methyl-7-(2-butyn-1-yl)-8-[3-(tert.-butyloxycarbonylamino)-piperidin-1-yl]-xanthine are added to a mixture of 17 mg of potassium-tert. butoxide in 10 ml of methanol. After brief heating with stirring a clear solution is formed and after about 20 minutes the nitrile has largely reacted to form the iminoester according to thin layer chromatography. 206 mg of 2-amino-benzamidine-hydrochloride are then added and the reaction mixture is refluxed for four hours. After cooling to ambient temperature the precipitate formed is suction filtered, washed with methanol and dried.

Yield: 143 mg (23% of theory)
$R_f$ value: 0.15 (silica gel, ethyl acetate)
Mass spectrum (ESI$^+$): m/z=574 [M+H]$^+$

EXAMPLE XLVIII 1-(2-phenyl-2-oxo-ethyl)-3-methyl-7-((Z)-2-buten-1-yl)-8-[3-(tert.-butyloxycarbonylamino)-piperidin-1-yl-xanthine 150 mg of 1-(2-phenyl-2-oxo-ethyl)-3-methyl-7-(2-butyn-1-yl)-8-[3-(tert.-butyloxycarbonylamino)-piperidin-1-yl]-xanthine are hydrogenated in a mixture of 5 ml of tetrahydrofuran and 5 ml of methanol in the presence of 30 mg of 5% m palladium on activated charcoal (contaminated with quinoline) at ambient temperature, until the calculated amount of hydrogen has been taken up. Then a spatula tip of activated charcoal is added and the mixture is suction filtered. The filtrate is evaporated down and the crude product is purified by chromatography over a silica gel column with cyclohexane/ethyl acetate (7:3 to 4:6).

Yield: 120 mg (85% of theory)
$R_f$ value: 0.40 (silica gel, cyclohexane/ethyl acetate=4:6)
Mass spectrum (ESI$^+$): m/z=537 [M+H]$^+$

EXAMPLE XLIX 8-hydroxymethyl-5-methoxy-quinoline 148 mg of sodium hydride (approx. 60% in mineral oil) are added batchwise to a solution of 640 mg of 8-hydroxymethyl-quinolin-5-ol in N,N-dimethylformamide while cooling with an ice bath and the reaction mixture is slowly heated to ambient temperature. After the development of gas has ended, 230 μl methyl iodide are added dropwise while cooling with an ice bath, then the reaction mixture is stirred for approx. another two hours at ambient temperature. For working up it is poured onto ice water, saturated with sodium chloride and extracted with a mixture of diethyl ether and ethyl acetate. The combined extracts are washed with saturated sodium chloride solution, dried over magnesium sulphate and evaporated down. The flask residue is triturated with petroleum ether and the supernatant is decanted. The crude product is purified through a silica gel column with ethyl acetate as eluant.

Yield: 470 mg (68% of theory)

$R_f$ value: 0.70 (silica gel, ethyl acetate)

Mass spectrum (ESI$^+$): m/z=190 [M+H]$^+$

The following compounds are obtained analogously to Example XLIX:

(1) 8-hydroxymethyl-5-methoxy-isoquinoline $R_f$ value: 0.40 (silica gel, methylene chloride/methanol=10:1)

Mass spectrum (ESI$^+$): m/z=190 [M+H]$^+$

EXAMPLE L 8-hydroxymethyl-quinolin-5-ol 3.40 g of quinolin-5-ol is combined with 8 ml of conc. hydrochloric acid and 8 ml of 37% formalin solution while cooling with an ice bath. Then hydrogen chloride gas is piped through the reaction mixture for about two hours, while the temperature slowly rises. The reaction mixture is stirred first overnight while cooling with an ice bath, then at ambient temperature and then evaporated down in vacuo. The flask residue is taken up in water, covered with a layer of diethyl ether and adjusted to pH 10 while cooling with an ice bath and vigorously stirring with dilute ammonia solution. After another two hours' vigorous stirring at ambient temperature the organic phase is separated off and the aqueous phase is extracted with diethyl ether. The combined organic phases are washed with water and saturated sodium chloride solution, dried over magnesium sulphate and evaporated down. The flask residue is chromatographed through a silica gel column with methylene chloride/methanol (20:1) as eluant.

Yield: 660 mg (16% of theory)

Mass spectrum (ESI$^+$): m/z=176 [M+H]$^+$

The following compounds are obtained analogously to Example L:

(1) 8-hydroxymethyl-isoquinolin-5-ol $R_f$ value: 0.50 (silica gel, methylene chloride/methanol=5:1)

Mass spectrum (ESI$^+$): m/z=176 [M+H]$^+$

EXAMPLE LI

1-[(2-cyclopropyl-quinazolin-4-yl)methyl]-3-methyl-7-[(1-cyclopenten-1-yl)methyl]-8-[3-(tert.-butyloxy-carbonylamino)-piperidin-1-yl]-xanthine A mixture of 250 mg of 1-(2-{2-[(cyclopropylcarbonyl) amino]-phenyl}-2-oxo-ethyl)-3-methyl-7-[(1-cyclopenten-1-yl)methyl]-8-[3-(tert.-butyloxycarbonylamino)-piperidin-1-yl]-xanthine and 7.5 ml of ethanolic ammonia solution (6 M) is heated to 150° C. for seven hours in a bomb. For working up the reaction mixture is evaporated down and chromatographed through a silica gel column with methylene chloride/methanol (100:0 to 70:30) as eluant. The contaminated product fraction is evaporated down and again purified through a reversed phase HPLC column with water/acetonitrile/trifluoroacetic acid (65:15:0.08 to 0:100:0.1) as eluant. The product fractions are evaporated down, made alkaline with dilute sodium hydroxide solution and extracted with methylene chloride. The combined extracts are dried over magnesium sulphate and evaporated down.

Yield: 40 mg (14% of theory)

$R_f$ value: 0.40 (silica gel, methylene chloride/ethyl acetate=1:1)

Mass spectrum (ESI$^+$): m/z=627 [M+H]$^+$

EXAMPLE LII 4-(2-bromo-acetyl)-1,3-bis-[(2-trimethylsilanyl-ethoxy)methyl]-1,3-di hydro-benzoimidazol-2-one 520 mg of 2-pyrrolidinone-hydrotribromide and 89 mg of 2-pyrrolidinone are added to 420 mg of 4-acetyl-1,3-bis-[(2-trimethylsilanyl-ethoxy)methyl]-1,3-dihydro-benzoimidazol-2-one in 5 ml of tetrahydrofuran under an argon atmosphere. The reaction mixture is refluxed for two hours and then suction filtered while still warm. The filter cake is washed with tetrahydrofuran and the filtrate is evaporated down, leaving 660 mg of a yelllowish-brown solid. This is stirred with a little methanol, suction filtered, washed with some methanol and dried. The crude product is reacted further without any more purification.

Yield: 430 mg (87% of theory)

$R_f$ value: 0.23 (silica gel, petroleum ether/ethyl acetate=9:1)

Mass spectrum (EI): m/z=514, 516 [M]+

The following compounds are obtained analogously to Example LII:

(1) 7-(2-bromo-acetyl)-1-(tert.-butyloxycarbonyl)-1H-indole $R_f$ value: 0.33 (silica gel, petroleum ether/ethyl acetate=9:1)

Mass spectrum (ESI$^+$): m/z=338, 340 [M+H]$^+$ (2) 2-bromo-1-(3-isopropyloxy-phenyl)-ethanone (Carried out with phenyltrimethylammonium tribromide in methylene chloride)

$R_f$ value: 0.39 (silica gel, cyclohexane/ethyl acetate=9:1)

(3) 2-bromo-1-(3-difluoromethoxy-phenyl)-ethanone (Carried out with phenyltrimethylammonium tribromide in methylene chloride)

$R_f$ value: 0.24 (ready-made reversed phase TLC plate (E. Merck), acetonitrile/water/trifluoroacetic acid=50:50:1)

EXAMPLE LIII methyl 3-methyl-imidazo[1,2-a]pyridine-2-carboxylate

A mixture of 1.91 g of 2-aminopyridine and 4.40 g of methyl 3-bromo-2-oxo-butyrate in 40 ml of ethanol is refluxed for 6 hours and then left to stand for 2 days at ambient temperature. The solvent is distilled off using the rotary evaporator and the crude product is purified by chromatography over a silica gel column with methylene chloride/methanol/methanolic ammonia solution (95:4:1 to 90:9:1) as eluant. 560 mg of the ethyl ester are isolated as the by-product.

Yield: 2.09 g (54% of theory)

$R_f$ value: 0.20 (silica gel, methylene chloride/ethyl acetate=1:1)

Mass spectrum (ESI$^+$): m/z=191 [M+H]$^+$

EXAMPLE LIV 2-chloromethyl-4-isopropyl-quinazoline

Dry hydrogen chloride gas is piped through a solution of 2.86 g of 1-(2-amino-phenyl)-2-methyl-propan-1-one and 1.33 ml of chloroacetonitrile in 14 ml dioxane with stirring at ambient temperature for approx. five hours. Then the dioxane is largely distilled off in a water jet vacuum. The honey-like residue is combined with ice water and the resulting suspension is made alkaline with saturated potassium carbonate solution while cooling with an ice bath. The precipitate is suction filtered, washed with water and dried. The crude product is purified by chromatography over a silica gel column with petroleum ether/methylene chloride (8:2 to 0:1) as eluant.

Yield: 1.80 g (58% of theory)

$R_f$ value: 0.30 (silica gel, methylene chloride/petroleum ether=1:1)

Mass spectrum (ESI$^+$): m/z=221, 223 [M+H]$^+$

EXAMPLE LV 1-chloromethyl-3-trifluoromethyl-3,4-dihydro-isoquinoline 530 mg of N-(1-benzyl-2,2,2-trifluoro-ethyl)-2-chloro-acetamide (prepared by reacting 1-benzyl-2,2,2-trifluoro-ethylamine with chloroacetyl chloride in the presence of triethylamine) and 0.74 ml of phosphorus oxychloride are added to 4.00 g of polyphosphoric acid. The viscous mixture is stirred for 1.5 hours at 130° C. For working up the reaction mixture is cooled and combined with ice water, stirred vigorously for ten minutes and suction filtered. The filter cake is dissolved in ethyl acetate and the solution is dried over magnesium sulphate and evaporated down, leaving a white solid.

Yield: 415 mg (84% of theory)

$R_f$ value: 0.55 (aluminium oxide, petroleum ether/ethyl acetate=10:1)

Mass spectrum (ESI$^+$): m/z=248, 250 [M+H]$^+$

The following compound is obtained analogously to Example LV:

(1) 1-methyl-3-trifluoromethyl-3,4-dihydro-isoquinoline (The starting material N-(1-benzyl-2,2,2-trifluoro-ethyl)-acetamide is obtained by reacting 1-benzyl-2,2,2-trifluoro-ethylamine with acetic anhydride.)

EXAMPLE LVI 3-bromomethyl-1-(1-cyano-1-methyl-ethyl)-isoquinoline

A mixture of 375 mg of 1-(1-cyano-1-methyl-ethyl)-3-methyl-isoquinoline and 321 mg of N-bromosuccinimide in 5 ml carbon tetrachloride is combined with a spatula tip of 2,2-azoisobutyric acid dinitrile and refluxed for about six hours. The cooled reaction mixture is filtered and evaporated down. The flask residue is reacted further without any more purification.

$R_f$ value: 0.70 (silica gel, cyclohexane/ethyl acetate=3:1)

The following compounds are obtained analogously to Example LVI:

(1) 6-bromomethyl-1-[(2-trimethylsilanyl-ethoxy)methyl]-1H-quinolin-2-one (2) 1-bromomethyl-4-bromo-3-methoxy-isoquinoline (3) 2-bromomethyl-[1,5]naphthyridine Mass spectrum (ESI$^+$): m/z=223, 225 [M+H]$^+$ (4) 5-bromomethyl-[1,6]naphthyridine $R_f$ value: 0.48 (silica gel, ethyl acetate/methanol=98:2)

(5) 7-bromomethyl-5-phenyl-quinoxaline $R_f$ value: 0.85 (silica gel, methylene chloride/methanol=95:5)

Mass spectrum (ESI$^+$): m/z=299, 301 [M+H]$^+$ (6) 4-bromomethyl-[1,5]naphthyridine $R_f$ value: 0.56 (silica gel, methylene chloride/ethyl acetate=7:3)

Mass spectrum (ESI$^+$): m/z=223, 225 [M+H]$^+$ (7) 1-bromomethyl-3-trifluoromethyl-isoquinoline Mass spectrum (ESI$^+$): m/z=290, 292 [M+H]$^+$ (8) 1-bromomethyl-3-difluoromethyl-isoquinoline Mass spectrum (ESI$^+$): m/z=272, 274 [M+H]$^+$ (9) 1-bromomethyl-4-chloro-3-methoxy-isoquinoline

EXAMPLE LVII 1-(1-cyano-1-methyl-ethyl)-3-methyl-isoquinoline 3.30 g of 2,2-azoisobutyric acid dinitrile are added to 1.60 g of 3-methyl-isoquinoline-N-oxide in 30 ml of toluene. The reaction mixture is stirred for six hours at 85° C. and then left to stand for two days at ambient temperature. For working up the reaction mixture is extracted with 20% hydrochloric acid. The combined aqueous phases are diluted with methylene chloride, made alkaline with saturated potassium carbonate solution while cooling with an ice bath and extracted with methylene chloride. The combined methylene chloride extracts are dried over magnesium sulphate and evaporated down. The residue is chromatographed through a silica gel column with cyclohexane as eluant.

Yield: 375 mg (18% of theory)

Mass spectrum (ESI$^+$): m/z=211 [M+H]$^+$ $R_f$ value: 0.75 (silica gel, cyclohexane/ethyl acetate=3:1)

EXAMPLE LVIII 1-(2-cyanoimino-2-phenyl-ethyl)-3-methyl-7-(2-butyn-1-yl)-8-[3-(tert.-butyloxycarbonylamino)-piperidin-1-yl]-xanthine (E/Z-mixture)

0.48 ml of a 1 M solution of titanium tetrachloride in methylene chloride are added dropwise to 244 mg of 1-(2-phenyl-2-oxo-ethyl)-3-methyl-7-(2-butyn-1-yl)-8-[3-(tert.-butyloxycarbonylamino)-piperidin-1-yl]-xanthine in 7 ml of methylene chloride. Then 88 μl of 1,3-bis(trimethylsilyl)carbodiimide are added and the mixture is stirred for four hours at ambient temperature. For working up the reaction mixture is diluted with methylene chloride and poured onto ice water. The organic phase is washed with 0.5 N citric acid, dried over magnesium sulphate and evaporated down. The crude product is purified by chromatography over a silica gel column with methylene chloride/methanol (98:2 to 95:5) as eluant.

Yield: 206 mg (97% of theory)

Mass spectrum (ESI$^-$): m/z=557 [M-H]

$R_f$ value: 0.16 (silica gel, cyclohexane/ethyl acetate=1:1)

EXAMPLE LIX

1-[(1H-benzoimidazol-2-yl)methyl]-3-methyl-7-(2-butyn-1-yl)-8-[3-(tert.-butyloxycarbonylamino)-piperidin-1-yl]-xanthine 350 mg of 1-[(2-amino-phenylaminocarbonyl)methyl]-3-methyl-7-(2-butyn-1-yl)-8-[3-(tert.-butyloxycarbonylamino)-piperidin-1-yl]-xanthine are refluxed in 3 ml glacial acetic acid for two hours. Then the reaction mixture is evaporated down, the flask residue is combined with 5 ml of 1 M sodium hydroxide solution and washed with methylene chloride. Then the aqueous phase is acidified with 1 M hydrochloric acid and extracted with methylene chloride. The combined extracts are evaporated down and chromatographed through a silica gel column with cyclohexane/ethyl acetate/methanol (6:4:0 to 5:4:1) as eluant.

Yield: 250 mg of (74% of theory)

Mass spectrum (ESI$^+$): m/z=547 [M+H]$^+$

EXAMPLE LX

Ethyl 3,4-dimethyl-6,7-dihydro-5H-[2]pyrindin-1-carboxylate

Prepared by treating 1.16 g of ethyl 3,4-dimethyl-4a-(pyrrolidin-1-yl)-5,6,7,7a-tetrahydro-4aH-[2]pyrindin-1-carboxylate with 1.08 g of 70% 3-chloro-perbenzoic acid in 50 ml methylene chloride at ambient temperature.

Yield: 850 mg (97% of theory)

$R_f$ value: 0.30 (aluminium oxide, petroleum ether/ethyl acetate=5:1)

Mass spectrum (ESI$^+$): m/z=220 [M+H]$^+$

The following compounds are obtained analogously to Example LX:

(1) ethyl 3,4-dimethyl-5,6,7,8-tetrahydro-isoquinoline-1-carboxylate $R_f$ value: 0.35 (aluminium oxide, petroleum ether/ethyl acetate=5:1)

Mass spectrum (ESI$^+$): m/z=234 [M+H]$^+$

EXAMPLE LXI

Ethyl 3,4-dimethyl-4a-(pyrrolidin-1-yl)-5,6,7,7a-tetrahydro-4aH-[2]pyrindin-1-carboxylate Prepared by reacting 2.50 g of ethyl 5,6-dimethyl-[1,2,4]triazin-3-carboxylate with 2.74 g of 1-(cyclopenten-1-yl)-pyrrolidine in 25 ml chloroform at ambient temperature.

Yield: 3.00 g (75% of theory)

$R_f$ value: 0.60 (aluminium oxide, petroleum ether/ethyl acetate=5:1)

Mass spectrum (ESI$^+$): m/z=291 [M+H]$^+$

The following compounds are obtained analogously to Example LXI:

(1) ethyl 3,4-dimethyl-4a-(pyrrolidin-1-yl)-4a,5,6,7,8,8a-hexahydro-isoquinoline-1-carboxylate $R_f$ value: 0.60 (aluminium oxide, petroleum ether/ethyl acetate=5:1)

Mass spectrum (ESI$^+$): m/z=305 [M+H]$^+$

EXAMPLE LXII

Methyl 2,3,8-trimethyl-quinoxalin-6-carboxylate

Prepared by reacting 1.60 g of methyl 3,4-diamino-5-methyl-benzoate with 0.86 ml diacetyl in a mixture of water and ethanol while refluxing.

Yield: 1.53 g (80% of theory)

$R_f$ value: 0.63 (silica gel, cyclohexane/ethyl acetate=1:1)

Mass spectrum (ESI$^+$): m/z=231 [M+H]$^+$

The following compounds are obtained analogously to Example LXII:

(1) methyl 8-methyl-quinoxalin-6-carboxylate (reaction is carried out with glyoxal in water.)

$R_f$ value: 0.55 (silica gel, cyclohexane/ethyl acetate=1:1)

Mass spectrum (ESI$^+$): m/z=203 [M+H]$^+$ (2) 5-bromo-7-methyl-quinoxaline (reaction is carried out with glyoxal in a water/ethanol mixture.)

$R_f$ value: 0.75 (silica gel, methylene chloride/methanol=95:5)

Mass spectrum (ESI$^+$): m/z=223, 225 [M+H]$^+$

EXAMPLE LXIII

Methyl 3,4-diamino-5-methyl-benzoate

Prepared by reduction of methyl 3-nitro-4-amino-5-methyl-benzoate at a partial hydrogen pressure of 50 psi in the presence of Raney nickel in methanol at ambient temperature.

$R_f$ value: 0.40 (silica gel, tert.-butylmethylether)

EXAMPLE LXIV

Methyl 3-nitro-4-amino-5-methyl-benzoate

Prepared by treating 3-nitro-4-acetylamino-5-methyl-benzoic acid with hydrogen chloride gas in methanol at ambient temperature and subsequently heating while refluxing.

Mass spectrum (ESI$^+$): m/z=211 [M+H]$^+$ $R_f$ value: 0.75 (silica gel, tert.-butylmethylether/acetic acid=99:1)

EXAMPLE LXV 1-(2-phenyl-2-oxo-ethyl)-3-methyl-7-((E)-1-buten-1-yl)-8-bromo-xanthine 0.13 ml 35% hydrogen peroxide solution are added to 290 mg of 1-(2-phenyl-2-oxo-ethyl)-3-methyl-7-(1-phenylsulphanyl-butyl)-8-bromo-xanthine in 6 ml hexafluoroisopropanol. The reaction mixture is stirred for one hour at ambient temperature, diluted with methylene chloride and washed with sodium thiosulphate solution. The organic phase is dried over magnesium sulphate and evaporated down. The flask residue is taken up in 6 ml of toluene and refluxed for eight hours. Then the toluene is distilled off in vacuo and the crude product is purified through a silica gel column with methylene chloride/methanol (100:0 to 95:5) as eluant.

Yield: 104 mg (45% of theory)

$R_f$ value: 0.61 (silica gel, methylene chloride/methanol=95:5)

Mass spectrum (ESI$^+$): m/z=417, 419 [M+H]$^+$

The following compounds are obtained analogously to Example LXV:

(1) 3-methyl-7-(3-methyl-1-buten-1-yl)-8-bromo-xanthine $R_f$ value: 0.24 (silica gel, methylene chloride/methanol=95:5)

Mass spectrum (ESI$^+$): m/z=313, 315 [M+H]$^+$

EXAMPLE LXVI 1-methanesulphonyloxymethyl-4-difluoromethoxy-naphthalene

Prepared by reacting (4-difluoromethoxy-naphthalen-1-yl)-methanol with methanesulphonic acid chloride in methylene chloride in the presence of triethylamine.

The following compounds are obtained analogously to Example LXVI:
(1) (E)-1-methanesulphonyloxy-3-(2-nitro-phenyl)-2-propene
(2) (E)-1-methanesulphonyloxy-3-pentafluorophenyl-2-propene
(3) (E)-1-methanesulphonyloxy-3-(2-trifluoromethyl-phenyl)-2-propene
(4) (E)-1-methanesulphonyloxy-3-(3-trifluoromethyl-phenyl)-2-propene
(5) (E)-1-methanesulphonyloxy-3-(4-trifluoromethyl-phenyl)-2-propene

EXAMPLE LXVII 7-methyl-5-phenyl-quinoxaline

A mixture of 400 mg of 5-bromo-7-methyl-quinoxaline, 244 mg of phenylboric acid and 100 mg of tetrakis(triphenylphosphine)palladium in 12 ml dioxane, 4 ml of methanol and 3.6 ml 1 M aqueous sodium carbonate solution is refluxed for three hours under an argon atmosphere. Then the reaction mixture is evaporated down and the residue is distributed between ethyl acetate and water. The ethyl acetate phase is separated off, dried over magnesium sulphate and evaporated down. The crude product is purified by chromatography over a silica gel column with cyclohexane/ethyl acetate (85:15 to 70:30) as eluant.

Yield: 390 mg (66% of theory)
$R_f$ value: 0.36 (silica gel, petroleum ether/ethyl acetate=5:1)
Mass spectrum (ESI$^+$): m/z=221 [M+H]$^+$

EXAMPLE LXVIII 1-methyl-3-trifluoromethyl-isoquinoline

Prepared by treating 905 mg of 1-chloromethyl-3-trifluoromethyl-3,4-dihydro-isoquinoline with 420 mg of potassium-tert. butoxide in 10 ml of tetrahydrofuran at ambient temperature.

Yield: 755 mg of (98% of theory)
Mass spectrum (ESI$^+$): m/z=212 [M+H]$^+$
The following compounds are obtained analogously to Example LXVIII:
(1) 1-methyl-3-difluoromethyl-isoquinoline
(Prepared from 1-methyl-3-trifluoromethyl-3,4-dihydro-isoquinoline)
Mass spectrum (ESI$^+$): m/z=194 [M+H]$^+$

EXAMPLE LXIX 4-chloro-3-methoxy-1-methyl-isoquinoline

Prepared by treating 3-methoxy-1-methyl-isoquinoline with sulphuryl chloride in methylene chloride.
$R_f$ value: 0.30 (silica gel, cyclohexane)
Mass spectrum (ESI$^+$): m/z=208, 210 [M+H]$^+$

EXAMPLE LXX 3-cyclopropyl-8-bromo-xanthine

Prepared by reacting 3-cyclopropyl-xanthine with bromine in the presence of potassium carbonate in acetonitrile at 60° C.
$R_f$ value: 0.65 (ready-made reversed phase TLC plate (E. Merck), acetonitrile/water/trifluoroacetic acid=50:50:1)
Mass spectrum (ESI$^+$): m/z=271, 273 [M+H]$^+$

EXAMPLE LXXI

Ethyl 1,2,3,4-tetrahydro-phenanthridin-6-yl-carboxylate

Analogously to the method described by Gonsalves et al. (*Tetrahedron* 1992, 48, 6821) a solution of 3.90 g of ethyl 5,6,7,8-tetrahydro-benzo[1,2,4]triazin-3-carboxylate (Sagi et al., *Heterocycles* 1989, 29, 2253) in 20 ml dioxane is refluxed. Then 8.22 g of anthranilic acid and 7.02 g of isoamylnitrite, in each case dissolved in 20 ml dioxane, are simultaneously added dropwise within 25 minutes by means of two dropping funnels. The reaction mixture is refluxed for a further 30 minutes. For working up the cooled deep-brown reaction solution is diluted with 150 ml diethyl ether, washed with 100 ml of 2 N sodium hydroxide solution and with water, dried over magnesium sulphate and evaporated down. The brown, oily flask residue is chromatographed through a silica gel column with ethyl acetate/petroleum ether (20:80 to 50:50) as eluant. The product obtained is still somewhat contaminated, but is reacted further without any more purification.

Yield: 380 mg (8% of theory)
$R_f$ value: 0.55 (silica gel, petroleum ether/ethyl acetate=2:1)
Mass spectrum (ESI$^+$): m/z=256 [M+H]$^+$
Preparation of the final compounds:

EXAMPLE 1

1,3-dimethyl-7-(2,6-dicyano-benzyl)-8-(3-amino-piperidin-1-yl)-xanthine 129 mg of 3-amino-piperidine-dihydrochloride are added to a mixture of 298 mg of 1,3-dimethyl-7-(2,6-dicyano-benzyl)-8-bromo-xanthine and 420 mg of potassium carbonate in 9 ml of N,N-dimethylformamide. The reaction mixture is stirred for three hours at 80° C. For working up the mixture is diluted with methylene chloride and washed with saturated sodium chloride solution. The organic phase is dried over magnesium sulphate and evaporated down. The crude product is purified by chromatography through a silica gel column with methylene chloride/methanol/conc. methanolic ammonia (95:5:1 to 80:20:1) as eluant.

Yield: 43 mg (14% of theory)
$R_f$ value: 0.67 (silica gel, methylene chloride/methanol/conc. aqueous ammonia=80:20:1)
Mass spectrum (ESI$^+$): m/z=419 [M+H]$^+$
The following compounds are obtained analogously to Example 1:
(1) 1-(2-cyano-ethyl)-3-methyl-7-(2-cyano-benzyl)-8-(3-amino-piperidin-1-yl)-xanthine
$R_f$ value: 0.35 (silica gel, methylene chloride/methanol=9:1)
Mass spectrum (ESI$^+$): m/z=433 [M+H]$^+$

EXAMPLE 2

1-(2-{2-[(ethoxycarbonyl)methoxy]-phenyl}-2-oxo-ethyl)-3-methyl-7-(3-methyl-2-buten-1-yl)-8-(3-amino-piperidin-1-yl)-xanthine A solution of 209 mg of 1-(2-{2-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine in 4 ml methylene chloride is combined with 1 ml of trifluoroacetic acid and stirred for half an hour at ambient temperature. For working up the reaction mixture is diluted with methylene chloride and washed with saturated potassium carbonate solution. The organic phase is dried, evaporated down and chromatographed through a silica gel column with methylene chloride/methanol (1:0 to 4:1) as eluant.

Yield: 153 mg of (87% of theory)

Mass spectrum (ESI$^+$): m/z=553 [M+H]$^+$

The following compounds are obtained analogously to Example 2:

(1) 1-(2-{2-[(aminocarbonyl)methoxy]-phenyl}-2-oxo-ethyl)-3-methyl-7-(3-methyl-2-buten-1-yl)-8-(3-amino-piperidin-1-yl)-xanthine Mass spectrum (ESI$^+$): m/z=524 [M+H]$^+$ (2) 1-(2-{3-[(methanesulphinyl)methoxy]-phenyl}-2-oxo-ethyl)-3-methyl-7-(3-methyl-2-buten-1-yl)-8-(3-amino-piperidin-1-yl)-xanthine R$_f$ value: 0.58 (ready-made reversed phase TLC plate (E. Merck), acetonitrile/water/trifluoroacetic acid=100:100:0.1)

Mass spectrum (ESI$^+$): m/z=543 [M+H]$^+$ (3) 1-(1-methyl-2-oxo-2-phenyl-ethyl)-3-methyl-7-(3-methyl-2-buten-1-yl)-8-(3-amino-piperidin-1-yl)-xanthine Mass spectrum (ESI$^+$): m/z=465 [M+H]$^+$ (4) 1-(2-phenoxy-ethyl)-3-methyl-7-(2-cyano-benzyl)-8-(3-amino-piperidin-1-yl)-xanthine R$_f$ value: 0.50 (silica gel, methylene chloride/methanol=9:1)

Mass spectrum (ESI$^+$): m/z=500 [M+H]$^+$ (5) 1-(2-phenyl-2-oxo-ethyl)-7-(3-methyl-2-buten-1-yl)-8-(3-amino-piperidin-1-yl)-xanthine R$_f$ value: 0.58 (silica gel, methylene chloride/methanol/conc. aqueous ammonia=80:20:1)

Mass spectrum (ESI$^-$): m/z=435 [M-H]

(6) 1-(2-{3-[(ethoxycarbonyl)methoxy]-phenyl}-2-oxo-ethyl)-3-methyl-7-(3-methyl-2-buten-1-yl)-8-(3-amino-piperidin-1-yl)-xanthine Mass spectrum (ESI$^+$): m/z=553 [M+H]$^+$ (7) 1-(2-{2-[(methylaminocarbonyl)methoxy]-phenyl}-2-oxo-ethyl)-3-methyl-7-(3-methyl-2-buten-1-yl)-8-(3-amino-piperidin-1-yl)-xanthine Mass spectrum (ESI$^+$): m/z=538 [M+H]$^+$ (8) 1-(2-{2-[(di methylaminocarbonyl)methoxy]-phenyl}-2-oxo-ethyl)-3-methyl-7-(3-methyl-2-buten-1-yl)-8-(3-amino-piperidin-1-yl)-xanthine Mass spectrum (ESI$^+$): m/z=552 [M+H]$^+$ (9) 1-(2-methoxy-ethyl)-3-methyl-7-(2-cyano-benzyl)-8-(3-amino-piperidin-1-yl)-xanthine R$_f$ value: 0.40 (silica gel, methylene chloride/methanol=9:1)

Mass spectrum (ESI$^+$): m/z=438 [M+H]$^+$

(10) 1-methyl-3-[(methoxycarbonyl)methyl]-7-(2-cyano-benzyl)-8-(3-amino-piperidin-1-yl)-xanthine R$_f$ value: 0.40 (silica gel, methylene chloride/methanol=9:1)

Mass spectrum (ESI$^+$): m/z=452 [M+H]$^+$

(11) 1-methyl-3-cyanomethyl-7-(2-cyano-benzyl)-8-(3-amino-piperidin-1-yl)-xanthine (Carried out with 5-6 M isopropanolic hydrochloric acid in methylene chloride)

R$_f$ value: 0.20 (silica gel, methylene chloride/methanol=9:1)

Mass spectrum (ESI$^+$): m/z=419 [M+H]$^+$

(12) 1-methyl-3-(2-propyn-1-yl)-7-(2-cyano-benzyl)-8-(3-amino-piperidin-1-yl)-xanthine R$_f$ value: 0.40 (silica gel, methylene chloride/methanol=9:1)

Mass spectrum (ESI$^+$): m/z=418 [M+H]$^+$

(13) 1-{2-[3-(2-oxo-imidazolidin-1-yl)-phenyl]-2-oxo-ethyl}-3-methyl-7-(3-methyl-2-buten-1-yl)-8-(3-amino-piperidin-1-yl)-xanthine R$_f$ value: 0.54 (ready-made reversed phase TLC plate (E. Merck), acetonitrile/water/trifluoroacetic acid=100:100:0.1)

Mass spectrum (ESI$^+$): m/z=535 [M+H]$^+$

(14) 1-methyl-3-(2-propen-1-yl)-7-(2-cyano-benzyl)-8-(3-amino-piperidin-1-yl)-xanthine R$_f$ value: 0.40 (silica gel, methylene chloride/methanol=9:1)

Mass spectrum (ESI$^+$): m/z=420 [M+H]$^+$

(15) 1-(2-phenyl-2-oxo-ethyl)-3-methyl-7-(2-butyn-1-yl)-8-(3-amino-piperidin-1-yl)-xanthine Mass spectrum (ESI$^+$): m/z=435 [M+H]$^+$

(16) 1-(2-{2-[(ethylcarbonyl)amino]-phenyl}-2-oxo-ethyl)-3-methyl-7-(3-methyl-2-buten-1-yl)-8-(3-amino-piperidin-1-yl)-xanthine R$_f$ value: 0.50 (ready-made reversed phase TLC plate (E. Merck), acetonitrile/water/trifluoroacetic acid=100:100:0.1)

Mass spectrum (ESI$^+$): m/z=522 [M+H]$^+$

(17) 1-methyl-3-phenyl-7-(2-cyano-benzyl)-8-(3-amino-piperidin-1-yl)-xanthine

R$_f$ value: 0.40 (silica gel, methylene chloride/methanol=9:1)

Mass spectrum (ESI$^+$): m/z=456 [M+H]$^+$

(18) 1-[2-(2-amino-phenyl)-2-oxo-ethyl]-3-methyl-7-(3-methyl-2-buten-1-yl)-8-((S)-3-amino-piperidin-1-yl)-xanthine R$_f$ value: 0.50 (ready-made reversed phase TLC plate (E. Merck), acetonitrile/water/trifluoroacetic acid=50:50:0.1)

Mass spectrum (ESI$^+$): m/z=466 [M+H]$^+$

(19) 1-(2-phenyl-2-oxo-ethyl)-3-cyanomethyl-7-(3-methyl-2-buten-1-yl)-8-(3-amino-piperidin-1-yl)-xanthine R$_f$ value: 0.07 (silica gel, methylene chloride/methanol/conc. aqueous ammonia=90:10:1)

Mass spectrum (ESI$^+$): m/z=476 [M+H]$^+$

(20) 1-[(quinolin-2-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.50 (silica gel, methylene chloride/methanol/conc. aqueous ammonia=90:10:1)

Mass spectrum (ESI$^+$): m/z=474 [M+H]$^+$

(21) 1-[(2-oxo-2H-chromen-4-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

Mass spectrum (ESI$^+$): m/z=491 [M+H]$^+$

R$_f$ value: 0.16 (silica gel, methylene chloride/methanol/conc. aqueous ammonia=95:5:0.1)

(22) 1-[(cinnolin-4-yl)methyl]-3-methyl-7-(3-methyl-2-buten-1-yl)-8-(3-amino-piperidin-1-yl)-xanthine (1:1 mixture with 1-[(1,4-dihydro-cinnolin-4-yl)methyl]-3-methyl-7-(3-methyl-2-buten-1-yl)-8-(3-amino-piperidin-1-yl)-xanthine)

(Carried out with 5-6 M isopropanolic hydrochloric acid in methylene chloride)

$R_f$ value: 0.49 (silica gel, methylene chloride/methanol/conc. aqueous ammonia=90:10:1)

Mass spectrum (ESI$^+$): m/z=475 [M+H]$^+$

(23) 1-[(1-methyl-2-oxo-1,2-di hydro-quinolin-4-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

Melting point: 178-181° C.

Mass spectrum (ESI$^+$): m/z=504 [M+H]$^+$

(24) 1-[(4-oxo-3,4-dihydro-phthalazin-1-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.06 (silica gel, methylene chloride/methanol/conc. aqueous ammonia=95:5:0.1)

Mass spectrum (ESI$^+$): m/z=491 [M+H]$^+$

(25) 1-[(quinazolin-4-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.48 (silica gel, methylene chloride/methanol/conc. aqueous ammonia=90:10:1)

Mass spectrum (ESI$^+$): m/z=475 [M+H]$^+$

(26) 1-[(5-methyl-3-phenyl-isoxazol-4-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.40 (silica gel, methylene chloride/methanol/conc. aqueous ammonia=90:10:0.1)

Mass spectrum (ESI$^+$): m/z=504 [M+H]$^+$

(27) 1-[(isoquinoline-3-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.51 (silica gel, methylene chloride/methanol/conc. aqueous ammonia=90:10:1)

Mass spectrum (ESI$^+$): m/z=474 [M+H]$^+$

(28) 1-[(3-phenyl-[1,2,4]oxadiazol-5-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.23 (silica gel, methylene chloride/methanol/conc. aqueous ammonia=95:5:1)

Mass spectrum (ESI$^+$): m/z=491 [M+H]$^+$

(29) 1-[(4-phenyl-pyridin-2-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.51 (silica gel, methylene chloride/methanol/conc. aqueous ammonia=90:10:1)

Mass spectrum (ESI$^+$): m/z=500 [M+H]$^+$

(30) 1-[(5-phenyl-pyridin-2-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.58 (silica gel, methylene chloride/methanol/conc. aqueous ammonia=90:10:1)

Mass spectrum (ESI$^+$): m/z=500 [M+H]$^+$

(31) 1-[(3-methyl-4-oxo-3,4-dihydro-phthalazin-1-yl)methyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

$R_f$ value: 0.55 (silica gel, methylene chloride/methanol/conc. aqueous ammonia=90:10:0.1)

Mass spectrum (ESI$^+$): m/z=505 [M+H]$^+$

(32) 1-[2-(3-methylsulphanyl-phenyl)-2-oxo-ethyl]-3-methyl-7-(3-methyl-2-buten-1-yl)-8-(3-amino-piperidin-1-yl)-xanthine $R_f$ value: 0.34 (silica gel, methylene chloride/methanol/conc. aqueous ammonia=90:10:1)

Mass spectrum (ESI$^+$): m/z=497 [M+H]$^+$

(33) 1-[2-(3-methanesulphinyl-phenyl)-2-oxo-ethyl]-3-methyl-7-(3-methyl-2-buten-1-yl)-8-(3-amino-piperidin-1-yl)-xanthine $R_f$ value: 0.21 (silica gel, methylene chloride/methanol/conc. aqueous ammonia=90:10:1)

Mass spectrum (ESI$^+$): m/z=513 [M+H]$^+$

(34) 1-[2-(3-methanesulphonyl-phenyl)-2-oxo-ethyl]-3-methyl-7-(3-methyl-2-buten-1-yl)-8-(3-amino-piperidin-1-yl)-xanthine $R_f$ value: 0.66 (ready-made reversed phase TLC plate (E. Merck), acetonitrile/water/trifluoroacetic acid=50:50:1)

Mass spectrum (ESI$^+$): m/z=529 [M+H]$^+$

(35) 1-[2-(3-carboxy-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

$R_f$ value: 0.54 (ready-made reversed phase TLC plate (E. Merck), acetonitrile/water/trifluoroacetic acid=50:50:1)

Mass spectrum (ESI$^+$): m/z=495 [M+H]$^+$

(36) 1-[2-(3-methoxycarbonyl-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

$R_f$ value: 0.47 (ready-made reversed phase TLC plate (E. Merck), acetonitrile/water/trifluoroacetic acid=50:50:1)

Mass spectrum (ESI$^+$): m/z=509 [M+H]$^+$

(37) 1-{2-[3-(methylaminocarbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

$R_f$ value: 0.53 (ready-made reversed phase TLC plate (E. Merck), acetonitrile/water/trifluoroacetic acid=50:50:1)

Mass spectrum (ESI$^+$): m/z=508 [M+H]$^+$

(38) 1-{2-[3-(dimethylaminocarbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

$R_f$ value: 0.53 (ready-made reversed phase TLC plate (E. Merck), acetonitrile/water/trifluoroacetic acid=50:50:1)

Mass spectrum (ESI$^+$): m/z=522 [M+H]$^+$

(39) 1-{2-[3-(morpholin-4-yl-carbonyl)-phenyl]-2-oxo-ethyl}-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.53 (ready-made reversed phase TLC plate (E. Merck), acetonitrile/water/trifluoroacetic acid=50:50:1)
Mass spectrum (ESI$^+$): m/z=564 [M+H]$^+$

(40) 1-[2-(2-carboxy-phenyl)-2-oxo-ethyl]-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.53 (ready-made reversed phase TLC plate (E. Merck), acetonitrile/water/trifluoroacetic acid=50:50:1)
Mass spectrum (ESI$^+$): m/z=495 [M+H]$^+$

(41) 1-[2-(2-ethoxycarbonyl-phenyl)-2-oxo-ethyl]-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.41 (ready-made reversed phase TLC plate (E. Merck), acetonitrile/water/trifluoroacetic acid=50:50:1)
Mass spectrum (ESI$^+$): m/z=523 [M+H]$^+$

(42) 1-{2-[2-(dimethylaminocarbonyl)-phenyl]-2-oxo-ethyl}-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.53 (ready-made reversed phase TLC plate (E. Merck), acetonitrile/water/trifluoroacetic acid=50:50:1)
Mass spectrum (ESI$^+$): m/z=522 [M+H]$^+$

(43) 1-{2-[2-(morpholin-4-yl-carbonyl)-phenyl]-2-oxo-ethyl}-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.53 (ready-made reversed phase TLC plate (E. Merck), acetonitrile/water/trifluoroacetic acid=50:50:1)
Mass spectrum (ESI$^+$): m/z=564 [M+H]$^+$

(44) 1-[2-(2,6-di methoxy-phenyl)-2-oxo-ethyl]-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.44 (ready-made reversed phase TLC plate (E. Merck), acetonitrile/water/trifluoroacetic acid=50:50:1)
Mass spectrum (ESI$^+$): m/z=511 [M+H]$^+$

(45) 1-(2-phenyl-2-oxo-ethyl)-3-methyl-7-(2,3-dimethyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.68 (ready-made reversed phase TLC plate (E. Merck), acetonitrile/water/trifluoroacetic acid=50:50:1)
Mass spectrum (ESI$^+$): m/z=465 [M+H]$^+$

(46) 1-((E)-3-phenyl-allyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.38 (silica gel, methylene chloride/methanol/conc. aqueous ammonia=95:5:0.1)
Mass spectrum (ESI$^+$): m/z=449 [M+H]$^+$

(47) 1-[(benzo[b]thiophen-3-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.51 (silica gel, methylene chloride/methanol/conc. aqueous ammonia=90:10:1)
Mass spectrum (ESI$^+$): m/z=479 [M+H]$^+$

(48) 1-[(1H-indol-3-yl)methyl]-3-methyl-7-(3-methyl-2-buten-1-yl)-8-(3-amino-piperidin-1-yl)-xanthine
$R_f$ value: 0.48 (silica gel, methylene chloride/methanol/conc. aqueous ammonia=90:10:1)
Mass spectrum (ESI$^+$): m/z=462 [M+H]$^+$

(49) 1-[(biphenyl-4-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.30 (silica gel, methylene chloride/methanol/conc. aqueous ammonia=95:5:0.1)
Mass spectrum (ESI$^+$): m/z=499 [M+H]$^+$

(50) 1-[(1-naphthyl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.56 (silica gel, methylene chloride/methanol/conc. aqueous ammonia=90:10:1)
Mass spectrum (ESI$^+$): m/z=457 [M+H]$^+$

(51) 1-[(1-methyl-2-oxo-1,2-di hydro-quinolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.40 (silica gel, methylene chloride/methanol/conc. aqueous ammonia=90:10:1)
Mass spectrum (ESI$^+$): m/z=488 [M+H]$^+$

(52) 1-[(quinolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=458 [M+H]$^+$

(53) 1-(2-cyclohexyl-2-oxo-ethyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.48 (silica gel, methylene chloride/methanol/conc. aqueous ammonia=90:10:1)
Mass spectrum (ESI$^+$): m/z=457 [M+H]$^+$

(54) 1-(3,3-dimethyl-2-oxo-butyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.49 (silica gel, methylene chloride/methanol/conc. aqueous ammonia=90:10:1)
Mass spectrum (ESI$^+$): m/z=431 [M+H]$^+$

(55) 1-[(quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=95:5:0.1)
Mass spectrum (ESI$^+$): m/z=459 [M+H]$^+$

(56) 1-[(2-methyl-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.25 (silica gel, methylene chloride/methanol/conc. aqueous ammonia=95:5:0.1)
Mass spectrum (ESI$^+$): m/z=471 [M+H]$^+$

(57) 1-({5-[(methoxycarbonyl)methylamino]-isoquinolin-1-yl}methyl)-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.43 (silica gel, methylene chloride/methanol/conc. aqueous ammonia=90:10:1)

Mass spectrum (ESI$^+$): m/z=561 [M+H]$^+$

(58) 1-(2-di methylamino-2-oxo-ethyl)-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.38 (silica gel, methylene chloride/methanol/conc. aqueous ammonia=90:10:1)

Mass spectrum (ESI$^+$): m/z=418 [M+H]$^+$

(59) 1-[2-(piperidin-1-yl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.35 (silica gel, methylene chloride/methanol/conc. aqueous ammonia=90:10:1)

Mass spectrum (ESI$^+$): m/z=458 [M+H]$^+$

(60) 1-[(2-methyl-1-oxo-1,2-dihydro-isoquinoline-4-yl)methyl]-7-(2-butyn-1-yl)-8-(3-amino-piperidin-1-yl)-xanthine (Carried out with 5-6 M isopropanolic hydrochloric acid in methylene chloride)

$R_f$ value: 0.17 (silica gel, methylene chloride/methanol/conc. aqueous ammonia=95:5:0.1)

Mass spectrum (ESI$^+$): m/z=488 [M+H]$^+$

(61) 1-[(2-methyl-1-oxo-1,2-dihydro-isoquinoline-4-yl)methyl]-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.13 (silica gel, methylene chloride/methanol/conc. aqueous ammonia=95:5:0.1)

Mass spectrum (ESI$^+$): m/z=504 [M+H]$^+$

(62) 1-[(2-methoxy-naphthalen-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.17 (silica gel, methylene chloride/methanol/conc. aqueous ammonia=95:5:0.1)

Mass spectrum (ESI$^+$): m/z=487 [M+H]$^+$

(63) 1-[(isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.42 (silica gel, methylene chloride/methanol/conc. aqueous ammonia=90:10:1)

Mass spectrum (ESI$^+$): m/z=458 [M+H]$^+$

(64) 1-[(4-methoxy-naphthalen-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.14 (silica gel, methylene chloride/methanol/conc. aqueous ammonia=95:5:0.1)

Mass spectrum (ESI$^+$): m/z=487 [M+H]$^+$

(65) 1-[(3-methyl-isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

Melting point: 155-158° C.

Mass spectrum (ESI$^+$): m/z=472 [M+H]$^+$

(66) 1-[2-(2,3-dimethoxy-phenyl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.40 (silica gel, methylene chloride/methanol/conc. aqueous ammonia=90:10:1)

Mass spectrum (ESI$^+$): m/z=511 [M+H]$^+$

(67) 1-[(5-nitro-naphthalen-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.15 (silica gel, methylene chloride/methanol/conc. aqueous ammonia=95:5:0.1)

Mass spectrum (ESI$^+$): m/z=502 [M+H]$^+$

(68) 1-[2-(pyrrolidin-1-yl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

$R_f$ value: 0.56 (silica gel, methylene chloride/methanol/conc. aqueous ammonia=90:10:1)

Mass spectrum (ESI$^+$): m/z=444 [M+H]$^+$

(69) 1-[(4-methyl-isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.46 (silica gel, methylene chloride/methanol/conc. aqueous ammonia=90:10:1)

Mass spectrum (ESI$^+$): m/z=472 [M+H]$^+$

(70) 1-[(2-naphthyl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.20 (silica gel, methylene chloride/methanol/conc. aqueous ammonia=95:5:0.1)

Mass spectrum (ESI$^+$): m/z=457 [M+H]$^+$

(71) 1-[(4-oxo-3,4-dihydro-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.38 (silica gel, methylene chloride/methanol/conc. aqueous ammonia=90:10:0.1)

Mass spectrum (ESI$^+$): m/z=475 [M+H]$^+$

(72) 1-[(quinolin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.15 (silica gel, methylene chloride/methanol/conc. aqueous ammonia=95:5:0.1)

Mass spectrum (ESI$^+$): m/z=458 [M+H]$^+$

(73) 1-[(4-dimethylamino-naphthalen-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.18 (silica gel, methylene chloride/methanol/conc. aqueous ammonia=95:5:0.1)

Mass spectrum (ESI$^+$): m/z=500 [M+H]$^+$

(74) 1-[(isoquinolin-1-yl)methyl]-3-methyl-7-((E)-2-buten-1-yl)-8-(3-amino-piperidin-1-yl)-xanthine (Carried out with 5-6 M isopropanolic hydrochloric acid in methylene chloride; the product still contains approx. 20% of Z isomer)

R$_f$ value: 0.66 (silica gel, methylene chloride/methanol/conc. aqueous ammonia=90:10:0.1)

Mass spectrum (ESI$^+$): m/z=460 [M+H]$^+$

(75) 1-[(3-methoxy-naphthalen-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.25 (silica gel, methylene chloride/methanol/conc. aqueous ammonia=95:5:0.1)

Mass spectrum (ESI$^+$): m/z=487 [M+H]$^+$

(76) 1-[2-(2,3-di hydro-benzo[1,4]dioxin-5-yl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

Mass spectrum (ESI$^+$): m/z=509 [M+H]$^+$

(77) 1-[(3-methyl-4-oxo-3,4-di hydro-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.20 (silica gel, methylene chloride/methanol/conc. aqueous ammonia=95:5:0.1)

Mass spectrum (ESI$^+$): m/z=489 [M+H]$^+$

(78) 1-[2-(3-methyl-2-oxo-2,3-dihydro-benzooxazol-7-yl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.47 (silica gel, methylene chloride/methanol/conc. aqueous ammonia=90:10:1)

Mass spectrum (ESI$^+$): m/z=522 [M+H]$^+$

(79) 1-[2-(benzo[1,3]dioxol-4-yl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

Mass spectrum (ESI$^+$): m/z=495 [M+H]$^+$

(80) 1-[(quinazolin-2-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

Mass spectrum (ESI$^+$): m/z=459 [M+H]$^+$

(81) 1-[(quinazolin-2-yl)methyl]-3-methyl-7-(2-butyn-1-yl)-8-((S)-3-amino-piperidin-1-yl)-xanthine (Carried out with 5-6 M isopropanolic hydrochloric acid in methylene chloride)

Mass spectrum (ESI$^+$): m/z=459 [M+H]$^+$

(82) 1-[(quinazolin-2-yl)methyl]-3-methyl-7-((E)-2-buten-1-yl)-8-((S)-3-amino-piperidin-1-yl)-xanthine (Carried out with 5-6 M isopropanolic hydrochloric acid in methylene chloride; the product still contains approx. 20% of Z isomer)

R$_f$ value: 0.12 (silica gel, methylene chloride/methanol/conc. aqueous ammonia=95:5:0.1)

Mass spectrum (ESI$^+$): m/z=461 [M+H]$^+$

(83) 1-[(quinazolin-2-yl)methyl]-3-methyl-7-((E)-2-buten-1-yl)-8-((R)-3-amino-piperidin-1-yl)-xanthine (Carried out with 5-6 M isopropanolic hydrochloric acid in methylene chloride; the product still contains approx. 15% of Z isomer)

R$_f$ value: 0.12 (silica gel, methylene chloride/methanol/conc. aqueous ammonia=95:5:0.1)

Mass spectrum (ESI$^+$): m/z=461 [M+H]$^+$

(84) 1-[(3-methyl-isoquinolin-1-yl)methyl]-3-methyl-7-((E)-2-buten-1-yl)-8-((R)-3-amino-piperidin-1-yl)-xanthine (Carried out with 5-6 M isopropanolic hydrochloric acid in methylene chloride; the product still contains approx. 17% of Z isomer)

R$_f$ value: 0.54 (silica gel, methylene chloride/methanol/conc. aqueous ammonia=90:10:1)

Mass spectrum (ESI$^+$): m/z=474 [M+H]$^+$

(85) 1-[(3-methyl-isoquinolin-1-yl)methyl]-3-methyl-7-((E)-2-buten-1-yl)-8-((S)-3-amino-piperidin-1-yl)-xanthine (Carried out with 5-6 M isopropanolic hydrochloric acid in methylene chloride; the product still contains approx. 17% of Z isomer)

R$_f$ value: 0.54 (silica gel, methylene chloride/methanol/conc. aqueous ammonia=90:10:1)

Mass spectrum (ESI$^+$): m/z=474 [M+H]$^+$

(86) 1-(2-{2-[(ethylaminocarbonyl)methoxy]-phenyl}-2-oxo-ethyl)-3-methyl-7-(2-butyn-1-yl)-8-((R)-3-amino-piperidin-1-yl)-xanthine Mass spectrum (ESI$^+$): m/z=536 [M+H]$^+$

(87) 1-[2-(2-amino-phenyl)-2-oxo-ethyl]-3-methyl-7-[(1-cyclopenten-1-yl)methyl]-8-(3-amino-piperidin-1-yl)-xanthine Mass spectrum (ESI$^+$): m/z=478 [M+H]$^+$

(88) 1-(2-phenyl-2-oxo-ethyl)-3-methyl-7-[(1-cyclopenten-1-yl)methyl]-8-(3-amino-piperidin-1-yl)-xanthine Mass spectrum (ESI$^+$): m/z=463 [M+H]$^+$

(89) 1-(2-{2-[(methylaminocarbonyl)methoxy]-phenyl}-2-oxo-ethyl)-3-methyl-7-[(1-cyclopenten-1-yl)methyl]-8-(3-amino-piperidin-1-yl)-xanthine Mass spectrum (ESI$^+$): m/z=550 [M+H]$^+$

(90) 1-methyl-3-isopropyl-7-(2-cyano-benzyl)-8-(3-amino-piperidin-1-yl)-xanthine R$_f$ value: 0.40 (silica gel, methylene chloride/methanol=9:1)

Mass spectrum (ESI$^+$): m/z=422 [M+H]$^+$

(91) 1-(2-{2-[(methylaminocarbonyl)methoxy]-phenyl}-2-oxo-ethyl)-3-methyl-7-(2-butyn-1-yl)-8-(3-amino-piperidin-1-yl)-xanthine Mass spectrum (ESI$^+$): m/z=522 [M+H]$^+$

(92) 1-(2-{2-[(aminocarbonyl)methoxy]-phenyl}-2-oxo-ethyl)-3-methyl-7-(2-butyn-1-yl)-8-(3-amino-piperidin-1-yl)-xanthine Mass spectrum (ESI$^+$): m/z=508 [M+H]$^+$

(93) 1-[2-(2-cyanomethylamino-phenyl)-2-oxo-ethyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.50 (ready-made reversed phase TLC plate (E. Merck), acetonitrile/water/trifluoroacetic acid=50:50:1)

Mass spectrum (ESI$^+$): m/z=505 [M+H]$^+$

(94) 1-(2-{2-[(isopropylaminocarbonyl)methoxy]-phenyl}-2-oxo-ethyl)-3-methyl-7-(2-butyn-1-yl)-8-(3-amino-piperidin-1-yl)-xanthine R$_f$ value: 0.30 (silica gel, methylene chloride/methanol=9:1)

Mass spectrum (ESI$^+$): m/z=550 [M+H]$^+$

(95) 1-[(isoquinolin-1-yl)methyl]-3-[(methoxycarbonyl)methyl]-7-(3-methyl-2-buten-1-yl)-8-(3-amino-piperidin-1-yl)-xanthine R$_f$ value: 0.21 (silica gel, methylene chloride/methanol/conc. aqueous ammonia=90:10:1)

Mass spectrum (ESI$^+$): m/z=532 [M+H]$^+$

(96) 1-[2-(2-acetylamino-phenyl)-2-oxo-ethyl]-3-methyl-7-((E)-2-buten-1-yl)-8-(3-amino-piperidin-1-yl)-xanthine
(product contains approx. 10% of Z isomer)
Mass spectrum (ESI⁺): m/z=494 [M+H]⁺

(97) 1-(2-phenyl-2-oxo-ethyl)-3-methyl-7-((E)-2-buten-1-yl)-8-(3-amino-piperidin-1-yl)-xanthine
(product contains approx. 25% of Z isomer)
$R_f$ value: 0.30 (silica gel, methylene chloride/methanol=9:1)
Mass spectrum (ESI⁺): m/z=437 [M+H]⁺

(98) 1-(2-{2-[(isopropyloxycarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI⁺): m/z=567 [M+H]⁺

(99) 1-(2-{2-[(methylaminocarbonyl)methoxy]-phenyl}-2-oxo-ethyl)-3-methyl-7-(2-butyn-1-yl)-8-((R)-3-amino-piperidin-1-yl)-xanthine
Mass spectrum (ESI⁺): m/z=522 [M+H]⁺

(100) 1-(2-{2-[(isopropylcarbonyl)amino]-phenyl}-2-oxo-ethyl)-3-methyl-7-((E)-2-buten-1-yl)-8-(3-amino-piperidin-1-yl)-xanthine (product contains approx. 10% of Z isomer)
Mass spectrum (ESI⁺): m/z=522 [M+H]⁺

(101) 1-(2-{2-[(methylaminocarbonyl)methoxy]-phenyl}-2-oxo-ethyl)-3-methyl-7-((E)-2-buten-1-yl)-8-(3-amino-piperidin-1-yl)-xanthine
(product contains approx. 8% of Z isomer)
$R_f$ value: 0.51 (ready-made reversed phase TLC plate (E. Merck), acetonitrile/water/trifluoroacetic acid=50:50:0.1)
Mass spectrum (ESI⁺): m/z=524 [M+H]⁺

(102) 1-(2-{2-[(ethylaminocarbonyl)methoxy]-phenyl}-2-oxo-ethyl)-3-methyl-7-(2-butyn-1-yl)-8-((S)-3-amino-piperidin-1-yl)-xanthine
Mass spectrum (ESI⁺): m/z=536 [M+H]⁺

(103) 1-[2-(2-{[(ethoxycarbonylamino)carbonyl]amino}-phenyl)-2-oxo-ethyl]-3-methyl-7-(3-methyl-2-buten-1-yl)-8-(3-amino-piperidin-1-yl)-xanthine
Mass spectrum (ESI⁺): m/z=581 [M+H]⁺

(104) 1-[2-(2-amino-phenyl)-2-oxo-ethyl]-3-methyl-7-((E)-2-buten-1-yl)-8-(3-amino-piperidin-1-yl)-xanthine
$R_f$ value: 0.54 (ready-made reversed phase TLC plate (E. Merck), acetonitrile/water/trifluoroacetic acid=50:50:0.1)
Mass spectrum (ESI⁺): m/z=452 [M+H]⁺

(105) 1-[2-(2-acetylamino-phenyl)-2-oxo-ethyl]-3-methyl-7-(3-methyl-2-buten-1-yl)-8-((S)-3-amino-piperidin-1-yl)-xanthine
$R_f$ value: 0.48 (ready-made reversed phase TLC plate (E. Merck), acetonitrile/water/trifluoroacetic acid=50:50:0.1)
Mass spectrum (ESI⁺): m/z=508 [M+H]⁺

(106) 1-[2-(2-amino-phenyl)-2-oxo-ethyl]-3-methyl-7-(2-butyn-1-yl)-8-(3-amino-piperidin-1-yl)-xanthine
$R_f$ value: 0.31 (silica gel, methylene chloride/methanol/conc. aqueous ammonia=90:10:1)
Mass spectrum (ESI⁺): m/z=450 [M+H]⁺

(107) 1-(2-{2-[(methylaminocarbonyl)methoxy]-phenyl}-2-oxo-ethyl)-3-methyl-7-(2-butyn-1-yl)-8-((S)-3-amino-piperidin-1-yl)-xanthine
Mass spectrum (ESI⁺): m/z=522 [M+H]⁺

(108) 1-(2-phenyl-2-oxo-ethyl)-3-methyl-7-((E)-2-buten-1-yl)-8-((R)-3-amino-piperidin-1-yl)-xanthine (product contains approx. 22% of Z isomer)
Mass spectrum (ESI⁺): m/z=437 [M+H]⁺

(109) 1-(2-{2-[(ethylaminocarbonyl)methoxy]-phenyl}-2-oxo-ethyl)-3-methyl-7-(2-butyn-1-yl)-8-(3-amino-piperidin-1-yl)-xanthine
$R_f$ value: 0.40 (silica gel, methylene chloride/methanol=9:1)
Mass spectrum (ESI⁺): m/z=536 [M+H]⁺

(110) 1-[2-(2-acetylamino-phenyl)-2-oxo-ethyl]-3-methyl-7-(2-butyn-1-yl)-8-(3-amino-piperidin-1-yl)-xanthine
$R_f$ value: 0.23 (silica gel, methylene chloride/methanol/conc. aqueous ammonia=90:10:1)
Mass spectrum (ESI⁺): m/z=492 [M+H]⁺

(111) 1-(2-{2-[2-oxo-2-(pyrrolidin-1-yl)-ethoxy]-phenyl}-2-oxo-ethyl)-3-methyl-7-(2-butyn-1-yl)-8-(3-amino-piperidin-1-yl)-xanthine
$R_f$ value: 0.20 (silica gel, methylene chloride/methanol=9:1)
Mass spectrum (ESI⁺): m/z=562 [M+H]⁺

(112) 1-(2-{2-[(methylaminocarbonyl)methoxy]-phenyl}-2-oxo-ethyl)-3-methyl-7-(3-methyl-2-buten-1-yl)-8-((S)-3-amino-piperidin-1-yl)-xanthine
Mass spectrum (ESI⁺): m/z=538 [M+H]⁺

(113) 1-(2-phenyl-2-oxo-ethyl)-3-methyl-7-(2-butyn-1-yl)-8-((R)-3-amino-piperidin-1-yl)-xanthine
Mass spectrum (ESI⁺): m/z=435 [M+H]⁺

(114) 1-(2-{2-[(ethylaminocarbonyl)methoxy]-phenyl}-2-oxo-ethyl)-3-methyl-7-((E)-2-buten-1-yl)-8-((R)-3-amino-piperidin-1-yl)-xanthine (product contains approx. 30% of Z isomer)
Mass spectrum (ESI⁺): m/z=538 [M+H]⁺

(115) 1-methyl-7-(2-cyano-benzyl)-8-(3-amino-piperidin-1-yl)-xanthine
Mass spectrum (ESI⁺): m/z=380 [M+H]⁺

(116) 1-(2-{2-[(isopropylcarbonyl)amino]-phenyl}-2-oxo-ethyl)-3-methyl-7-(3-methyl-2-buten-1-yl)-8-(3-amino-piperidin-1-yl)-xanthine
$R_f$ value: 0.40 (ready-made reversed phase TLC plate (E. Merck), acetonitrile/water/trifluoroacetic acid=50:50:0.1)
Mass spectrum (ESI⁺): m/z=536 [M+H]⁺

(117) 1-(2-phenyl-2-oxo-ethyl)-3-methyl-7-((E)-2-buten-1-yl)-8-((S)-3-amino-piperidin-1-yl)-xanthine (product contains approx. 23% of Z isomer)
$R_f$ value: 0.42 (ready-made reversed phase TLC plate (E. Merck), acetonitrile/water/trifluoroacetic acid=50:50:0.1)
Mass spectrum (ESI⁺): m/z=437 [M+H]⁺

(118) 1-(2-{2-[(isopropylcarbonyl)amino]-phenyl}-2-oxo-ethyl)-3-methyl-7-(2-butyn-1-yl)-8-(3-amino-piperidin-1-yl)-xanthine
$R_f$ value: 0.20 (silica gel, methylene chloride/methanol/conc. aqueous ammonia=90:10:1)
Mass spectrum (ESI⁺): m/z=520 [M+H]⁺

(119) 1-[2-(2-acetylamino-phenyl)-2-oxo-ethyl]-3-methyl-7-(2-butyn-1-yl)-8-((S)-3-amino-piperidin-1-yl)-xanthine
$R_f$ value: 0.15 (silica gel, methylene chloride/methanol/conc. aqueous ammonia=90:10:1)
Mass spectrum (ESI⁺): m/z=492 [M+H]⁺

(120) 1-(2-{2-[(isopropylcarbonyl)amino]-phenyl}-2-oxo-ethyl)-3-methyl-7-(2-butyn-1-yl)-8-((S)-3-amino-piperidin-1-yl)-xanthine
Mass spectrum (ESI⁺): m/z=520 [M+H]⁺

(121) 1-(2-phenyl-2-oxo-ethyl)-3-methyl-7-(2-methyl-allyl)-8-(3-amino-piperidin-1-yl)-xanthine
$R_f$ value: 0.21 (silica gel, methylene chloride/methanol/conc. aqueous ammonia=90:10:1)
Mass spectrum (ESI⁺): m/z=437 [M+H]⁺

(122) 1-(2-phenyl-2-oxo-ethyl)-3-methyl-7-(3-bromo-allyl)-8-(3-amino-piperidin-1-yl)-xanthine
$R_f$ value: 0.14 (silica gel, methylene chloride/methanol/conc. aqueous ammonia=90:10:1)
Mass spectrum (ESI$^+$): m/z=501, 503 [M+H]$^+$ (123) 1-(2-{2-[(methoxycarbonyl)amino]-phenyl}-2-oxo-ethyl)-3-methyl-7-(3-methyl-2-buten-1-yl)-8-(3-amino-piperidin-1-yl)-xanthine
$R_f$ value: 0.42 (ready-made reversed phase TLC plate (E. Merck), acetonitrile/water/trifluoroacetic acid=50:50:0.1)
Mass spectrum (ESI$^+$): m/z=524 [M+H]$^+$ (124) 1-(2-phenyl-2-oxo-ethyl)-3-methyl-7-[(furan-2-yl)methyl]-8-(3-amino-piperidin-1-yl)-xanthine
$R_f$ value: 0.23 (silica gel, methylene chloride/methanol/conc. aqueous ammonia=90:10:1)
Mass spectrum (ESI$^+$): m/z=463 [M+H]$^+$ (125) 1-(2-phenyl-2-oxo-ethyl)-3-methyl-7-(2-chloro-allyl)-8-(3-amino-piperidin-1-yl)-xanthine
$R_f$ value: 0.18 (silica gel, methylene chloride/methanol/conc. aqueous ammonia=90:10:1)

(126) 1-{2-[2-(1-methoxycarbonyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=537 [M+H]$^+$ (127) 1-{2-[2-(1-aminocarbonyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=522 [M+H]$^+$ (128) 1-(2-phenyl-2-oxo-ethyl)-3-methyl-7-(2-butyn-1-yl)-8-((S)-3-amino-piperidin-1-yl)-xanthine
Mass spectrum (ESI$^+$): m/z=435 [M+H]$^+$ (129) 1-[(3-methyl-isoquinolin-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
Melting point: 155-156.5° C.
Mass spectrum (ESI$^+$): m/z=472 [M+H]$^+$ (130) 1-[(3-methyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=472 [M+H]$^+$ (131) 1-[(4-methyl-isoquinolin-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
$R_f$ value: 0.46 (silica gel, methylene chloride/methanol/conc. aqueous ammonia=90:10:1)
Mass spectrum (ESI$^+$): m/z=472 [M+H]$^+$ (132) 1-[(4-methyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.46 (silica gel, methylene chloride/methanol/conc. aqueous ammonia=90:10:1)
Mass spectrum (ESI$^+$): m/z=472 [M+H]$^+$ (133) 1-[(4-methyl-isoquinolin-1-yl)methyl]-3-methyl-7-((E)-2-buten-1-yl)-8-((S)-3-amino-piperidin-1-yl)-xanthine
(Carried out with 5-6 M isopropanolic hydrochloric acid in methylene chloride)
$R_f$ value: 0.48 (silica gel, methylene chloride/methanol/conc. aqueous ammonia=90:10:1)
Mass spectrum (ESI$^+$): m/z=474 [M+H]$^+$ (134) 1-[(4-methyl-isoquinolin-1-yl)methyl]-3-methyl-7-((E)-2-buten-1-yl)-8-((R)-3-amino-piperidin-1-yl)-xanthine
(Carried out with 5-6 M isopropanolic hydrochloric acid in methylene chloride)
Melting point: 167.5-172° C.
Mass spectrum (ESI$^+$): m/z=474 [M+H]$^+$ (135) 1-[2-(2,3-dihydro-benzo[1,4]dioxin-5-yl)-2-oxo-ethyl]-3-methyl-7-(2-butyn-1-yl)-8-(3-(R)-amino-piperidin-1-yl)-xanthine
(Carried out with 5-6 M isopropanolic hydrochloric acid in methylene chloride)
$R_f$ value: 0.34 (silica gel, methylene chloride/methanol/conc. aqueous ammonia=90:10:1)
Mass spectrum (ESI$^+$): m/z=493 [M+H]$^+$ (136) 1-[2-(2,3-dihydro-benzo[1,4]dioxin-5-yl)-2-oxo-ethyl]-3-methyl-7-(2-butyn-1-yl)-8-(3-(S)-amino-piperidin-1-yl)-xanthine
(Carried out with 5-6 M isopropanolic hydrochloric acid in methylene chloride)
Mass spectrum (ESI$^+$): m/z=493 [M+H]$^+$ (137) 1-[(4-methoxy-naphthalen-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=487 [M+H]$^+$ (138) 1-[(4-methoxy-naphthalen-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=487 [M+H]$^+$ (139) 1-[2-(benzo[1,3]dioxol-4-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.41 (silica gel, methylene chloride/methanol/conc. aqueous ammonia=90:10:1)
Mass spectrum (ESI$^+$): m/z=479 [M+H]$^+$ (140) 1-[2-(benzo[1,3]dioxol-4-yl)-2-oxo-ethyl]-3-methyl-7-(2-butyn-1-yl)-8-((S)-3-amino-piperidin-1-yl)-xanthine
(Carried out with 5-6 M isopropanolic hydrochloric acid in methylene chloride)
Mass spectrum (ESI$^+$): m/z=479 [M+H]$^+$ (141) 1-[(4-methyl-quinazolin-2-yl)methyl]-3-methyl-7-(2-butyn-1-yl)-8-(3-(S)-amino-piperidin-1-yl)-xanthine
(Carried out with 5-6 M isopropanolic hydrochloric acid in methylene chloride)
$R_f$ value: 0.51 (silica gel, methylene chloride/methanol/conc. aqueous ammonia=90:10:1)
Mass spectrum (ESI$^+$): m/z=473 [M+H]$^+$ (142) 1-[(4-methyl-quinazolin-2-yl)methyl]-3-methyl-7-(2-butyn-1-yl)-8-(3-(R)-amino-piperidin-1-yl)-xanthine
(Carried out with 5-6 M isopropanolic hydrochloric acid in methylene chloride)
Melting point: 198-202° C.
Mass spectrum (ESI$^+$): m/z=473 [M+H]$^+$ (143) 1-[2-(3-methyl-2-oxo-2,3-dihydro-benzooxazol-4-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)

R$_f$ value: 0.53 (silica gel, methylene chloride/methanol/conc. aqueous ammonia=90:10:1)
Mass spectrum (ESI$^+$): m/z=522 [M+H]$^+$ (144) 1-(2-{2-[(ethylaminocarbonyl)methoxy]-phenyl}-2-oxo-ethyl)-3-methyl-7-((E)-2-buten-1-yl)-8-((S)-3-amino-piperidin-1-yl)-xanthine
Mass spectrum (ESI$^+$): m/z=538 [M+H]$^+$ (145) 1-(2-{2-[(isopropylcarbonyl)amino]-phenyl}-2-oxo-ethyl)-3-methyl-7-((E)-2-buten-1-yl)-8-((S)-3-amino-piperidin-1-yl)-xanthine
R$_f$ value: 0.49 (ready-made reversed phase TLC plate (E. Merck), acetonitrile/water/trifluoroacetic acid=50:50:0.1)
Mass spectrum (ESI$^+$): m/z=522 [M+H]$^+$ (146) 1-(2-{2-[(ethylcarbonyl)amino]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=508 [M+H]$^+$ (147) 1-[2-(2-acetylamino-phenyl)-2-oxo-ethyl]-3-methyl-7-((E)-2-buten-1-yl)-8-((R)-3-amino-piperidin-1-yl)-xanthine
Mass spectrum (ESI$^+$): m/z=494 [M+H]$^+$ (148) 1-(2-{2-[(methylaminocarbonyl)methoxy]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=524 [M+H]$^+$ (149) 1-[2-(2-acetylamino-phenyl)-2-oxo-ethyl]-3-methyl-7-((E)-2-buten-1-yl)-8-((S)-3-amino-piperidin-1-yl)-xanthine
R$_f$ value: 0.49 (ready-made reversed phase TLC plate (E. Merck), acetonitrile/water/trifluoroacetic acid=50:50:0.1)
Mass spectrum (ESI$^+$): m/z=494 [M+H]$^+$ (150) 1-(2-{2-[(methylaminocarbonyl)methoxy]-phenyl}-2-oxo-ethyl)-3-methyl-7-((E)-2-buten-1-yl)-8-((S)-3-amino-piperidin-1-yl)-xanthine
Mass spectrum (ESI$^+$): m/z=524 [M+H]$^+$ (151) 1-(2-{2-[(isopropylcarbonyl)amino]-phenyl}-2-oxo-ethyl)-3-methyl-7-(2-butyn-1-yl)-8-((R)-3-amino-piperidin-1-yl)-xanthine
Mass spectrum (ESI$^+$): m/z=520 [M+H]$^+$ (152) 1-(2-{2-[(isopropylcarbonyl)amino]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=522 [M+H]$^+$ (153) 1-(2-{2-[2-(morpholin-4-yl)-2-oxo-ethoxy]-phenyl}-2-oxo-ethyl)-3-methyl-7-(2-butyn-1-yl)-8-(3-amino-piperidin-1-yl)-xanthine
Mass spectrum (ESI$^+$): m/z=578 [M+H]$^+$ (154) 1-(2-{2-[(ethylcarbonyl)amino]-phenyl}-2-oxo-ethyl)-3-methyl-7-((E)-2-buten-1-yl)-8-((S)-3-amino-piperidin-1-yl)-xanthine
R$_f$ value: 0.50 (ready-made reversed phase TLC plate (E. Merck), acetonitrile/water/trifluoroacetic acid=50:50:0.1)
Mass spectrum (ESI$^+$): m/z=508 [M+H]$^+$ (155) 1-(2-{2-[(ethylcarbonyl)amino]-phenyl}-2-oxo-ethyl)-3-methyl-7-(2-butyn-1-yl)-8-((R)-3-amino-piperidin-1-yl)-xanthine
Mass spectrum (ESI$^+$): m/z=506 [M+H]$^+$ (156) 1-(2-{2-[(ethylcarbonyl)amino]-phenyl}-2-oxo-ethyl)-3-methyl-7-(2-butyn-1-yl)-8-((S)-3-amino-piperidin-1-yl)-xanthine
R$_f$ value: 0.20 (silica gel, methylene chloride/methanol/conc. aqueous ammonia=90:10:1)
Mass spectrum (ESI$^+$): m/z=506 [M+H]$^+$ (157) 1-[2-(2-acetylamino-phenyl)-2-oxo-ethyl]-3-methyl-7-(2-butyn-1-yl)-8-((R)-3-amino-piperidin-1-yl)-xanthine
Mass spectrum (ESI$^+$): m/z=492 [M+H]$^+$ (158) 1-[2-(2-nitro-3-methoxy-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.49 (silica gel, methylene chloride/methanol/conc. aqueous ammonia=90:10:1)
Mass spectrum (ESI$^+$): m/z=526 [M+H]$^+$ (159) 1-(2-{2-[(phenylcarbonyl)amino]-phenyl}-2-oxo-ethyl)-3-methyl-7-((E)-2-buten-1-yl)-8-(3-amino-piperidin-1-yl)-xanthine
R$_f$ value: 0.49 (ready-made reversed phase TLC plate (E. Merck), acetonitrile/water/trifluoroacetic acid=50:50:0.1)
Mass spectrum (ESI$^+$): m/z=556 [M+H]$^+$ (160) 1-[(2-acetyl-benzofuran-3-yl)methyl]-3-methyl-7-(2-butyn-1-yl)-8-(3-amino-piperidin-1-yl)-xanthine
(Obtained as main product when 1-{2-[2-(2-oxo-propoxy)-phenyl]-2-oxo-ethyl}-3-methyl-7-(2-butyn-1-yl)-8-[3-(tert.-butyloxycarbonylamino)-piperidin-1-yl]-xanthine is treated with trifluoroacetic acid in methylene chloride)
Mass spectrum (ESI$^+$): m/z=489 [M+H]$^+$ (161) 1-{2-[2-(1-ethoxycarbonyl-1-methyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=565 [M+H]$^+$ (162) 1-[2-(2-amino-3-methoxy-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.38 (silica gel, methylene chloride/methanol/conc. aqueous ammonia=90:10:1)
Mass spectrum (ESI$^+$): m/z=496 [M+H]$^+$ (163) 1-[(4-dimethylamino-quinazolin-2-yl)methyl]-3-methyl-7-(2-butyn-1-yl)-8-(3-amino-piperidin-1-yl)-xanthine
R$_f$ value: 0.30 (silica gel, methylene chloride/methanol/conc. aqueous ammonia=90:10:0.1)
Mass spectrum (ESI$^+$): m/z=502 [M+H]$^+$ (164) 1-[2-(2-oxo-2,3-di hydro-benzooxazol-7-yl)-2-oxo-ethyl]-3-methyl-7-(3-methyl-2-buten-1-yl)-8-(3-amino-piperidin-1-yl)-xanthine
R$_f$ value: 0.42 (silica gel, methylene chloride/methanol/conc. aqueous ammonia=90:10:1)
Mass spectrum (ESI$^+$): m/z=508 [M+H]$^+$ (165) 1-(2-{2-[(ethoxycarbonyl)methylamino]-phenyl}-2-oxo-ethyl)-3-methyl-7-((E)-2-buten-1-yl)-8-((R)-3-amino-piperidin-1-yl)-xanthine
R$_f$ value: 0.51 (ready-made reversed phase TLC plate (E. Merck), acetonitrile/water/trifluoroacetic acid=50:50:0.1)
Mass spectrum (ESI$^+$): m/z=538 [M+H]$^+$ (166) 1-(2-phenyl-2-oxo-ethyl)-3-methyl-7-((Z)-2-methyl-2-buten-1-yl)-8-(3-amino-piperidin-1-yl)-xanthine
R$_f$ value: 0.29 (silica gel, methylene chloride/methanol/conc. aqueous ammonia=90:10:1)
Mass spectrum (ESI$^+$): m/z=451 [M+H]$^+$ (167) 1-(2-phenyl-2-oxo-ethyl)-3-methyl-7-((E)-2-methyl-2-buten-1-yl)-8-(3-amino-piperidin-1-yl)-xanthine
R$_f$ value: 0.59 (silica gel, methylene chloride/methanol/conc. aqueous ammonia=80:20:1)
Mass spectrum (ESI$^+$): m/z=451 [M+H]$^+$ (168) 1-[(imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)

$R_f$ value: 0.47 (silica gel, methylene chloride/methanol/conc. aqueous ammonia=90:10:1)

Mass spectrum (ESI$^+$): m/z=447 [M+H]$^+$ (169) 1-[(quinoxalin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=459 [M+H]$^+$ (170) 1-[2-(1,3-dimethyl-2-oxo-2,3-dihydro-1H-benzoimidazol-4-yl)-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.55 (silica gel, methylene chloride/methanol/conc. aqueous ammonia=90:10:1)

Mass spectrum (ESI$^+$): m/z=519 [M+H]$^+$ (171) 1-[(quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

Mass spectrum (ESI$^+$): m/z=459 [M+H]$^+$ (172) 1-[(2-cyano-benzofuran-3-yl)methyl]-3-methyl-7-(2-butyn-1-yl)-8-(3-amino-piperidin-1-yl)-xanthine Mass spectrum (ESI$^+$): m/z=472 [M+H]$^+$ (173) 1-[2-(2-oxo-2,3-di hydro-benzooxazol-4-yl)-2-oxo-ethyl]-3-methyl-7-(2-butyn-1-yl)-8-(3-amino-piperidin-1-yl)-xanthine Mass spectrum (ESI$^+$): m/z=492 [M+H]$^+$ $R_f$ value: 0.47 (silica gel, methylene chloride/methanol/conc. aqueous ammonia=90:10:1)

(174) 1-[(3-methyl-quinoxalin-2-yl)methyl]-3-methyl-7-(2-butyn-1-yl)-8-(3-amino-piperidin-1-yl)-xanthine Melting point: 188.5-191° C.

Mass spectrum (ESI$^+$): m/z=473 [M+H]$^+$ (175) 1-[(3-phenyl-isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.45 (ready-made reversed phase TLC plate (E. Merck), acetonitrile/water/trifluoroacetic acid=50:50:1)

Mass spectrum (ESI$^+$): m/z=534 [M+H]$^+$ (176) 1-(2-{2-[(methanesulphinyl)methoxy]-phenyl}-2-oxo-ethyl)-3-methyl-7-(2-butyn-1-yl)-8-(3-amino-piperidin-1-yl)-xanthine x trifluoroacetic acid Mass spectrum (ESI$^+$): m/z=527 [M+H]$^+$ (177) 1-[(benzofuran-3-yl)methyl]-3-methyl-7-(2-butyn-1-yl)-8-(3-amino-piperidin-1-yl)-xanthine (Produced when 1-{[2-(tert.-butylcarbonyl)-benzofuran-3-yl]methyl}-3-methyl-7-(2-butyn-1-yl)-8-[3-(tert.-butyloxycarbonylamino)-piperidin-1-yl]-xanthine is treated with trifluoroacetic acid in methylene chloride)

Mass spectrum (ESI$^+$): m/z=447 [M+H]$^+$ (178) 1-[(3,4-dimethyl-isoquinolin-1-yl)methyl]-3-methyl-7-(2-butyn-1-yl)-8-(3-amino-piperidin-1-yl)-xanthine-hydrochloride (Carried out with 5-6 M isopropanolic hydrochloric acid in methylene chloride)

$R_f$ value: 0.75 (aluminium oxide, methylene chloride/methanol=10:1)

Mass spectrum (ESI$^+$): m/z=486 [M+H]$^+$ (179) 1-[(benzofuran-2-yl)methyl]-3-methyl-7-(2-butyn-1-yl)-8-((R)-3-amino-piperidin-1-yl)-xanthine Mass spectrum (ESI$^+$): m/z=447 [M+H]$^+$ (180) 1-{[4-(morphol in-4-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.45 (silica gel, methylene chloride/methanol/conc. aqueous ammonia=90:10:0.1)

Mass spectrum (ESI$^+$): m/z=544 [M+H]$^+$ (181) 1-{[4-(piperidin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.55 (silica gel, methylene chloride/methanol/conc. aqueous ammonia=90:10:0.1)

Mass spectrum (ESI$^+$): m/z=542 [M+H]$^+$ (182) 1-{[4-(piperazin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.23 (silica gel, methylene chloride/methanol/conc. aqueous ammonia=90:10:0.1)

Mass spectrum (ESI$^+$): m/z=543 [M+H]$^+$ (183) 1-{[4-(pyrrolidin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:0.1)

Mass spectrum (ESI$^+$): m/z=528 [M+H]$^+$ (184) 1-[2-(3-methyl-2-oxo-2,3-dihydro-1H-benzoimidazol-4-yl)-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.43 (silica gel, methylene chloride/methanol/conc. aqueous ammonia=90:10:1)

Mass spectrum (ESI$^+$): m/z=505 [M+H]$^+$ (185) 1-[(4-cyano-naphthalen-1-yl)methyl]-3-methyl-7-(2-butyn-1-yl)-8-((R)-3-amino-piperidin-1-yl)-xanthine $R_f$ value: 0.27 (silica gel, methylene chloride/methanol/conc. aqueous ammonia=90:10:1)

Mass spectrum (ESI$^+$): m/z=482 [M+H]$^+$ (186) 1-[(imidazo[1,2-a]pyridine-3-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.37 (silica gel, methylene chloride/methanol/conc. aqueous ammonia=90:10:1)

Mass spectrum (ESI$^+$): m/z=447 [M+H]$^+$ (187) 1-[(8-methyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.46 (silica gel, methylene chloride/methanol/conc. aqueous ammonia=90:10:1)

Mass spectrum (ESI$^+$): m/z=461 [M+H]$^+$ (188) 1-[(4-amino-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.40 (silica gel, methylene chloride/methanol/conc. aqueous ammonia=90:10:0.1)

Mass spectrum (ESI$^+$): m/z=474 [M+H]$^+$ (189) 1-(2-phenyl-2-oxo-ethyl)-3-methyl-7-((Z)-2-buten-1-yl)-8-(3-amino-piperidin-1-yl)-xanthine
Mass spectrum (ESI⁺): m/z=437 [M+H]⁺

(190) 1-[(8-methoxy-quinolin-5-yl)methyl]-3-methyl-7-(2-butyn-1-yl)-8-(3-amino-piperidin-1-yl)-xanthine x 2 trifluoroacetic acid
$R_f$-value: 0.45 (silica gel, methylene chloride/methanol=5:1)
Mass spectrum (ESI⁺): m/z=488 [M+H]⁺

(191) 1-[(5-methoxy-quinolin-8-yl)methyl]-3-methyl-7-(2-butyn-1-yl)-8-(3-amino-piperidin-1-yl)-xanthine x trifluoroacetic acid
$R_f$-value: 0.20 (silica gel, ethyl acetate/methanol=1:1)
Mass spectrum (ESI⁺): m/z=488 [M+H]⁺

(192) 1-[(4-phenyl-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.60 (silica gel, methylene chloride/methanol/conc. aqueous ammonia=90:10:1)
Mass spectrum (ESI⁺): m/z=535 [M+H]⁺

(193) 1-[(7-methyl-imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.48 (silica gel, methylene chloride/methanol/conc. aqueous ammonia=90:10:1)
Mass spectrum (ESI⁺): m/z=461 [M+H]⁺

(194) 1-[(2-cyclopropyl-quinazolin-4-yl)methyl]-3-methyl-7-[(1-cyclopenten-1-yl)methyl]-8-(3-amino-piperidin-1-yl)-xanthine
(Carried out with 5-6 M isopropanolic hydrochloric acid in methylene chloride)
$R_f$-value: 0.55 (ready-made reversed phase TLC plate (E. Merck), acetonitrile/water/trifluoroacetic acid=50:50:1)
Mass spectrum (ESI⁺): m/z=527 [M+H]⁺

(195) 1-(2-oxo-4-phenyl-butyl)-3-methyl-7-(2-butyn-1-yl)-8-((R)-3-amino-piperidin-1-yl)-xanthine x trifluoroacetic acid
Mass spectrum (ESI⁺): m/z=463 [M+H]⁺

(196) 1-(2-{2-[(methylaminocarbonyl)methylamino]-phenyl}-2-oxo-ethyl)-3-methyl-7-((E)-2-buten-1-yl)-8-((R)-3-amino-piperidin-1-yl)-xanthine
$R_f$-value: 0.52 (ready-made reversed phase TLC plate (E. Merck), acetonitrile/water/trifluoroacetic acid=50:50:0.1)
Mass spectrum (ESI⁺): m/z=523 [M+H]⁺

(197) 1-[2-(2-oxo-2,3-dihydro-1H-benzoimidazol-4-yl)-2-oxo-ethyl]-3-methyl-7-(2-butyn-1-yl)-8-(3-amino-piperidin-1-yl)-xanthine
$R_f$-value: 0.40 (silica gel, methylene chloride/methanol/conc. aqueous ammonia=90:10:1)
Mass spectrum (ESI⁺): m/z=491 [M+H]⁺

(198) 1-[(3-difluoromethyl-isoquinolin-1-yl)methyl]-3-methyl-7-(2-butyn-1-yl)-8-(3-amino-piperidin-1-yl)-xanthine x trifluoroacetic acid
$R_f$ value: 0.75 (silica gel, methylene chloride/methanol=10:1)
Mass spectrum (ESI⁺): m/z=508 [M+H]⁺

(199) 1-[2-(2,2-difluoro-benzo[1,3]dioxol-4-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$-value: 0.80 (silica gel, methylene chloride/methanol/conc. aqueous ammonia=96:4:0.5)
Mass spectrum (ESI⁺): m/z=515 [M+H]⁺

(200) 1-[(3-methyl-imidazo[1,2-a]pyridin-2-yl)methyl]-3-methyl-7-(2-butyn-1-yl)-8-(3-amino-piperidin-1-yl)-xanthine
$R_f$-Wet: 0.45 (silica gel, methylene chloride/methanol/conc. aqueous ammonia=90:10:1)
Mass spectrum (ESI⁺): m/z=461 [M+H]⁺

(201) 1-[2-(2,2-difluoro-benzo[1,3]dioxol-4-yl)-2-oxo-ethyl]-3-methyl-7-(2-butyn-1-yl)-8-((S)-3-amino-piperidin-1-yl)-xanthine
(Carried out with 5-6 M isopropanolic hydrochloric acid in methylene chloride)
Mass spectrum (ESI⁺): m/z=515 [M+H]⁺

(202) 1-[(5-methyl-imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.53 (silica gel, methylene chloride/methanol/conc. aqueous ammonia=90:10:1)
Mass spectrum (ESI⁺): m/z=461 [M+H]⁺

(203) 1-[(6-methyl-imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Melting point: 176.5-178° C.
Mass spectrum (ESI⁺): m/z=461 [M+H]⁺

(204) 1-[(3-benzyl-imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Melting point: 201-204° C.
Mass spectrum (ESI⁺): m/z=537 [M+H]⁺

(205) 1-[(4-isopropyl-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.50 (silica gel, methylene chloride/methanol/conc. aqueous ammonia=90:10:0.1)
Mass spectrum (ESI⁺): m/z=501 [M+H]⁺

(206) 1-[(2,3-dihydro-benzo[1,4]dioxin-6-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.65 (silica gel, methylene chloride/methanol/conc. aqueous ammonia=90:10:1)
Mass spectrum (ESI⁺): m/z=465 [M+H]⁺

(207) 1-[(1-methyl-1H-indol-2-yl)methyl]-3-methyl-7-(2-butyn-1-yl)-8-(3-amino-piperidin-1-yl)-xanthine-hydrochloride
(Carried out with 5-6 M isopropanolic hydrochloric acid in methylene chloride)
$R_f$ value: 0.60 (silica gel, methylene chloride/methanol/conc. aqueous ammonia=90:10:1)
Mass spectrum (ESI⁺): m/z=460 [M+H]⁺

(208) 1-[(quinolin-3-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.50 (silica gel, methylene chloride/methanol/conc. aqueous ammonia=90:10:0.1)
Mass spectrum (ESI⁺): m/z=458 [M+H]⁺

(209) 1-[(3-phenyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=523 [M+H]$^+$ (210) 1-[(1H-indol-2-yl)methyl]-3-methyl-7-(2-butyn-1-yl)-8-(3-amino-piperidin-1-yl)-xanthine-hydrochloride $R_f$ value: 0.55 (silica gel, methylene chloride/methanol/conc. aqueous ammonia=90:10:1)

Mass spectrum (ESI$^+$): m/z=446 [M+H]$^+$ (211) 1-[2-(naphthalen-1-yl)-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.60 (silica gel, methylene chloride/methanol/conc. aqueous ammonia=90:10:1)

Mass spectrum (ESI$^+$): m/z=485 [M+H]$^+$ (212) 1-[(5-methoxy-isoquinolin-8-yl)methyl]-3-methyl-7-(2-butyn-1-yl)-8-(3-amino-piperidin-1-yl)-xanthine x trifluoroacetic acid $R_f$ value: 0.50 (silica gel, methylene chloride/methanol=5:1)

Mass spectrum (ESI$^+$): m/z=488 [M+H]$^+$ (213) 1-{[1-(1-cyano-1-methyl-ethyl)-isoquinolin-3-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.25 (ready-made reversed phase TLC plate (E. Merck), acetonitrile/water/trifluoroacetic acid=50:50:1)

Mass spectrum (ESI$^+$): m/z=525 [M+H]$^+$ (214) 1-(2-cyanoimino-2-phenyl-ethyl)-3-methyl-7-(2-butyn-1-yl)-8-(3-amino-piperidin-1-yl)-xanthine x trifluoroacetic acid (E/Z-mixture)

Mass spectrum (ESI$^+$): m/z=459 [M+H]$^+$ (215) 1-[(1H-benzoimidazol-2-yl)methyl]-3-methyl-7-(2-butyn-1-yl)-8-(3-amino-piperidin-1-yl)-xanthine x trifluoroacetic acid Mass spectrum (ESI$^+$): m/z=447 [M+H]$^+$ (216) 1-[(1-methyl-1H-benzoimidazol-2-yl)methyl]-3-methyl-7-(2-butyn-1-yl)-8-(3-amino-piperidin-1-yl)-xanthine Mass spectrum (ESI$^+$): m/z=461 [M+H]$^+$ (217) 1-[(4-phenyl-quinazolin-2-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

Mass spectrum (ESI$^+$): m/z=535 [M+H]$^+$ (218) 1-[(2,3-dimethyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:0.1)

Mass spectrum (ESI$^+$): m/z=487 [M+H]$^+$ (219) 1-[(2-methyl-1H-benzoimidazol-5-yl)methyl]-3-methyl-7-(2-butyn-1-yl)-8-(3-amino-piperidin-1-yl)-xanthine $R_f$ value: 0.35 (silica gel, methylene chloride/methanol/conc. aqueous ammonia=90:10:0.1)

Mass spectrum (ESI$^+$): m/z=461 [M+H]$^+$ (220) 1-[(4-phenyl-quinazolin-2-yl)methyl]-3-methyl-7-(2-butyn-1-yl)-8-((S)-3-amino-piperidin-1-yl)-xanthine (Carried out with 5-6 M isopropanolic hydrochloric acid in methylene chloride)

Mass spectrum (ESI$^+$): m/z=535 [M+H]$^+$ (221) 1-[2-(quinolin-8-yl-]-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.48 (silica gel, methylene chloride/methanol/conc. aqueous ammonia=90:10:1)

Mass spectrum (ESI$^+$): m/z=486 [M+H]$^+$ (222) 1-[(3,4-dimethyl-6,7-dihydro-5H-[2]pyridin-1-yl)methyl]-3-methyl-7-(2-butyn-1-yl)-8-(3-amino-piperidin-1-yl)-xanthine x trifluoroacetic acid $R_f$ value: 0.25 (aluminium oxide, methylene chloride/methanol=20:1)

Mass spectrum (ESI$^+$): m/z=476 [M+H]$^+$ (223) 1-[(3,4-dimethyl-5,6,7,8-tetrahydro-isoquinolin-1-yl)methyl]-3-methyl-7-(2-butyn-1-yl)-8-(3-amino-piperidin-1-yl)-xanthine x trifluoroacetic acid $R_f$ value: 0.50 (aluminium oxide, methylene chloride/methanol=20:1)

Mass spectrum (ESI$^+$): m/z=490 [M+H]$^+$ (224) 1-[2-(1H-indol-4-yl)-2-oxo-ethyl]-3-methyl-7-(2-butyn-1-yl)-8-(3-amino-piperidin-1-yl)-xanthine $R_f$ value: 0.52 (silica gel, methylene chloride/methanol/conc. aqueous ammonia=90:10:1)

Mass spectrum (ESI$^+$): m/z=474 [M+H]$^+$ (225) 1-[(1H-benzoimidazol-5-yl)methyl]-3-methyl-7-(2-butyn-1-yl)-8-(3-amino-piperidin-1-yl)-xanthine $R_f$ value: 0.50 (silica gel, methylene chloride/methanol/conc. aqueous ammonia=90:10:1)

Mass spectrum (ESI$^+$): m/z=447 [M+H]$^+$ (226) 1-[(pyrazolo[1,5-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.47 (silica gel, methylene chloride/methanol/conc. aqueous ammonia=90:10:1)

Mass spectrum (ESI$^+$): m/z=447 [M+H]$^+$ (227) 1-[(1-methyl-2-oxo-1,2-dihydro-quinolin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.40 (silica gel, methylene chloride/methanol/conc. aqueous ammonia=90:10:1)

Mass spectrum (ESI$^+$): m/z=488 [M+H]$^+$ (228) 1-[(2-oxo-1,2-dihydro-quinolin-6-yl)methyl]-3-methyl-7-(2-butyn-1-yl)-8-(3-amino-piperidin-1-yl)-xanthine $R_f$ value: 0.23 (silica gel, methylene chloride/methanol/conc. aqueous ammonia=90:10:1)

Mass spectrum (ESI$^+$): m/z=474 [M+H]$^+$ (229) 1-[(2,3,8-trimethyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.37 (silica gel, methylene chloride/methanol/conc. aqueous ammonia=90:10:1)

Mass spectrum (ESI$^+$): m/z=501 [M+H]$^+$ (230) 1-[(8-methyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.35 (silica gel, methylene chloride/methanol/conc. aqueous ammonia=90:10:1)

Mass spectrum (ESI$^+$): m/z=473 [M+H]$^+$ (231) 1-[(4-methyl-phthalazin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.55 (ready-made reversed phase TLC plate (E. Merck), acetonitrile/water/trifluoroacetic acid=50:50:1)

Mass spectrum (ESI$^+$): m/z=473 [M+H]$^+$ (232) 1-[(4-bromo-3-methoxy-isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.40 (ready-made reversed phase TLC plate (E. Merck), acetonitrile/water/trifluoroacetic acid=50:50:1)

Mass spectrum (ESI$^+$): m/z=566, 568 [M+H]$^+$ (233) 1-(2-phenyl-2-oxo-ethyl)-3-methyl-7-((E)-1-buten-1-yl)-8-(3-amino-piperidin-1-yl)-xanthine R$_f$ value: 0.31 (silica gel, methylene chloride/methanol/conc. aqueous ammonia=90:10:1)

Mass spectrum (ESI$^+$): m/z=437 [M+H]$^+$ (234) 1-[(4-difluoromethoxy-naphthalen-1-yl)methyl]-3-methyl-7-(2-butyn-1-yl)-8-((R)-3-amino-piperidin-1-yl)-xanthine R$_f$ value: 0.08 (silica gel, methylene chloride/methanol/conc. aqueous ammonia=95:5:1)

Mass spectrum (ESI$^+$): m/z=523 [M+H]$^+$ (235) 1-[2-(1H-indol-7-yl)-2-oxo-ethyl]-3-methyl-7-(2-butyn-1-yl)-8-(3-amino-piperidin-1-yl)-xanthine x trifluoroacetic acid R$_f$ value: 0.46 (silica gel, methylene chloride/methanol/conc. aqueous ammonia=90:10:1)

Mass spectrum (ESI$^+$): m/z=474 [M+H]$^+$ (236) 1-[(E)-3-(2-nitro-phenyl)-2-propen-1-yl]-3-methyl-7-(2-butyn-1-yl)-8-(3-amino-piperidin-1-yl)-xanthine Mass spectrum (ESI$^+$): m/z=478 [M+H]$^+$ (237) 1-((E)-3-pentafluorophenyl-2-propen-1-yl)-3-methyl-7-(2-butyn-1-yl)-8-(3-amino-piperidin-1-yl)-xanthine Mass spectrum (ESI$^+$): m/z=523 [M+H]$^+$ (238) 1-[(4-nitro-naphthalen-1-yl)methyl]-3-methyl-7-(2-butyn-1-yl)-8-((R)-3-amino-piperidin-1-yl)-xanthine R$_f$ value: 0.38 (silica gel, methylene chloride/methanol/conc. aqueous ammonia=90:10:1)

Mass spectrum (ESI$^+$): m/z=502 [M+H]$^+$ (239) 1-{[1-(2-cyano-ethyl)-1H-benzoimidazol-2-yl]methyl}-3-methyl-7-(2-butyn-1-yl)-8-(3-amino-piperidin-1-yl)-xanthine-hydrochloride (Carried out with 5-6 M isopropanolic hydrochloric acid in methylene chloride)

R$_f$ value: 0.55 (ready-made reversed phase TLC plate (E. Merck), acetonitrile/water/trifluoroacetic acid=50:50:0.1)

Mass spectrum (ESI$^+$): m/z=500 [M+H]$^+$ (240) 1-({1-[(methylaminocarbonyl)methyl]-1H-benzoimidazol-2-yl}methyl)-3-methyl-7-(2-butyn-1-yl)-8-(3-amino-piperidin-1-yl)-xanthine x trifluoroacetic acid Mass spectrum (ESI$^+$): m/z=518 [M+H]$^+$ (241) 1-[(1-benzyl-1H-benzoimidazol-2-yl)methyl]-3-methyl-7-(2-butyn-1-yl)-8-(3-amino-piperidin-1-yl)-xanthine R$_f$ value: 0.47 (ready-made reversed phase TLC plate (E. Merck), acetonitrile/water/trifluoroacetic acid=50:50:0.1)

Mass spectrum (ESI$^+$): m/z=537 [M+H]$^+$ (242) 1-[(benzooxazol-2-y)methyl]-3-methyl-7-(2-butyn-1-yl)-8-(3-amino-piperidin-1-yl)-xanthine x trifluoroacetic acid R$_f$ value: 0.50 (ready-made reversed phase TLC plate (E. Merck), acetonitrile/water/trifluoroacetic acid=50:50:0.1)

Mass spectrum (ESI$^+$): m/z=448 [M+H]$^+$ (243) 1-[(5-nitro-benzooxazol-2-y)methyl]-3-methyl-7-(2-butyn-1-yl)-8-(3-amino-piperidin-1-yl)-xanthine R$_f$ value: 0.49 (ready-made reversed phase TLC plate (E. Merck), acetonitrile/water/trifluoroacetic acid=50:50:0.1)

Mass spectrum (ESI$^+$): m/z=493 [M+H]$^+$ (244) 1-[(3-methyl-isoquinolin-1-yl)methyl]-3-methyl-7-(3-methyl-1-buten-1-yl)-8-((R)-3-amino-piperidin-1-yl)-xanthine R$_f$ value: 0.21 (silica gel, methylene chloride/methanol/conc. aqueous ammonia=90:10:1)

Mass spectrum (ESI$^+$): m/z=488 [M+H]$^+$ (245) 1-[(quinolin-7-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.55 (silica gel, methylene chloride/methanol/conc. aqueous ammonia=90:10:1)

Mass spectrum (ESI$^+$): m/z=458 [M+H]$^+$ (246) 1-[([1,5]naphthyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.51 (silica gel, methylene chloride/methanol/conc. aqueous ammonia=90:10:1)

Mass spectrum (ESI$^+$): m/z=459 [M+H]$^+$ (247) 1-[(8-methyl-quinoxalin-6-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

R$_f$ value: 0.49 (silica gel, methylene chloride/methanol/conc. aqueous ammonia=90:10:1)

Mass spectrum (ESI$^+$): m/z=473 [M+H]$^+$ (248) 1-[(2,3,8-trimethyl-quinoxalin-6-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

R$_f$ value: 0.46 (silica gel, methylene chloride/methanol/conc. aqueous ammonia=90:10:1)

Mass spectrum (ESI$^+$): m/z=501 [M+H]$^+$ (249) 1-[([1,6]naphthyridin-5-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.50 (silica gel, methylene chloride/methanol/conc. aqueous ammonia=90:10:1)

Mass spectrum (ESI$^+$): m/z=459 [M+H]$^+$ (250) 1-[([1,8]naphthyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.45 (silica gel, methylene chloride/methanol/conc. aqueous ammonia=90:10:1)

Mass spectrum (ESI$^+$): m/z=459 [M+H]$^+$ (251) 1-[(4-fluoro-naphthalen-1-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

R$_f$ value: 0.50 (silica gel, methylene chloride/methanol/conc. aqueous ammonia=90:10:1)

Mass spectrum (ESI$^+$): m/z=475 [M+H]$^+$ (252) 1-[([1,5]naphthyridin-2-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
Mass spectrum (ESI+): m/z=459 [M+H]+

(253) 1-[2-(3-methyl-2-oxo-2,3-dihydro-benzooxazol-4-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
Melting point: 187-189° C.
Mass spectrum (ESI+): m/z=506 [M+H]+

(254) 1-[(8-phenyl-quinoxalin-6-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.50 (silica gel, methylene chloride/methanol/conc. aqueous ammonia=90:10:1)
Mass spectrum (ESI+): m/z=535 [M+H]+

(255) 1-[([1,5]naphthyridine-4-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI+): m/z=459 [M+H]+

(256) 1-((E)-3-pentafluorophenyl-allyl)-3-methyl-7-(2-butyn-1-yl)-8-((R)-3-amino-piperidin-1-yl)-xanthine
Mass spectrum (ESI+): m/z=523 [M+H]+

(257) 1-[(E)-3-(2-trifluoromethyl-phenyl)-allyl]-3-methyl-7-(2-butyn-1-yl)-8-((R)-3-amino-piperidin-1-yl)-xanthine
Mass spectrum (ESI+): m/z=501 [M+H]+

(258) 1-[(E)-3-(3-trifluoromethyl-phenyl)-allyl]-3-methyl-7-(2-butyn-1-yl)-8-((R)-3-amino-piperidin-1-yl)-xanthine
Mass spectrum (ESI+): m/z=501 [M+H]+

(259) 1-[(E)-3-(4-trifluoromethyl-phenyl)-allyl]-3-methyl-7-(2-butyn-1-yl)-8-((R)-3-amino-piperidin-1-yl)-xanthine
Mass spectrum (ESI+): m/z=501 [M+H]+

(260) 1-[(3-trifluoromethyl-isoquinolin-1-yl)methyl]-3-methyl-7-(2-butyn-1-yl)-8-((R)-3-amino-piperidin-1-yl)-xanthine x trifluoroacetic acid
Mass spectrum (ESI+): m/z=526 [M+H]+

(261) 1-[(3-methyl-isoquinolin-1-yl)methyl]-3-isopropyl-7-(2-butyn-1-yl)-8-((R)-3-amino-piperidin-1-yl)-xanthine (262) 1-[(3-methyl-isoquinolin-1-yl)methyl]-3-(4-fluorophenyl)-7-(2-butyn-1-yl)-8-((R)-3-amino-piperidin-1-yl)-xanthine (263) 1-[(3-methyl-isoquinolin-1-yl)methyl]-3-methyl-7-(2-cyano-benzyl)-8-(3-amino-piperidin-1-yl)-xanthine
(Carried out with 5-6 M isopropanolic hydrochloric acid in methylene chloride)
$R_f$ value: 0.51 (ready-made reversed phase TLC plate (E. Merck), acetonitrile/water/trifluoroacetic acid=50:50:1)
Mass spectrum (ESI+): m/z=535 [M+H]+

(264) 1-[(3-difluoromethyl-isoquinolin-1-yl)methyl]-3-methyl-7-(2-butyn-1-yl)-8-((R)-3-amino-piperidin-1-yl)-xanthine
Mass spectrum (ESI+): m/z=508 [M+H]+

(265) 1-[(4-chloro-3-methoxy-isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Mass spectrum (ESI+): m/z=522, 524 [M+H]+

$R_f$ value: 0.40 (ready-made reversed phase TLC plate (E. Merck), acetonitrile/water/trifluoroacetic acid=50:50:1)

(266) 1-[(4-ethoxy-quinazolin-2-yl)methyl]-3-methyl-7-(2-butyn-1-yl)-8-(3-amino-piperidin-1-yl)-xanthine
(Carried out with 1 M ethereal hydrochloric acid)
$R_f$ value: 0.60 (ready-made reversed phase TLC plate (E. Merck), acetonitrile/water/trifluoroacetic acid=50:50:1)
Mass spectrum (ESI+): m/z=503 [M+H]+

(267) 1-[(4-isopropyloxy-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.55 (ready-made reversed phase TLC plate (E. Merck), acetonitrile/water/trifluoroacetic acid=50:50:1)
Mass spectrum (ESI+): m/z=517 [M+H]+

(268) 1-[(2-methyl-benzothiazol-6-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Melting point: 167° C.
Mass spectrum (ESI+): m/z=478 [M+H]+

(269) 1-[(3-phenyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI+): m/z=534 [M+H]+

(270) 1-[(4-phenyloxy-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.60 (ready-made reversed phase TLC plate (E. Merck), acetonitrile/water/trifluoroacetic acid=50:50:1)
Mass spectrum (ESI+): m/z=551 [M+H]+

(271) 1-[(4-phenyl-quinazolin-2-yl)methyl]-3-cyclopropyl-7-(2-butyn-1-yl)-8-(3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI+): m/z=561 [M+H]+

(272) 1-[(3-methyl-isoquinolin-1-yl)methyl]-3-cyclopropyl-7-(2-butyn-1-yl)-8-(3-amino-piperidin-1-yl)-xanthine
(Carried out with 5-6 M isopropanolic hydrochloric acid in methylene chloride)
$R_f$ value: 0.55 (ready-made reversed phase TLC plate (E. Merck), acetonitrile/water/trifluoroacetic acid=50:50:1)
Mass spectrum (ESI+): m/z=498 [M+H]+

(273) 1-[(2-phenyl-quinazolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.50 (ready-made reversed phase TLC plate (E. Merck), acetonitrile/water/trifluoroacetic acid=50:50:1)
Mass spectrum (ESI+): m/z=535 [M+H]+

(274) 1-[2-(2-methoxy-phenyl)-2-oxo-ethyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.29 (silica gel, methylene chloride/methanol/conc. aqueous ammonia=90:10:1)
Mass spectrum (ESI+): m/z=465 [M+H]+

(275) 1-[2-(3-methoxy-phenyl)-2-oxo-ethyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.27 (silica gel, methylene chloride/methanol/conc. aqueous ammonia=90:10:1)
Mass spectrum (ESI$^+$): m/z=465 [M+H]$^+$ (276) 1-[2-(3-trifluoromethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.29 (silica gel, methylene chloride/methanol/conc. aqueous ammonia=90:10:1)
Mass spectrum (ESI$^+$): m/z=519 [M+H]$^+$ (277) 1-[2-(biphenyl-2-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.35 (ready-made reversed phase TLC plate (E. Merck), acetonitrile/water/trifluoroacetic acid=50:50:1)
Mass spectrum (ESI$^+$): m/z=511 [M+H]$^+$ (278) 1-[2-(biphenyl-3-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.35 (ready-made reversed phase TLC plate (E. Merck), acetonitrile/water/trifluoroacetic acid=50:50:1)
Mass spectrum (ESI$^+$): m/z=511 [M+H]$^+$ (279) 1-[2-(3-isopropyloxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=90:10:1)
Mass spectrum (ESI$^+$): m/z=493 [M+H]$^+$ (280) 1-[(3-methyl-isoquinolin-1-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.50 (ready-made reversed phase TLC plate (E. Merck), acetonitrile/water/trifluoroacetic acid=50:50:1)
Mass spectrum (ESI$^+$): m/z=498 [M+H]$^+$ (281) 1-[(4-phenyl-quinazolin-2-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI$^+$): m/z=561 [M+H]$^+$ (282) 1-[(4-cyano-naphthalen-1-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
Melting point: 191° C.
Mass spectrum (ESI$^+$): m/z=508 [M+H]$^+$ (283) 1-[2-(2-phenyloxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.40 (ready-made reversed phase TLC plate (E. Merck), acetonitrile/water/trifluoroacetic acid=50:50:1)
Mass spectrum (ESI$^+$): m/z=527 [M+H]$^+$ (284) 1-[2-(3-ethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.29 (silica gel, methylene chloride/methanol/conc. aqueous ammonia=90:10:1)
Mass spectrum (ESI$^+$): m/z=479 [M+H]$^+$ (285) 1-[2-(3-methoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.28 (silica gel, methylene chloride/methanol/conc. aqueous ammonia=90:10:1)
Mass spectrum (ESI$^+$): m/z=465 [M+H]$^+$ (286) 1-[2-(2-methoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.34 (silica gel, methylene chloride/methanol/conc. aqueous ammonia=90:10:1)
Mass spectrum (ESI$^+$): m/z=465 [M+H]$^+$ (287) 1-[(3-methyl-isoquinolin-1-yl)methyl]-3-methyl-7-(2-chloro-benzyl)-8-((R)-3-amino-piperidin-1-yl)-xanthine
Mass spectrum (ESI$^+$): m/z=544, 546 [M+H]$^+$ (288) 1-[(3-methyl-isoquinolin-1-yl)methyl]-3-methyl-7-(2-bromo-benzyl)-8-((R)-3-amino-piperidin-1-yl)-xanthine
Mass spectrum (ESI$^+$): m/z=588, 590 [M+H]$^+$ (289) 1-[(1,2,3,4-tetrahydro-phenanthridin-6-yl)methyl]-3-methyl-7-(2-butyn-1-yl)-8-(3-amino-piperidin-1-yl)-xanthine x trifluoroacetic acid
$R_f$ value: 0.75 (aluminium oxide, methylene chloride/methanol=10:1)
Mass spectrum (ESI$^+$): m/z=512 [M+H]$^+$ (290) 1-[2-(3-difluoromethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.28 (silica gel, methylene chloride/methanol/conc. aqueous ammonia=90:10:1)
Mass spectrum (ESI$^+$): m/z=501 [M+H]$^+$ (291) 1-[(3-methyl-isoquinolin-1-yl)methyl]-3-methyl-7-(2-ethynyl-benzyl)-8-((R)-3-amino-piperidin-1-yl)-xanthine (292) 1-[(3-methyl-isoquinolin-1-yl)methyl]-3-phenyl-7-(2-butyn-1-yl)-8-((R)-3-amino-piperidin-1-yl)-xanthine (293) 1-[(phenanthren-9-yl)methyl]-3-methyl-7-(2-butyn-1-yl)-8-((R)-3-amino-piperidin-1-yl)-xanthine (294) 1-[(4-methyl-quinazolin-2-yl)methyl]-3-methyl-7-(2-chloro-benzyl)-8-((R)-3-amino-piperidin-1-yl)-xanthine
$R_f$ value: 0.35 (silica gel, methylene chloride/methanol/triethylamine=90:10:1)
Mass spectrum (ESI$^+$): m/z=545, 547 [M+H]$^+$ (295) 1-[(4-phenyl-quinazolin-2-yl)methyl]-3-methyl-7-(2-chloro-benzyl)-8-((R)-3-amino-piperidin-1-yl)-xanthine
$R_f$ value: 0.40 (silica gel, methylene chloride/methanol/triethylamine=90:10:1)
Mass spectrum (ESI$^+$): m/z=607, 609 [M+H]$^+$

EXAMPLE 3

1-[2-(3-carboxymethoxy-phenyl)-2-oxo-ethyl]-3-methyl-7-(3-methyl-2-buten-1-yl)-8-(3-amino-piperidin-1-yl)-xanthine Prepared by saponifying 70 mg of 1-(2-{3-[(methoxycarbonyl)methoxy]-phenyl}-2-oxo-ethyl)-3-methyl-7-(3-methyl-2-buten-1-yl)-8-(3-amino-piperidin-1-yl)-xanthine with 0.10 ml of 4 M potassium hydroxide solution in a mixture of 1 ml of tetrahydrofuran and 0.5 ml of methanol at ambient temperature.

Yield: 57 mg (84% of theory)

$R_f$ value: 0.55 (ready-made reversed phase TLC plate (E. Merck), acetonitrile/water/trifluoroacetic acid=50:50:0.1)

Mass spectrum (ESI$^+$): m/z=525 [M+H]$^+$

The following compounds are obtained analogously to Example 3:

(1)  1-[2-(2-carboxymethoxy-phenyl)-2-oxo-ethyl]-3-methyl-7-(3-methyl-2-buten-1-yl)-8-(3-amino-piperidin-1-yl)-xanthine (Carried out with sodium hydroxide solution)

Mass spectrum (ESI$^-$): m/z=523 [M-H]

EXAMPLE 4

Coated tablets containing 75 mg of active substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 5

Tablets containing 100 mg of active substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 6

Tablets containing 150 mg of active substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

EXAMPLE 7

Hard gelatine capsules containing 150 mg of active substance 1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 8

Suppositories containing 150 mg of active substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 9

Suspension containing 50 mg of active substance

| 100 ml of suspension contain: | | |
| --- | --- | --- |
| active substance | | 1.00 g |
| carboxymethylcellulose-Na-salt | | 0.10 g |
| methyl p-hydroxybenzoate | | 0.05 g |
| propyl p-hydroxybenzoate | | 0.01 g |
| glucose | | 10.00 g |
| glycerol | | 5.00 g |
| 70% sorbitol solution | | 20.00 g |
| flavouring | | 0.30 g |
| dist. water | ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 10

Ampoules containing 10 mg active substance

| Composition: | | |
| --- | --- | --- |
| active substance | | 10.0 mg |
| 0.01 N hydrochloric acid q.s. | | |
| double-distilled water | ad | 2.0 ml |

Preparation:

The active substance is dissolved in the necessary amount of 0.01 N HCl, made isotonic with common salt, filtered sterile and transferred into 2 ml ampoules.

EXAMPLE 11

Ampoules containing 50 mg of active substance

| Composition: | | |
| --- | --- | --- |
| active substance | | 50.0 mg |
| 0.01 N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

The invention claimed is:

1. A compound chosen from:

(1) 1-[(quinazolin-2-yl)methyl]-3-methyl-7-(2-butyn-1-yl)-8-((R)-3-amino-piperidin-1-yl)-xanthine, (2) 1-(2-{2-[(ethylaminocarbonyl)methoxy]-phenyl}-2-oxo-ethyl)-3-methyl-7-(2-butyn-1-yl)-8-((R)-3-amino-piperidin-1-yl)-xanthine, (3) 1-(2-{2-[(methylaminocarbonyl)methoxy]-phenyl}-2-oxo-ethyl)-3-methyl-7-(2-butyn-1-yl)-8-((R)-3-amino-piperidin-1-yl)-xanthine, (4) 1-(2-phenyl-2-oxo-ethyl)-3-methyl-7-((E)-2-buten-1-yl)-8-((R)-3-amino-piperidin-1-yl)-xanthine, (5) 1-[(3-methyl-isoquinolin-1-yl)methyl]-3-methyl-7-(2-butyn-1-yl)-8-((S)-3-amino-piperidin-1-yl)-xanthine, (6) 1-[(3-methyl-isoquinolin-1-yl)methyl]-3-methyl-7-(2-butyn-1-yl)-8-((R)-3-amino-piperidin-1-yl)-xanthine, (7) 1-[(4-methyl-isoquinolin-1-yl)methyl]-3-methyl-7-(2-butyn-1-yl)-8-((S)-3-amino-piperidin-1-yl)-xanthine, (8) 1-[(4-methyl-isoquinolin-1-yl)methyl]-3-methyl-7-(2-butyn-1-yl)-8-((R)-3-amino-piperidin-1-yl)-xanthine, (9) 1-[2-(2,3-dihydro-benzo[1,4]dioxin-5-yl)-2-oxo-ethyl]-3-methyl-7-(2-butyn-1-yl)-8-(3-(R)-amino-piperidin-1-yl)-xanthine,

(10) 1-[(4-methoxy-naphthalen-1-yl)methyl]-3-methyl-7-(2-butyn-1-yl)-8-((S)-3-amino-piperidin-1-yl)-xanthine, (11)-[(4-methoxy-naphthalen-1-yl)methyl]-3-methyl-7-(2-butyn-1-yl)-8-((R)-3-amino-piperidin-1-yl)-xanthine,

(12) 1-[2-(benzo[1,3]dioxol-4-yl)-2-oxo-ethyl]-3-methyl-7-(2-butyn-1-yl)-8-((R)-3-amino-piperidin-1-yl)-xanthine,

(13) 1-[(4-methyl-quinazolin-2-yl)methyl]-3-methyl-7-(2-butyn-1-yl)-8-(3-(R)-amino-piperidin-1-yl)-xanthine,

(14) 1-(2-{2-[(methylaminocarbonyl)methoxy]-phenyl}-2-oxo-ethyl)-3-methyl-7-((E)-2-buten-1-yl)-8-((R)-3-amino-piperidin-1-yl)-xanthine,

(15) 1-(2-{2-[(methylaminocarbonyl)methoxy]-phenyl}-2-oxo-ethyl)-3-methyl-7-((E)-2-buten-1-yl)-8-((S)-3-amino-piperidin-1-yl)-xanthine,

(16) 1-(2-{2-[(isopropylcarbonyl)amino]-phenyl}-2-oxo-ethyl)-3-methyl-7-(2-butyn-1-yl)-8-((R)-3-amino-piperidin-1-yl)-xanthine,

(17) 1-[(4-cyano-naphthalen-1-yl)methyl]-3-methyl-7-(2-butyn-1-yl)-8-((R)-3-amino-piperidin-1-yl)-xanthine,

(18) 1-[(4-phenyl-quinazolin-2-yl)methyl]-3-methyl-7-(2-butyn-1-yl)-8-((R)-3-amino-piperidin-1-yl)-xanthine,

(19) 1-[(8-methyl-quinoxalin-6-yl)methyl]-3-methyl-7-(2-butyn-1-yl)-8-((R)-3-amino-piperidin-1-yl)-xanthine,

(20) 1-[(4-fluoro-naphthalen-1-yl)methyl]-3-methyl-7-(2-butyn-1-yl)-8-((R)-3-amino-piperidin-1-yl)-xanthine,

(21) 1-((E)-3-pentafluorophenyl-allyl)-3-methyl-7-(2-butyn-1-yl)-8-((R)-3-amino-piperidin-1-yl)-xanthine,

(22) 1-[(3-trifluoromethyl-isoquinolin-1-yl)methyl]-3-methyl-7-(2-butyn-1-yl)-8-((R)-3-amino-piperidin-1-yl)-xanthine,

(23) 1-[(3-difluoromethyl-isoquinolin-1-yl)methyl]-3-methyl-7-(2-butyn-1-yl)-8-((R)-3-amino-piperidin-1-yl)-xanthine,

(24) 1-[2-(biphenyl-2-yl)-2-oxo-ethyl]-3-methyl-7-(2-butyn-1-yl)-8-((R)-3-amino-piperidin-1-yl)-xanthine,

(25) 1-[(3-methyl-isoquinolin-1-yl)methyl]-3-cyclopropyl-7-(2-butyn-1-yl)-8-((R)-3-amino-piperidin-1-yl)-xanthine,

(26) 1-[2-(3-methoxy-phenyl)-2-oxo-ethyl]-3-methyl-7-(2-butyn-1-yl)-8-((R)-3-amino-piperidin-1-yl)-xanthine,

(27) 1-[(3-methyl-isoquinolin-1-yl)methyl]-3-methyl-7-(2-chloro-benzyl)-8-((R)-3-amino-piperidin-1-yl)-xanthine and

(28) 1-[(3-methyl-isoquinolin-1-yl)methyl]-3-methyl-7-(2-bromo-benzyl)-8-((R)-3-amino-piperidin-1-yl)-xanthine or tautomers, enantiomers, diastereomers, mixtures thereof or salts thereof.

2. A compound chosen from:

(1) 1-(2-cyano-ethyl)-3-methyl-7-(2-cyano-benzyl)-8-(3-amino-piperidin-1-yl)-xanthine, (2) 1-(2-{2-[(ethoxycarbonyl)methoxy]-phenyl}-2-oxo-ethyl)-3-methyl-7-(3-methyl-2-buten-1-yl)-8-(3-amino-piperidin-1-yl)-xanthine, (3) 1-(2-{2-[(aminocarbonyl)methoxy]-phenyl}-2-oxo-ethyl)-3-methyl-7-(3-methyl-2-buten-1-yl)-8-(3-amino-piperidin-1-yl)-xanthine, (4) 1-(2-{3-[(methanesulphinyl)methoxy]-phenyl}-2-oxo-ethyl)-3-methyl-7-(3-methyl-2-buten-1-yl)-8-(3-amino-piperidin-1-yl)-xanthine, (5) 1-(1-methyl-2-oxo-2-phenyl-ethyl)-3-methyl-7-(3-methyl-2-buten-1-yl)-8-(3-amino-piperidin-1-yl)-xanthine, (6) 1-(2-phenoxy-ethyl)-3-methyl-7-(2-cyano-benzyl)-8-(3-amino-piperidin-1-yl)-xanthine, (7) 1-(2-phenyl-2-oxo-ethyl)-7-(3-methyl-2-buten-1-yl)-8-(3-amino-piperidin-1-yl)-xanthine, (8) 1-(2-{3-[(ethoxycarbonyl)methoxy]-phenyl}-2-oxo-ethyl)-3-methyl-7-(3-methyl-2-buten-1-yl)-8-(3-amino-piperidin-1-yl)-xanthine, (9) 1-(2-{2-[(methylaminocarbonyl)methoxy]-phenyl}-2-oxo-ethyl)-3-methyl-7-(3-methyl-2-buten-1-yl)-8-(3-amino-piperidin-1-yl)-xanthine,

(10) 1-(2-{2-[(dimethylaminocarbonyl)methoxy]-phenyl}-2-oxo-ethyl)-3-methyl-7-(3-methyl-2-buten-1-yl)-8-(3-amino-piperidin-1-yl)-xanthine,

(11) 1-(2-methoxy-ethyl)-3-methyl-7-(2-cyano-benzyl)-8-(3-amino-piperidin-1-yl)-xanthine,

(12) 1-methyl-3-[(methoxycarbonyl)methyl]-7-(2-cyano-benzyl)-8-(3-amino-piperidin-1-yl)-xanthine,

(13) 1-methyl-3-cyanomethyl-7-(2-cyano-benzyl)-8-(3-amino-piperidin-1-yl)-xanthine,

(14) 1-methyl-3-(2-propyn-1-yl)-7-(2-cyano-benzyl)-8-(3-amino-piperidin-1-yl)-xanthine, (15)-{2-[3-(2-oxo-imidazolidin-1-yl)-phenyl]-2-oxo-ethyl}-3-methyl-7-(3-methyl-2-buten-1-yl)-8-(3-amino-piperidin-1-yl)-xanthine,

(16) 1-methyl-3-(2-propen-1-yl)-7-(2-cyano-benzyl)-8-(3-amino-piperidin-1-yl)-xanthine,

(17) 1-(2-{2-[(ethylcarbonyl)amino]-phenyl}-2-oxo-ethyl)-3-methyl-7-(3-methyl-2-buten-1-yl)-8-(3-amino-piperidin-1-yl)-xanthine,

(18) 1-methyl-3-phenyl-7-(2-cyano-benzyl)-8-(3-amino-piperidin-1-yl)-xanthine,

(19) 1-[2-(2-amino-phenyl)-2-oxo-ethyl]-3-methyl-7-(3-methyl-2-buten-1-yl)-8-((S)-3-amino-piperidin-1-yl)-xanthine,

(20) 1-(2-phenyl-2-oxo-ethyl)-3-cyanomethyl-7-(3-methyl-2-buten-1-yl)-8-(3-amino-piperidin-1-yl)-xanthine,

(21) 1-[(quinolin-2-yl)methyl]-3-methyl-7-(3-methyl-2-buten-1-yl)-8-(3-amino-piperidin-1-yl)-xanthine,

(22) 1-[(2-oxo-2H-chromen-4-yl)methyl]-3-methyl-7-(3-methyl-2-buten-1-yl)-8-(3-amino-piperidin-1-yl)-xanthine,

(23) 1-[(cinnolin-4-yl)methyl]-3-methyl-7-(3-methyl-2-buten-1-yl)-8-(3-amino-piperidin-1-yl)-xanthine,

(24) 1-[(1-methyl-2-oxo-1,2-dihydro-quinolin-4-yl)methyl]-3-methyl-7-(3-methyl-2-buten-1-yl)-8-(3-amino-piperidin-1-yl)-xanthine,

(25) 1-[(4-oxo-3,4-dihydro-phthalazin-1-yl)methyl]-3-methyl-7-(3-methyl-2-buten-1-yl)-8-(3-amino-piperidin-1-yl)-xanthine,

(26) 1-[(quinazolin-4-yl)methyl]-3-methyl-7-(3-methyl-2-buten-1-yl)-8-(3-amino-piperidin-1-yl)-xanthine,

(27) 1-[(5-methyl-3-phenyl-isoxazol-4-yl)methyl]-3-methyl-7-(3-methyl-2-buten-1-yl)-8-(3-amino-piperidin-1-yl)-xanthine,

(28) 1-[(isoquinolin-3-yl)methyl]-3-methyl-7-(3-methyl-2-buten-1-yl)-8-(3-amino-piperidin-1-yl)-xanthine,

(29) 1-[(3-phenyl-[1,2,4]oxadiazol-5-yl)methyl]-3-methyl-7-(3-methyl-2-buten-1-yl)-8-(3-amino-piperidin-1-yl)-xanthine,

(30) 1-[(4-phenyl-pyridin-2-yl)methyl]-3-methyl-7-(3-methyl-2-buten-1-yl)-8-(3-amino-piperidin-1-yl)-xanthine,

(31) 1-[(5-phenyl-pyridin-2-yl)methyl]-3-methyl-7-(3-methyl-2-buten-1-yl)-8-(3-amino-piperidin-1-yl)-xanthine,

(32) 1-[(3-methyl-4-oxo-3,4-dihydro-phthalazin-1-yl)methyl]-3-methyl-7-(3-methyl-2-buten-1-yl)-8-(3-amino-piperidin-1-yl)-xanthine,

(33) 1-[2-(3-methylsulphanyl-phenyl)-2-oxo-ethyl]-3-methyl-7-(3-methyl-2-buten-1-yl)-8-(3-amino-piperidin-1-yl)-xanthine,

(34) 1-[2-(3-methanesulphinyl-phenyl)-2-oxo-ethyl]-3-methyl-7-(3-methyl-2-buten-1-yl)-8-(3-amino-piperidin-1-yl)-xanthine,

(35) 1-[2-(3-methanesulphonyl-phenyl)-2-oxo-ethyl]-3-methyl-7-(3-methyl-2-buten-1-yl)-8-(3-amino-piperidin-1-yl)-xanthine,

(36) 1-[2-(3-carboxy-phenyl)-2-oxo-ethyl]-3-methyl-7-(3-methyl-2-buten-1-yl)-8-(3-amino-piperidin-1-yl)-xanthine,

(37) 1-[2-(3-methoxycarbonyl-phenyl)-2-oxo-ethyl]-3-methyl-7-(3-methyl-2-buten-1-yl)-8-(3-amino-piperidin-1-yl)-xanthine, (38)-{2-[3-(methylaminocarbonyl)-phenyl]-2-oxo-ethyl}-3-methyl-7-(3-methyl-2-buten-1-yl)-8-(3-amino-piperidin-1-yl)-xanthine,

(39) 1-{2-[3-(dimethylaminocarbonyl)-phenyl]-2-oxo-ethyl}-3-methyl-7-(3-methyl-2-buten-1-yl)-8-(3-amino-piperidin-1-yl)-xanthine,

(40) 1-{2-[3-(morpholin-4-yl-carbonyl)-phenyl]-2-oxo-ethyl}-3-methyl-7-(3-methyl-2-buten-1-yl)-8-(3-amino-piperidin-1-yl)-xanthine,

(41) 1-[2-(2-carboxy-phenyl)-2-oxo-ethyl]-3-methyl-7-(3-methyl-2-buten-1-yl)-8-(3-amino-piperidin-1-yl)-xanthine,

(42) 1-[2-(2-ethoxycarbonyl-phenyl)-2-oxo-ethyl]-3-methyl-7-(3-methyl-2-buten-1-yl)-8-(3-amino-piperidin-1-yl)-xanthine,

(43) 1-{2-[2-(dimethylaminocarbonyl)-phenyl]-2-oxo-ethyl}-3-methyl-7-(3-methyl-2-buten-1-yl)-8-(3-amino-piperidin-1-yl)-xanthine,

(44) 1-{2-[2-(morpholin-4-yl-carbonyl)-phenyl]-2-oxo-ethyl}-3-methyl-7-(3-methyl-2-buten-1-yl)-8-(3-amino-piperidin-1-yl)-xanthine,

(45) 1-[2-(2,6-dimethoxy-phenyl)-2-oxo-ethyl]-3-methyl-7-(3-methyl-2-buten-1-yl)-8-(3-amino-piperidin-1-yl)-xanthine,

(46) 1-((E)-3-phenyl-allyl)-3-methyl-7-(3-methyl-2-buten-1-yl)-8-(3-amino-piperidin-1-yl)-xanthine,

(47) 1-[(benzo[b]thiophen-3-yl)methyl]-3-methyl-7-(3-methyl-2-buten-1-yl)-8-(3-amino-piperidin-1-yl)-xanthine,

(48) 1-[(1H-indol-3-yl)methyl]-3-methyl-7-(3-methyl-2-buten-1-yl)-8-(3-amino-piperidin-1-yl)-xanthine,

(49) 1-[(biphenyl-4-yl)methyl]-3-methyl-7-(3-methyl-2-buten-1-yl)-8-(3-amino-piperidin-1-yl)-xanthine,

(50) 1-(2-cyclohexyl-2-oxo-ethyl)-3-methyl-7-(3-methyl-2-buten-1-yl)-8-(3-amino-piperidin-1-yl)-xanthine,

(51) 1-(3,3-dimethyl-2-oxo-butyl)-3-methyl-7-(3-methyl-2-buten-1-yl)-8-(3-amino-piperidin-1-yl)-xanthine,

(52) 1-({5-[(methoxycarbonyl)methylamino]-isoquinolin-1-yl}methyl)-3-methyl-7-(3-methyl-2-buten-1-yl)-8-(3-amino-piperidin-1-yl)-xanthine,

(53) 1-(2-dimethylamino-2-oxo-ethyl)-3-methyl-7-(3-methyl-2-buten-1-yl)-8-(3-amino-piperidin-1-yl)-xanthine,

(54) 1-[2-(piperidin-1-yl)-2-oxo-ethyl]-3-methyl-7-(3-methyl-2-buten-1-yl)-8-(3-amino-piperidin-1-yl)-xanthine,

(55) 1-[(2-methyl-1-oxo-1,2-dihydro-isoquinolin-4-yl)methyl]-7-(3-methyl-2-buten-1-yl)-8-(3-amino-piperidin-1-yl)-xanthine,

(56) 1-[2-(2,3-dimethoxy-phenyl)-2-oxo-ethyl]-3-methyl-7-(3-methyl-2-buten-1-yl)-8-(3-amino-piperidin-1-yl)-xanthine,

(57) 1-[2-(pyrrolidin-1-yl)-2-oxo-ethyl]-3-methyl-7-(3-methyl-2-buten-1-yl)-8-(3-amino-piperidin-1-yl)-xanthine,
(58) 1-[2-(2,3-dihydro-benzo[1,4]dioxin-5-yl)-2-oxo-ethyl]-3-methyl-7-(3-methyl-2-buten-1-yl)-8-(3-amino-piperidin-1-yl)-xanthine,
(59) 1-[2-(3-methyl-2-oxo-2,3-dihydro-benzooxazol-7-yl)-2-oxo-ethyl]-3-methyl-7-(3-methyl-2-buten-1-yl)-8-(3-amino-piperidin-1-yl)-xanthine,
(60) 1-[2-(benzo[1,3]dioxol-4-yl)-2-oxo-ethyl]-3-methyl-7-(3-methyl-2-buten-1-yl)-8-(3-amino-piperidin-1-yl)-xanthine,
(61) 1-methyl-3-isopropyl-7-(2-cyano-benzyl)-8-(3-amino-piperidin-1-yl)-xanthine,
(62) 1-[2-(2-cyanomethylamino-phenyl)-2-oxo-ethyl]-3-methyl-7-(3-methyl-2-buten-1-yl)-8-(3-amino-piperidin-1-yl)-xanthine,
(63) 1-[(isoquinolin-1-yl)methyl]-3-[(methoxycarbonyl)methyl]-7-(3-methyl-2-buten-1-yl)-8-(3-amino-piperidin-1-yl)-xanthine,
(64) 1-(2-{2-[(isopropyloxycarbonyl)methoxy]-phenyl}-2-oxo-ethyl)-3-methyl-7-(3-methyl-2-buten-1-yl)-8-(3-amino-piperidin-1-yl)-xanthine,
(65) 1-[2-(2-{[(ethoxycarbonylamino)carbonyl]amino}-phenyl)-2-oxo-ethyl]-3-methyl-7-(3-methyl-2-buten-1-yl)-8-(3-amino-piperidin-1-yl)-xanthine,
(66) 1-[2-(2-acetylamino-phenyl)-2-oxo-ethyl]-3-methyl-7-(3-methyl-2-buten-1-yl)-8-((S)-3-amino-piperidin-1-yl)-xanthine,
(67) 1-(2-{2-[(methylaminocarbonyl)methoxy]-phenyl}-2-oxo-ethyl)-3-methyl-7-(3-methyl-2-buten-1-yl)-8-((S)-3-amino-piperidin-1-yl)-xanthine,
(68) 1-methyl-7-(2-cyano-benzyl)-8-(3-amino-piperidin-1-yl)-xanthine,
(69) 1-(2-{2-[(isopropylcarbonyl)amino]-phenyl}-2-oxo-ethyl)-3-methyl-7-(3-methyl-2-buten-1-yl)-8-(3-amino-piperidin-1-yl)-xanthine,
(70) 1-(2-{2-[(methoxycarbonyl)amino]-phenyl}-2-oxo-ethyl)-3-methyl-7-(3-methyl-2-buten-1-yl)-8-(3-amino-piperidin-1-yl)-xanthine,
(71) 1-[2-(3-methyl-2-oxo-2,3-dihydro-benzooxazol-4-yl)-2-oxo-ethyl]-3-methyl-7-(3-methyl-2-buten-1-yl)-8-(3-amino-piperidin-1-yl)-xanthine,
(72) 1-[2-(2-nitro-3-methoxy-phenyl)-2-oxo-ethyl]-3-methyl-7-(3-methyl-2-buten-1-yl)-8-(3-amino-piperidin-1-yl)-xanthine,
(73) 1-[2-(2-amino-3-methoxy-phenyl)-2-oxo-ethyl]-3-methyl-7-(3-methyl-2-buten-1-yl)-8-(3-amino-piperidin-1-yl)-xanthine,
(74) 1-[(3-methyl-isoquinolin-1-yl)methyl]-3-methyl-7-(3-methyl-1-buten-1-yl)-8-((R)-3-amino-piperidin-1-yl)-xanthine,
(75) 1-[(3-methyl-isoquinolin-1-yl)methyl]-3-methyl-7-(2-cyano-benzyl)-8-(3-amino-piperidin-1-yl)-xanthine,
(76) 1-[2-(3-carboxymethoxy-phenyl)-2-oxo-ethyl]-3-methyl-7-(3-methyl-2-buten-1-yl)-8-(3-amino-piperidin-1-yl)-xanthine and
(77) 1-[2-(2-carboxymethoxy-phenyl)-2-oxo-ethyl]-3-methyl-7-(3-methyl-2-buten-1-yl)-8-(3-amino-piperidin-1-yl)-xanthine,
or tautomers, enantiomers, diastereomers, mixtures thereof or the salts thereof.

3. A physiologically acceptable salt of a compound according to claim 1 or 2 with an inorganic or organic acid or base.

4. A pharmaceutical composition comprising a pharmaceutically acceptable amount of a compound according to claim 1 or 3 optionally together with one or more inert carriers and/or diluents.

5. A compound of formula (I)

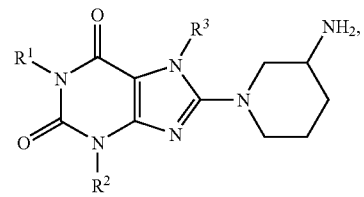

wherein
 $R^1$ is 4-methyl-2-quinazolinylmethyl;
 $R^2$ is methyl; and
 $R^3$ is 2-butyn-1-yl.

6. A pharmaceutical composition comprising one or more inert carriers or diluents and a compound of formula (I)

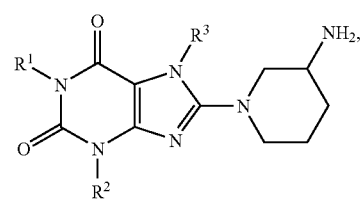

wherein
 $R^1$ is 4-methyl-2-quinazolinylmethyl;
 $R^2$ is methyl; and
 $R^3$ is 2-butyn-1-yl.

7. A salt of a compound of formula (I)

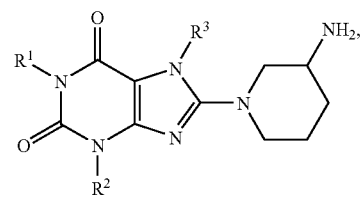

wherein
 $R^1$ is 4-methyl-2-quinazolinylmethyl;
 $R^2$ is methyl; and
 $R^3$ is 2-butyn-1-yl.

8. A physiologically acceptable salt of a compound of formula (I)

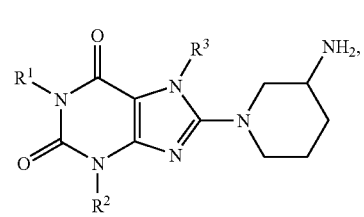

wherein
R¹ is 4-methyl-2-quinazolinylmethyl;
R² is methyl; and
R³ is 2-butyn-1-yl.

9. A pharmaceutical composition comprising one or more inert carriers or diluents and a physiologically acceptable salt of a compound of formula (I)

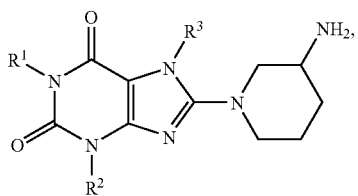
(I)

wherein
R¹ is 4-methyl-2-quinazolinylmethyl;
R² is methyl; and
R³ is 2-butyn-1-yl.

10. A salt of a compound of formula (I)

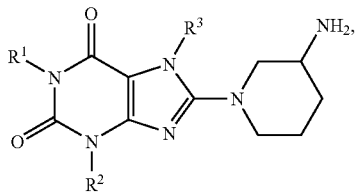
(I)

wherein
R¹ is 4-methyl-2-quinazolinylmethyl;
R² is methyl; and
R³ is 2-butyn-1-yl,
with an inorganic or organic acid.

11. A physiologically acceptable salt of a compound of formula (I)

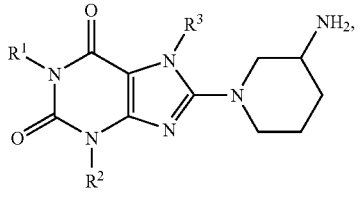
(I)

wherein
R¹ is 4-methyl-2-quinazolinylmethyl;
R² is methyl; and
R³ is 2-butyn-1-yl,
with an inorganic or organic acid.

12. A pharmaceutical composition comprising one or more inert carriers or diluents and a physiologically acceptable salt of a compound of formula (I)

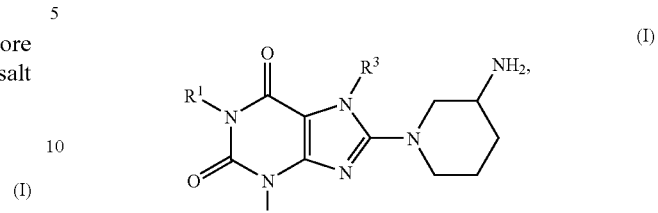
(I)

wherein
R¹ is 4-methyl-2-quinazolinylmethyl;
R² is methyl; and
R³ is 2-butyn-1-yl,
with an inorganic or organic acid.

13. The compound 1-[(4-methyl-quinazolin-2-yl) methyl]-3-methyl-7-(2-butyn-1-yl)-8-(3-(R)-amino-piperidin-1-yl)-xanthine of the formula

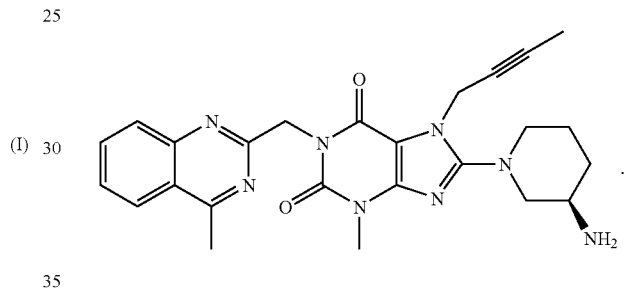

14. A pharmaceutical composition comprising one or more inert carriers or diluents and the compound 1-[(4-methyl-quinazolin-2-yl) methyl]-3-methyl-7-(2-butyn-1-yl)-8-(3-(R)-amino-piperidin-1-yl)-xanthine of the formula

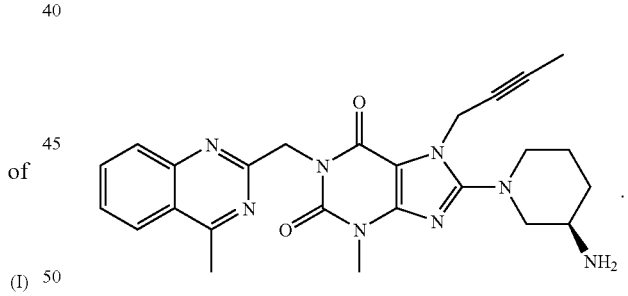

15. A salt of the compound 1[(4-methyl-quinazolin-2-yl) methyl]-3-methyl-7-(2-butyn-1-yl)-8-(3-(R)-amino-piperidin-1-yl)-xanthine of the formula

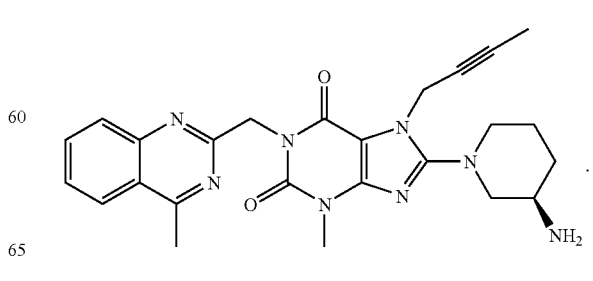

16. A physiologically acceptable salt of the compound 1-[(4-methyl-quinazolin-2-yl) methyl]-3-methyl-7-(2-butyn-1-yl)-8-(3-(R)-amino-piperidin-1-yl)-xanthine of the formula

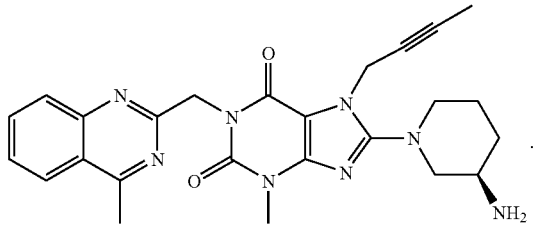

17. A pharmaceutical composition comprising one or more inert carriers or diluents and a physiologically acceptable salt of the compound 1-[(4-methyl-quinazolin-2-yl) methyl]-3-methyl-7-(2-butyn-1-yl)-8-(3-(R)-amino-piperidin-1-yl)-xanthine of the formula

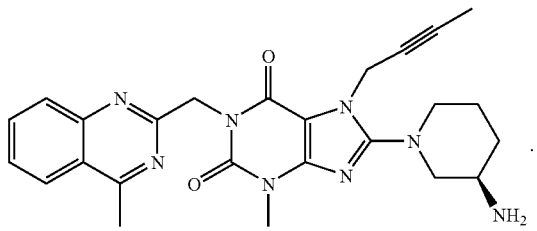

18. A salt of the compound 1-[(4-methyl-quinazolin-2-yl) methyl]-3-methyl-7-(2-butyn-1-yl)-8-(3-(R)-amino-piperidin-1-yl-xanthine of the formula

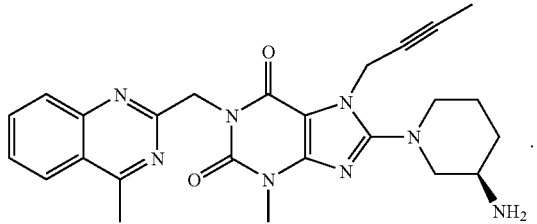

with an inorganic or organic acid.

19. A physiologically acceptable salt of the compound 1-[(4-methyl-quinazolin-2-yl) methyl]-3-methyl-7-(2-butyn-1-yl)-8-(3-(R)-amino-piperidin-1-yl)-xanthine of the formula

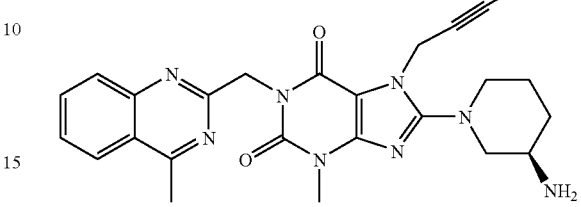

with an inorganic or organic acid.

20. A pharmaceutical composition comprising one or more inert carriers or diluents and a physiologically acceptable salt of the compound 1-[(4-methyl-quinazolin-2-yl) methyl]-3-methyl-7-(2-butyn-1yl)-8-(3-(R)-amino-piperidin-1-yl)-xanthine of the formula

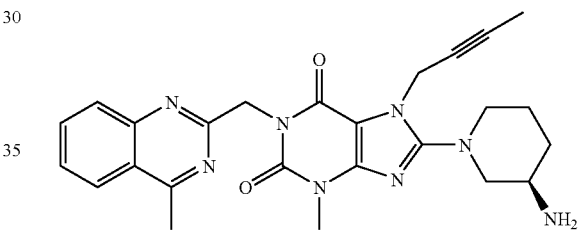

with an inorganic or organic acid.

21. A pharmaceutical composition comprising a pharmaceutically acceptable amount of a physiologically acceptable salt according to claim 3, optionally together with one or more inert carriers and/or diluents.

* * * * *

UNITED STATES PATENT AND TRADEMARK OFFICE
CERTIFICATE OF CORRECTION

PATENT NO.          : 7,407,955 B2                                    Page 1 of 1
APPLICATION NO. : 10/639036
DATED               : August 5, 2008
INVENTOR(S)         : Himmelsbach et al.

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by 167 days Delete the phrase "by 167 days" and insert -- by 0 days --

Signed and Sealed this

Twenty-fourth Day of November, 2009

David J. Kappos
*Director of the United States Patent and Trademark Office*